(12) United States Patent
Peterson

(10) Patent No.: US 9,109,235 B2
(45) Date of Patent: Aug. 18, 2015

(54) METHODS AND COMPOSITIONS FOR DEGRADING PECTIN

(71) Applicant: UNIVERSITY OF GEORGIA RESEARCH FOUNDATION, INC., Athens, GA (US)

(72) Inventor: Joy Bethune Peterson, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 13/942,189

(22) Filed: Jul. 15, 2013

(65) Prior Publication Data

US 2014/0004588 A1     Jan. 2, 2014

Related U.S. Application Data

(62) Division of application No. 13/063,272, filed as application No. PCT/US2009/057508 on Sep. 18, 2009, now abandoned.

(60) Provisional application No. 61/097,975, filed on Sep. 18, 2008, provisional application No. 61/179,570, filed on May 19, 2009.

(51) Int. Cl.

| C12P 7/14 | (2006.01) |
|---|---|
| C12P 7/06 | (2006.01) |
| C12N 9/24 | (2006.01) |
| C12N 9/26 | (2006.01) |
| C12N 1/20 | (2006.01) |
| C12N 1/00 | (2006.01) |
| C12N 9/40 | (2006.01) |

(52) U.S. Cl.
CPC ............ *C12P 7/14* (2013.01); *C12N 9/2465* (2013.01); *C12P 7/06* (2013.01); *C12Y 302/01015* (2013.01); *Y02E 50/17* (2013.01)

(58) Field of Classification Search
CPC ........... C12N 9/2465; C12P 7/06; C12P 7/14; C12Y 302/01015; Y02E 50/17
USPC ........... 435/162, 161, 200, 201, 252.8, 252.3, 435/254.21, 254.11
See application file for complete search history.

(56) References Cited

U.S. PATENT DOCUMENTS

| 3,844,890 | A | 10/1974 | Horikoshi et al. |
|---|---|---|---|
| 4,435,307 | A | 3/1984 | Barbesgaard et al. |
| 4,461,648 | A | 7/1984 | Foody |
| 4,600,590 | A | 7/1986 | Dale |
| 4,703,004 | A | 10/1987 | Hopp et al. |
| 4,782,137 | A | 11/1988 | Hopp et al. |
| 5,037,663 | A | 8/1991 | Dale |
| 5,258,297 | A | 11/1993 | Akiba et al. |
| 5,447,862 | A | 9/1995 | Heim et al. |
| 5,594,115 | A | 1/1997 | Sharma |
| 5,858,760 | A | 1/1999 | Dalboge et al. |
| 5,935,824 | A | 8/1999 | Sgarlato |
| 5,972,118 | A | 10/1999 | Hester et al. |
| 6,102,690 | A | 8/2000 | Ingram et al. |
| 6,429,000 | B1 | 8/2002 | Andersen et al. |
| 7,026,152 | B2 | 4/2006 | Ingram et al. |
| 7,273,745 | B2 | 9/2007 | Andersen et al. |
| 2006/0210971 | A1 | 9/2006 | Kerovuo et al. |
| 2009/0093028 | A1 | 4/2009 | Peterson et al. |
| 2012/0094347 | A1 | 4/2012 | Peterson |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Akita et al., "The first structure of pectate lyase belonging to polysaccharide lyase family 3." *Acta Crystallographica*, 2001; D57: 1786-1792.
Alkasrawi et al., "Influence of strain and cultivation procedure on the performance of simultaneous saccharification and fermentation of steam pretreated spruce." *Enzyme and Microbial Technology*, 2006; 38: 279-287.
Altschul et al., "Gapped BLAST and PSI-BLAST: a new generation of protein database search programs." *Nucleic Acids Research*, 1997; 25(17): 3389-3402.
Atlas et al. *Handbook of Microbiological Media*. CRC Press Inc., Boca Raton, Florida, 1993.
Atsumi et al., "Metabolic engineering of *Escherichia coli* for 1-butanol production." *Metabolic Engineering*, 2008; 10: 305-311.
Bao et al. "An improved Tn7-based system for the single-copy insertion of cloned genes into chromosomes of Gram-negative bacteria." *Gene* 1991; 109: 167-168.
Barras et al., "Extracellular enzymes and pathogenesis of soft-rot Erwinia." *Annu. Rev. Phytopathol.*, 1994; 32:201-234.
Beguin et al., "The biological degradation of cellulose." *FEMS Microbiology Reviews*, 1994; 13(1): 25-58.

(Continued)

*Primary Examiner* — Ganapathirama Raghu
(74) *Attorney, Agent, or Firm* — Mueting, Raasch & Gebhardt, P.A.

(57) ABSTRACT

The present invention provides enriched polynucleotides, and enriched polypeptides having pectinase activity. The present invention also includes methods of using the polynucleotides and polypeptides described herein. For instance, the methods include producing metabolic product, such as ethanol.

13 Claims, 12 Drawing Sheets

(56) References Cited

OTHER PUBLICATIONS

Berensmeier et al. "Cloning of the *pelA* gene from *Bacillus licheniformis* 14A and biochemical characterizationof recombinant, thermostable, high-alkaline pectate lyase." *Appl. Biochem. Biotechol.* 2004; 64: 560-567.
Blot et al., "The Oligogalacturonate-specific Porin KdgM of *Erwinia chrysanthemi* Belongs to a New Porin Family" *Journal of Biological Chemistry*, 2002; 277(10): 7936-7944.
Bowie et al., "Deciphering the Message in Protein Sequences: Tolerance to Amino Acid Substitutions." *Science.* 1990; 247: 1306-1310.
Bradford, "A rapid and sensitive method for the quantitation of microgram quantities of protein utilizing the principle of protein-dye binding." *Analytical Biochemistry*, 1976; 72: 248-254.
Broun et al. "Catalytic Plasticity of Fatty Acid Modification Enzymes Underlying Chemical Diversity of Plant Lipids" 1998. *Science.* 282:1315-1317.
Collmer et al., "Impaired induction and self-catabolite repression of extracellular pectate lyase in *Erwinia chrysanthemi* mutants deficient in oligogalacturonide lyase." *Proc. Natl. Acad. Sci.*, 1981; 78: 3920-3924.
Collmer et al., "Assay methods for pectic enzymes." pp. 329-335. *In* Wood and Kellogg (eds.), *Methods in Enzymology*, 1988; vol. 161. Academic Press, Inc., San Diego, CA.
Cook et al., "Isolation of polymer-degrading bacteria and characterization of the hindgut bacterial community from the detritus-feeding larvae of *Tipula abdominalis* (Diptera: Tipulidae)." *Applied and Environmental Microbiology*, 2007; 73: 5683-5686.
Coutinho et al., "Carbohydrate-active enzymes: an integrated database approach." in: Gilbert et al. (eds) *Recent Advances in Carbohydrate Bioengineering*. Cambridge, The Royal Society of Chemistry, 1999.
Datsenko et al., "One-step inactivation of chromosomal genes in *Escherichia coli* K-12 using PCR products." *Proc. Natl. Acad. Sci.*, 2000; 97(12): 6640-6645.
Devos et al. "Practical Limits of Function Prediction" 2000. *Proteins: Structure, Function and Genetics*. 41:98-107.
Doran, et al. "Fermentations of pectin-rich biomass with recombinant bacteria to produce fuel ethanol." *Applied Biochemistry and Biotechnology*, 2000; 84-86: 141-152.
Doran et al., "Ethanol production from sugar beet pulp using engineered bacteria." *International Sugar Journal*. 2000; 102: 336-340.
Doran-Peterson et al., "Microbial Conversion of Sugars from Plant Biomass to Lactic Acid or Ethanol." *The Plant Journal*, 2008; 54: 582-592.
Doran Peterson et al., "Anaerobic respiration in engineered *Escherichia coli* with an internal electron acceptor to produce fuel ethanol." *Ann. N.Y. Acad. Sci.*, 2008; 1125: 363-372.
Eggeman et al., "Process and economic analysis of pretreatment technologies." *Bioresource Technology*, 2005; 96: 2019-2025.
Fargione et al., "Land clearing and the biofuel carbon debt." *Science*, 2008; 319: 1235-1237.
Galbe et al., "A review of the production of ethanol from softwood." *Applied Microbiology and Biotechnology*, 2002; 59: 618-628.
Gardner, "Analysis of Pectate Lyase Activity in Pectin-rich Lignocellulosic Biomass Fermentation." May 2009 Thesis. Submitted to the Honors Council of the University of Georgia, Athens, Georgia. 32 total pages.
Genbank Accession No. AAA24825. National Center for Biotechnology Information, National Library of Medicine, National Institutes of Health. "oligogalacturonate lyasae (ogl) [Erwinia chrysanthemi]". Retrieved from the Internet on Feb. 11, 2013. Retrieved from http://www.ncbi.nlm.nih.gov/protein/AAA24825. 1 page.
Genbank Accession No. EU848570. National Center for Biotechnology Information, National Library of Medicine, National Institutes of Health. "Cloning vector pLO12708, complete sequence". Retrieved from the Internet on Feb. 11, 2013. Retrieved from http://www.ncbi.nlm.nih.gov/nuccore/EU848570. 1 page.
Genbank Accession number BAA05383. National Center for Biotechnology Information, National Library of Medicine, National Institutes of Health. "pectate lyase [Bacillus sp. YA-14]". Retrieved from the Internet on Feb. 11, 2013. Retrieved from http://vvww.ncbi.nlm.nih.gov/protein/BAA05383. 1 page.
Genbank Accession Number CAB40884. National Center for Biotechnology Information, National Library of Medicine, National Institutes of Health. "pectate lyase [Paenibacillus barcinonensis]". Retrieved from the Internet on Feb. 11, 2013. Retrieved from http://www.ncbi.nlm.nih.gov/protein/CAB40884. 1 page.
Gilkes et al., "Domains in microbial β-1, 4-glycanases: sequence conservation, function, and enzyme families." *Microbiological Review*, 1991; 55(2): 303-315.
Gong et al., "Ethanol Production from Renewable Resources." *Advances in Biochemical Engineering and Biotechnology*. 1999; 65:207-241.
Gray et al., "Bioethanol." *Current Opinion in Chemical Biology*, 2006; 10: 141- 146.
Guo et al., "Cloning of a novel constitutively expressed pectate lyase gene *pelB* from *Fusarium solani* f. sp. *pisi*(*Nectria haematoccoa*, mating type VI) and characterization of the gene product expressed in *Pichia pastoris*." *Journal of Bacteriology*, 1995; 177(24): 7070-7077.
Gusakov et al., "Kinetics of the enzymatic hydrolysis of cellulose: 1. A mathematical model for a batch reactor process." *Enzyme and Microb. Technol.*, 1985; 7: 346-352.
Gusakov et al., "Enhancement of Enzymatic Cellulose Hydrolysis Using a Novel Type of Bioreactor with Intensive Stirring Induced by Electromagnetic Field." *Applied Biochemistry and Biotechnology*, 1996; 56: 141-153.
Hamasaki et al., "Spoilage Ability of Psychrotrophic Paenibacillus spp. Isolated from Cooked Food Products." *Biocontrol Science*, 2006; 11(1):43-47.
Harlow E. et al., *Antibodies: A Laboratory Manual*. Cold Spring Harbor Laboratory Press. Cold Spring Harbor, New York. 1988.
Hatada et al., "Deduced amino-acid sequence and possible catalytic residues of a novel pectate lyase from an alkaliphilic strain of *Bacillus*." *Eur. J. Biochem.*, 2000; 267: 2268-2275.
He et al., "Cloned *Erwinia chrysanthemi out* genes enable *Escherichia coli* to selectively secrete a diverse family of heterologous proteins to its milieu." *Proc. Natl. Acad. Sci.*, 1991; 88: 1079-1083.
Heikinheimo et al., "Characterization of a novel pectate lyase from *Erwinia carotovora* subsp. *carotovora*." *Molecular Plant-Microbe Interactions*, 1995; 8(2): 207-217.
Henriksen et al., "Polymyxin E production by *P. amylolyticus*." *Letters Applied Microbiology*, 2007; 45: 491-496.
Henrissat et al., "Functional implications of structure-based sequence alignment of proteins in the extracellular pectate lyase superfamily." *Plant Physiology*, 1995; 107: 963-976.
Henrissat et al., "Cellulase families revealed by hydrophobic cluster analysis." *Gene*, 1989; 81(1): 83-95.
Herron et al., "Structure and function of pectic enzymes: virulence factors of plant pathogens." *Proc. Natl. Acad. Sci.*, 2000; 97: 8762-8769.
Hoondal et al., "Microbial alkaline pectinases and their industrial applications: a review." *Appl. Microbiol. Biotechnology*, 2002; 59: 409-418.
International Search Report and Written Opinion, issued May 12, 2010 in Europe. International Application No. PCT/US2009/057508, filed Sep. 18, 2009. 17 pages total.
Jayani et al., "Microbial pectinolytic enzymes: a review." *Process Biochemistry*, 2005; 40: 2931-2944.
Jurnak et al., "Functional implications of the three-dimensional structures of pectate lyases." in: Visser and Voragen (eds.) *Pectin and Pectinases*. Amsterdam, Elsevier. 1996.
Kashyap et al., "Applications of pectinases in the commercial sector: a review." *Bioresource Technology*, 2001; 77: 215-227.
Keating et al., "An ethanologenic yeast exhibiting unusual metabolism in the fermentation of the lignocellulosic hexose sugars." *Journal of Industrial Microbiology and Biotechnology*, 2004; 31(5): 235-244.
Keen et al., "Structure of two pectate lyase genes from *Erwinia chrysanthemi* EC16 and their high-level expression in *Escherichia coli*." Journal of Bacteriology, 1986; 168(2): 595-606.

(56) References Cited

OTHER PUBLICATIONS

Kim et al., "Nucleotide sequence of the pectate lyase gene from alkali-tolerant *Bacillus* sp. YA-14." *Biosci. Biotech. Biochem.* 1994; 58: 947-949.

Kim et al., "*Paenibacillus pueri* sp. nov., isolated from Pu'er tea." *Int. J. Syst. Evol. Microbiol.*, 2009; 59: 1002-1006.

Klug et al., "Bacteria associated with the gut tract of larval stages of the aquatic crane fly *Tipula abdominalis*(Diptera; Tipulidae)." *Applied and Environmental Microbiology*, 1980; 40(2): 408-416.

Kluskens et al., "Molecular and biochemical characterization of the thermoactive family 1 pectate lyase from the hyperthermophilic bacterium *Thermotoga maritime*." *Biochemical Journal*, 2003; 370: 651-659.

Kunst et al., "The complete genome sequence of the Gram-positive bacterium Bacillus subtilis." *Nature*, 1997; 390(6657): 249-256.

Lai et al., "Cloning of cellobiose phosphoenolpyruvate-dependent phosphotransferase genes: functional expression in recombinant *Escherichia coli* and identification of a putative binding region for disaccharides." *Applied and Environmental Microbiology*, 1997; 63(2): 355-363.

Lindeberg et al., "Analysis of eight out genes in a cluster required for pectic enzyme secretion by *Erwinia chrysanthemi*: sequence comparison with secretion genes from other gram-negative bacteria." *Journal of Bacteriology*, 1992; 174(22): 7385-7397.

Lindeberg et al., "Complementation of deletion mutations in a cloned functional cluster of Erwinia chrysanthemi out genes with *Erwinia carotovora out homologues* reveals OutC and OutD as candidate gatekeepers of species-specific secretion of proteins via the type II pathway." *Molecular Microbiology*, 1996; 20(1): 175-190.

Liu et al., "Nucleotide sequence and expression of a novel pectate lyase gene (*pel-3*) and a closely linked endopolygalacturonase gene (*peh-1*) of *Erwinia carotovora* subsp. *carotovora* 71." *Applied and Environmental Microbiology*, 1994; 60(7): 2545-2552.

Lynd et al., "Microbial cellulose utilization: fundamentals and biotechnology." *Microbiology and Molecular Biology Reviews*, 2002; 66(3): 506-577.

Lynd et al., "How biotech can transform biofuels." *Nature Biotechnology*, 2008; 26: 169-172.

Mes-Hartree et al., "Comparison of steam and ammonia pretreatment for enzymatic hydrolysis of cellulose." *Applied Microbiology and Biotechnology*, 1988; 29: 462-468.

Meselson et al., "DNA restriction enzyme from *E. coli*." *Nature*, 1968; 217(5134): 1110-1114.

Miller, G. L. 1959. "Use of dinitrosalicylic acid reagent for determination of reducing sugar." *Analytical Chemistry*, 1959; 31: 426-428.

Moniruzzaman et al., "Isolation and molecular characterization of high-performance cellobiose-fermenting spontaneous mutants of ethanologenic *Escherichia coli* KO11 containing the *Klebsiella oxytoca casAB* operon." *Applied and Environmental Microbiology*, 1997; 63(12): 4633-4637.

Morjanoff et al., "Optimization of steam explosion as a method for increasing susceptibility of sugarcane bagasse to enzymatic saccharification." *Biotechnology and Bioengineering*, 1987; 29: 733-741.

Nasser et al., "Pectate lyase from *Bacillus subtilis*: molecular characterization of the gene, and properties of the cloned enzyme." *FEBS Letters*, 1993; 335: 319326.

Neuendorf et al., "Biochemical characterization of different genotypes of *Paenibacillus larvae* subsp. *larvae*, a honey bee bacterial pathogen." *Microbiology*, 2004; 150: 2381-2390.

Nielson et al., "Identification of prokaryotic and eukaryotic signal peptides and prediction of their cleavage sites." *Protein Engineering*, 1997; 10: 1-6.

Ohta et al., "Genetic improvement of *Escherichia coli* for ethanol production: chromosomal integration of *Zymomonas mobilis* genes encoding pyruvate decarboxylase and alcohol dehydrogenase II." Applied and Environmental Micdrobiology, 1991; 57(4): 893-900.

Olsson et al., "Fermentation of lignocellulosic hydrolysates for ethanol production." *Enzyme and Microbial Technology*, 1996; 18: 312-331.

Pan et al., "Biorefining of softwoods using ethanol organosolv pulping: preliminary evaluation of process streams for manufacture of fuel grade ethanol and co-products." *Biotechnology and Bioengineering*, 2005; 90: 473.

Pan et al., "Bioconversion of hybrid poplar to ethanol and co-products using an organosolv fractionation process: optimization of process yields." *Biotechnology and Bioengineering*, 2006; 94: 851-860.

Pan et al., "Organosolv ethanol lignin from hybrid poplar as a radical scavenger: relationship between lignin structure, extraction conditions, and antioxidant activity." *Journal of Agricultural and Food Chemistry*, 2006; 54: 5806-5813.

Pan et al., "Effect of organosolv ethanol pretreatment variables on physical characteristics of hybrid poplar substrates." *Applied Biochemistry and Biotechnology*, 2007; 136-140: 367-377.

Philippidis, "Cellulose bioconversion technology," In: *Handbook on Bioethanol: Production and Utilization*. Wyman (ed.), Taylor & Francis, Washington, DC. 1996; 179-212.

Posfai et al., "Versatile insertion plasmids for targeted genome manipulations in bacteria: isolation, deletion, and rescue of the pathogenicity island LEE of the *Escherichia coli* O157:H7 genome." *Journal of Bacteriology*, 1997; 179(13): 4426-4428.

Pugsley, "The complete general secretory pathway in gram-negative bacteria." *Microbiological Reviews*, 1993; 57: 50-108.

Qian et al., "Ethanol production from dilute-acid softwood hydrolysate by co-culture." *Applied Biochemistry and Biotechnology*, 2006; 134: 273-283.

Reverchon et al., "Nucleotide sequences of the *Erwinia chysanthemi ogl* and *pelE* genes negatively regulated by the *kdgR* gene product." *Gene*, 1989; 85: 125-134.

Rey et al. "Complete genome sequence of the industrial bacterium *Bacillus licheniformis* and comparisons with closely related *Bacillus* species." *Genome Biology*, 2004; 5(10): R77.

Ridley et al., "Pectins: structure, biosynthesis, and oligogalacturonide-related signaling." *Phytochemistry*, 2001; 57: 929-967.

Ryu et al., "Bioconversion of Waste Cellulose by Using an Attrition Bioreactor." *Biotechnology and Bioengineering*, 1983; 25: 53-65.

Sakai et al., "Pectin, pectinase, and protopectinase: production, properties, and applications." *Advances in Applied Microbiology*, 1993; 39: 213-294.

Sambrook et al., *Molecular cloning: a laboratory manual*, 2 ed. Cold Spring Harbor Laboratory, Cold Spring Harbor, NY, 1989.

Seffernick et al. "Melamine Deaminase and Atrazine Chlorohydrolase: 98 Percent Identical but Functionally Different" 2001. *Journ. Of Bacteriology*. 183(8):2405-2410.

Sheehan et al., "Enzymes, energy and the environment: a strategic perspective on the U.S. Department of Energy's research and development activities for bioethanol." *Biotechnology Progress*, 1999; 15(5): 817-827.

Shevchik et al., "Pectate lyase PeII of *Erwinia chrysanthemi* 3937 belongs to a new family." *Journal of Bacteriology*, 1997; 179: 7321-7330.

Shevchik et al. "Processing of the pectate lyase PeII by extracellular proteases of *Erwinia chrysanthemi* 3937." *Molecular Microbiology*, 1998; 29: 1459-1469.

Shevchik et al., "The exopolygalacturonate lyase PelW and the oligogalacturonate lyase Ogl, two cytoplasmic enzymes of pectin catabolism in *Erwinia chrysanthemi* 3937." *Journal of Bacteriology*, 1999; 181(13): 39123919.

Shevchik et al., "PaeX, a Second Pectin Acetylesterase of *Erwinia chrysanthemi* 3937." *Journal of Bacteriology*, 2003; 185(10):3091-3100.

Sinsabaugh et al., "Cellulose digestion and assimilation by three leaf-shredding aquatic insects." *Ecology*, 1985; 66: 1464-1471.

Soriano et al. An unusual pectate lyase from Bacillus sp. with high activity on pectin: cloning and characterization. 2000. *Microbiology*. 146:89-95.

Soriano et al., "Pectate lyase C from *Bacillus subtilis*: a novel endocleaving enzyme with activity on highly methylated pectin." *Microbiology*, 2006; 152: 617-625.

(56) References Cited

OTHER PUBLICATIONS

Spiro et al., "Purification and characterization of biologically active 1,4-linked α-D-oligogalacturonides after partial digestion of polygalacturonic acid with endopolygalacturonase." *Carbohydrate Research*, 1993; 247: 9-20.

Stabb et al., "RP4-based plasmids for conjugation between *Escherichia coli* and members of the Vibrionaceae." *Methods Enzymology*, 2002; 358: 413-426.

Starr et al., "Enzymatic degradation of polygalacturonic acid by *Yersinia* and *Klebsiella* species in relation to clinical laboratory procedures." *Journal of Clinical Microbiology*, 1977; 6(4): 379-386.

Sun et al., "Extraction and physico-chemical characterization of pectins from sugar beet pulp." *Polymer Journal*, 1998; 30(8): 671-677.

Sun et al., "Hydrolysis of lignocellulosic materials for ethanol production: a review." *Bioresource Technology*, 2002; 83: 1-11.

Tardy et al., "Comparative analysis of the five major *Erwinia chrysanthemi* pectate lyases: enzyme characteristics and potential inhibitors." *Journal of Bacteriology*, 1997; 179(8): 2503-2511.

Tatusova et al., "BLAST 2 sequences, a new tool for comparing protein and nucleotide sequences." *FEMS Microbiology Letters*, 1999; 174: 247-250.

Whisstock et al. "Prediction of protein function from protein sequence". 2003. *Q. Rev. Biophysics*. 36(3):307-340.

Whitaker, "Pectic substances, pectic enzymes and haze formation in fruit juices." *Enzyme Microbial Technology*, 1984; 6: 341-347.

Whitaker, *Principles of Enzymology for the Food Sciences*, 2nd Edition. Marcel Dekker, NY. 1994.

Willats et al., "Pectin: cell biology and prospects for functional analysis." *Plant Molecular Biology*, 2001; 47: 9-27.

Witkowski et al. "Conversion of β-ketoacyl synthase to a Malonyl Decarboxylase by replacement of the active cysteine with glutamine". 1999. *Biochemistry*. 38:11643-11650.

Wyman, "Biomass ethanol: Technical Progress, Opportunities, and Commercial Challenges." *Annual Review of Energy and the Environment*, 1999; 24: 189-226.

Xiao et al., "Improvement of the thermostability and activity of a pectate lyase by single amino acid substitutions, using a strategy based on melting-temperatureguided sequence alignment." *Applied and Environmental Microbiology*, 2008; 74(4):1183-1189.

Yadav et al., "Pectin lyase: a review." *Process Biochemistry*, 2009; 44: 1-10.

Zhou et al., "Enhancement of expression and apparent secretion of *Erwinia chrysanthemi* endoglucanase (encoded by *celZ*) in *Escherichia coli* B." *Applied and Environmental Microbiology*, 1999; 65(6): 2439-2445.

Zhou et al., "Engineering endoclucanase-secreting strains of ethanologenic *Klebsiella oxytoca* P2." *Journal of Industrial Microbiology and Biotechnology*, 1999; 22: 600-607 (Figure 1).

Seffernick et al. "Melamine Deaminase and Atrazine Chlorohydrolase: 98 Percent Identical but Functionally Different" 2001. "Journ. Of Bacteriology". 183(8):2405-2410.

Sheehan et al., "Enzymes, energy and the environment: a strategic perspective on the U.S. Depaantent of Energy's research and development activities for bioethanol." *Biotechnology Progress*, 1999; 15(5): 817-827.

Shevchik et al., "The exopolygalacturonate lyase PelW and the oligogalacturonate lyase Ogl, two cytoplasmic enzymes of pectin catabolism in *Erwinia chrysanthemi* 3937." *Journal of Bacteriology*, 1999; 181(13): 3912-3919.

Shevchik et al., "PaeX, a Second Pectin Acetylesterase of *Erwinia chrysanthemi* 3937." *Journal of Bacteriology*, 2003; 185(10):3091-3100.

Whitaker, *Principles of Enzymology for the Food Sciences*, 2nd Edition. Marcel Dekker, NY. 1994.

Witkowski et al. Conversion of β-ketoacyl synthase to a Malonyl Decarboxylase by replacement of the active cysteine with glutamine. 1999. *Biochemistry*. 38:11643-11650.

\* cited by examiner

```
BliYvpA     ---------------KGKRLIAGP-ELGDGS--QREDQKPIFKVEDGATLKNVVLGAP-AADG  91
BsuPelC     ---------------KGQRFVAGK-ELGDGS--QSENQDPVFRVEDGATLKNVVLGAP-AADG  90
BspP2850    ---------------KGKRLIAGP-ELGDGS--QREDQKPIFKVEDGATLKNVVLGAP-AADG  91
PamPelA     ---------------QGKTFVANPSTLGDGS--QAENQKPVFRLEAGATLKNVIIGAP-AADG  89
PbaPelA     ---------------QGKTFVANPSTLGDGS--QAENQKPVFRLEAGATLKNVIIGAP-AADG  89
BspKSM15    ---------------KGQTYVANPNTLGDGS--QAENQKPIFRLEAGASLKNVVIGAP-AADG  91
EcaPel3     AASPECKAGAVIKDKTVDCGGITLGLSCSGDSDKQPPVITLEN-ATIKNLRISEKGGSDG    177
EchPelI     KASSECKPGATFENRTVDCGGVTIGTSCPNDSDKQKPLIILKN-ATVKNLRISASGRADG    174
FsoPelB     ---------------GMKRFVRNPTTCKDQY--ETGEKDASFILEDGATLSNVIIDRS-SGEG  90
                                          :      . : ..: . .:: *::.*: :.  ..:*

BliYvpA     VHT-YGNASINNVVWEDVGEDALTV-KSEGSVTINGGSARLAA------DKIFQINKAS 142
BsuPelC     VHT-YGNVNIQNVKWEDVGEDALTV-KKEGKVTIDGGSAQKAS------DKIFQINKAS 141
BspP2850    VHT-YGNASINNVVWEDVGEDALTV-KSEGSVTINGGSARLAA------DKIFQINKAS 142
PamPelA     VHC-YGNCNISNVVWQDVGEDALTL-KSSGTVNITGGAAYKAY------DKVFQINAAG 140
PbaPelA     VHC-YGSCNISNVVWEDVGEDALTL-KSSGTVNITGGAAYKAY------DKVFQMNASG 140
BspKSM15    VHC-YGDCTITNVIWEDVGEDALTL-KSSGTVNISGGAAYKAY------DKVFQINAAG 142
EcaPel3     IHCKSGNCRIENVIWEDICEDAATN-LGK-TMTIVGGVAHNTTNGPGGKPDKVLQQNAKN 235
EchPelI     IHCDSGNCTIENVIWEDICEDAATN-NGK-TMTIVGGIAHNAKDGYGGKPDKVLQHNSKN 232
FsoPelB     VHC-KGTCTLNNVWWADVCEDAATFKQKSGTSTINGGGAFSAQ------DKVLQFNGRG 142
            :*  :  : ** **  *:  *** *        . .* ** **  :      *::* *  .

BliYvpA     TFTVKN--FTAD-QGGKFIRDLGGSTFK---AVVNIDNCTITNMKEAIFRTD------SS 190
BsuPelC     TFTVKN--FTAD-NGGKFIRDLGGSTFH---VDVIIDKCTITNMKEAIFRTD------SK 189
BspP2850    TFTVKN--FTAD-QGGKFIRDLGGSTFK---AVVNIDNCTITNMKEAIFRTD------SS 190
PamPelA     TINIKN--FRAD-DIGKLVRDNGGTTFT---VNMTLDNSNISNVKDAIMRTD------SS 188
PbaPelA     TINIKN--FRAD-DIGKLVRDNGGTSYA---VNMTLDNSNISNVKDSIMRTD------SS 188
BspKSM15    TINIRN--FRAD-DIGKLVRDNGGTTYK---VVMNVENCNISRVKDAILRTD------SS 190
EcaPel3     SHTIVQGKFTLTGQHGKLWRSCGDCTNNGGPRNLTIISATVNGTIDSIAGVNRNFGDVAE 295
EchPelI     STTVVKGNFTLTGEHGKLWRSCGDCSNNGGPRFLTVTSATVNGTIDSIAGVNRNYGDVAT 292
FsoPelB     TLNVND--FYVQ-DYGKLVRNCGNCEGNGGPRNINIKG-VVAKNGGELCGVNHNYGDVCT 198
            : .:     *    :     : **:  *. *.         ::    :       :

BspP2850    TSSVTMINTRYSK--VGQKWIGVK--HVTERNWHEF-------------- 222
BsuPelC     TSTVRMTNTRYSN--VGQKWIGVQ--HIYENNWTQF-------------- 221
BspP2850    TSSVTMINTRYSK--VGQKWIGVK--HVTERNWHEF-------------- 222
PamPelA     SSQGRITNTRYSK--VPTLFKGFASGKTSQSGWTQY-------------- 222
PbaPelA     VSQGKITNTRYSK--VPTLFKGFASGKTSQSGWTQY-------------- 222
BspKSM15    TSTGRIVNTRYSN--VPTLFKGFKSGNTTASGWTQY-------------- 224
EcaPel3     IRDLRIKGYKEGKPPVCEEFNGVEKGKGKSDKYGEFWDTKNCKVSRSNVKPL 347
EchPelI     ISGLKIKNYKEGKPPVCEEFKGVVKGQGSTEKYGEKWDTTNCKVSRSGVSKL 344
FsoPelB     ITDSCQNKGKSCQAYTGNDQKKEPPKFGPAGDNGKSCLVKSLRTNC----- 244
             :    :                                  :
```

Figure 4

```
TmaPelA    MLMRFSRVVSLVLLLVFTAVLTGAVKASLNDKPVGFASVPTADLPEGTVG  50
BsuBS2     --MK---KMLLMLAVCLCMIPADVYAADLGRQTLGTNDG-WGAASGGTTG  44
BamPel     --MK---KMLLMLAVCLCMIPADVYAADLGRQTLGTNDG-WGAASGGTTG  44
BspYA14    --MK---KVMLATALFLGLTPAGANAADLGHQTLGSNDG-WGAYSTGTTG  44
BsuPel     --MK---KVMLATALFLGLTPAGANAADLGHQTLGSNDG-WGAYSTGTTG  44
BliPel     --MKRFFSVIILGALLLLGTSAPIEAADYGRDVLGSKDG-WGAYGKGTTG  47
PamPelB    --MKKTVRSLCSTALALTLGFT-LLSGPASVQAAGNADYNLAGFSQGNTG  47
                :  :               .  .  *  .          *..*

TmaPelA    G----LGGEIVFVRTAEELEKYTTAEGK------------YVIVVDGTIVFE  86
BsuBS2     G----AKASSSNVYTVSNRQQLVSALGG------SANSTPKIIYIQGTTNMN  86
BamPel     G----AKASSSNVYTVSNRQQLVSALGG------SANSTPKIIYIQGTTNMN  86
BspYA14    G----SKASSSNVYTVSNRNQLVSALGK------ETNTTPKIIYIKGTIDMN  86
BsuPel     G----SKASSSNVYTVSNRNQLVSALGK------ETNTTPKIIYIKGTIDMN  86
BliPel     G----ADASSDQVYTVKNRKQLVEALGGDNKKNSENDTPKIIYVKGTINLS  94
PamPelB    GGIISESNTSTYKKVYNATDLALALKK-------NSGVKVMELMNDLDLG  90
           *       ..        .  :   .  :              ::  :  .  .  :  :

TmaPelA    --------IKVLSDKTIVGIN-DAKIVGGGLVIKD-AQNVIIRNIHFEGFY  131
BsuBS2     NQKARVVIDIPSNTTIIGSGSNAKVTGGSFNIKNGVDNVIVRNIEFQDAY  186
BamPel     NQKARVVIDIPSNTTIIGSGSNAKVTGGSFNIKNGVDNVIVRNIEFQDAY  186
BspYA14    NQKARVMVDIPANTTIVGSGTNAKVVGGNFQIKS--DNVIIRNIEFQDAY  184
BsuPel     NQKARVMVDIPANTTIVGSGTNAKVVGGNFQIKS--DNVIIRNIEFQDAY  184
BliPel     NQKERVLIRVGSNTTIIGLGDDAKIVGGGLYVKN-AENVIIRNIEFENAY  193
PamPelB    TGVSKITVDGFNGLTIFSAN-GSKIKHAAITVKR-SSNVIIRNLEFDELW  165
                      :     .  *:..     ..:*   .  :  :*   .*::**:.*:   :
                                              ©
TmaPelA    --------MEDDPRGK-KYDFDYINVENSHHIWIDHCTFVNGN-------  165
BsuBS2     DYFPQWDPTDGSSGNW-NSEYDNITINGATHIWIDHCTFNDGSNPDSGFP  235
BamPel     DYFPQWDPTDGSSGNW-NSEYDNITINGATHIWIDHCTFNDGSNPDSGFP  235
BspYA14    DYFPQWDPTDGSSGNW-NSQYDNITINGGTHIWIDHCTFNDGSRPDSTSP  233
BsuPel     DYFPQWDPTDGSSGNW-NSQYDNITINGGTHIWIDHCTFNDGSRPDSTSP  233
BliPel     DFFPGWDPTDGSSGNW-NSEYDNLLIEMSKNIWIDHCSFNDGDQPDELTE  242
PamPelB    EW------DESTKGDYDKNDWDYITLEDSSGVWIDHCTFNKAY-------  202
              :.           :  ::* :    :   . .:****:*  ..

©   ©
TmaPelA    ----------DGAVDIKKYSNYFTVSWCKFVDHDKVSLVGSSDKEDPEQA  205
BsuBS2     YYYGRKYQHHDGQTDIANGANYITLSYNKYHDHDRGSVIGNSDSKTSDEG  285
BamPel     YYYGRKYQHHDGQTDIANGANYITLSYNKYHDHDRGSVIGNSDSKTSDEG  285
BspYA14    KYYGRKYQHHDGQTDASNGANYITMSYNYYHDHDKSSIFGSSDKTSDDG  283
BsuPel     KYYGRKYQHHDGQTDASNGANYITMSYNYYHDHDKSSIFGSSDKTSDDG  283
BliPel     THFGREFQHHDGLLDIKKQSDFITVSYSIFSGHSKNTIIGSSDSYKADNG  292
PamPelB    ----------DGLVDSKKGTSGVTISWSTFKGDD-----GSANSWVTRQI  237
                    **   *     : :..:*:*        :  ...      *.::  .   .

TmaPelA    GQAYKVTYHHNYFKNCIQRMPRIRFGMAHVFNNFYSMGLRTGVSGNVFPI  255
BsuBS2     --KLKVTIHHNYYQNIVQRAPRVRYGQVHIYNNFYAG---SKS-AAYPFS  329
BamPel     --KLKVTIHHNYYQNIVQRAPRVRYGQVHIYNNFYAG---SKS-AAYPFS  329
BspYA14    --KLKITLHHNYRYKNIVQRAPRVRFGQVHVYNNYYEG---STSSSSYPFS  328
BsuPel     --KLKITLHHNYRYKNIVQRAPRVRFGQVHVYNNYYEG---STSSSSYPFS  328
BliPel     --HLRVTFHHNLYENIKERAPRVRYGKVHIYNNYFKS---TKD----SYN  333
PamPelB    NELEANKASYPMYNYLRSSAVGLSKQDVIAISGPQKKGHLVGATSLESAN  287
                 . :   ::     .  :        :   ..
```

Figure 5

PelA (SEQ ID NO:1)
ATGAAAAAAATGTTAACGCTATTGTTGTCCGCCGGTCTGGTCGCTTCCATATTTGGTGTTATGCCTGCAGCGGCTGCGCCAACGGTTG
TAAACTCAACGATTGTTGTACCTAAGGGCACGACGTATGATGGACAGGGGAAAACCTTTGTGGCGAATCCTTCTACCTTGGGTGACGG
TTCTCAAGCGGAGAATCAGAAGCCGGTCTTCCGGTTGGAAGCAGGCGCTACACTGAAAAATGTCATCATTGGTGCTCCAGCGGCAGAC
GGTGTGCATTGTTATGGTAACTGTAATATCTCTAATGTGGTATGGCAGGATGTGGGCGAGGATGCGTTGACACTGAAATCATCTGGAA
CGGTTAATATTACTGGTGGTGCAGCATATAAAGCGTACGATAAGGTATTCCAGATCAATGCAGCAGGCACAATTAACATTAAAAACTT
CCGTGCCGATGATATCGGCAAGCTGGTGCGGCAAAATGGAGGCACAACATTCACGGTCAACATGACTCTTGATAATTCCAATATTTCG
AATGTAAAAGATGCCATTATGCGTACAGACAGTAGCAGTTCACAAGGGCGAATTACGAATACACGTTATTCCAAAGTGCCAACACTAT
TCAAAGGATTTGCTTCGGGTAAAACGAGCCAGTCCGGTAATACGCAGTATTAA (SEQ ID NO:2)
MKKMLTLLLSAGLVASIFGVMPAAAAPTVVNSTIVVPKGTTYDGQGKTFVANPSTLGDGSQAENQKPVFRLEAGATLKNVIIGAPAAD
GVHCYGNCNISNVVWQDVGEDALTLKSSGTVNITGGAAYKAYDKVFQINAAGTINIKNFRADDIGKLVRQNGGTTFTVNMTLDNSNIS
NVKDAIMRTDSSSSQGRITNTRYSKVPTLFKGFASGKTSQSGNTQY*

PelB (SEQ ID NO:3)
ATGAAAAAAACAGTACGAAGTTTATGCAGCACGGCTCTGGCTCTCACGCTAGGGTTCACCTTATTATCCGGACCTGCAAGTGTGCAGG
CAGCGGGCAATGCAGATTACAATCTGGCCGGTTTCTCCCAAGGGAACACAGGTGGCGGAATCATCAGTGAGTCGAACACGTCCACGTA
TAAAAAAGTGTATAATGCCACCGACCTGGCGCTGGCTCTGAAAAAGAACTCCGGTGTCAAAGTCGTTGAGATTATGAACGACCTCGAC
TTAGGGTGGAACGAGATTCCTAGCGCGGCACAGACTTCACCTTTTGCGAAGCATAACGATGCACTGACACATCCGGTATTGAAGCAGA
CGGGGGGTCAGCAAAATTACGGTGGACGGCTTTAATGGACTCACCATTTTCTCGGCGAATGGCTCCAAGATCAAACACGCTGCCATCAC
GGTGAAACGAAGCTCCAATGTGATCATTCGCAACCTGGAATTCGATGAGCTGTGGGAGTGGGATGAATCCACCAAAGGGGACTATGAC
AAAAACGACTGGGACTACATTACCCTGGAGGACAGCAGCGGTGTGTGGATCGATCACTGCACGTTTAACAAAGCGTATGACGGACTCG
TCGATTCGAAAAAAGGAACCAGCGGTGTAACCATCTCCTGGTCTACCTTCAAAGGGGATGACGGCAGTGCGAACAGCTGGGTCACCCG
CCAGATCAATGAACTGGAAGCAAACAAAGCTTCCTATCCCATGTATAACTACTTGCGAAGCAGTGCGGTCGGTCTAAGTAAACAAGAC
GTCATTGCCATCTCCGGCCCGCAGAAAAAGGGGCACCTCGTCGGTGCGACCAGTCTGGAGTCGGCTAACGCTAATTTGTCGATCACCC
TGCATCATAACCTGTATAAAGACATCCAGGATCGCATGCCTCGTCTGCGTGGCGGTAATGCCCATGCCTATAACATCATCATGGATGC
TGCCGATGCCCGTTCAGCTCAGTCACGTATTACTAGCGCTATGGCAACAGCCATCGCTTCCAAAGGTTACAAATTCGGTATTACCAGC
AATGGAGCTATCTCCACCGAAAGTGGCGCTGTGCTGGTCGAAAAATCAGTAATCAAGGATGTGCAGTACCCTGTACGCAACAATCAG
ACAGATCCGACCAACGCCACGTACACCGGTAA (SEQ ID NO:4)
MKKTVRSLCSTALALTLGFTLLSGPASVQAAGNADYNLAGFSQGNTGGGIISESNTSTYKKVYNATDLALALKKNSGVKV
VEIMNDLDLGWNEIPSAAQTSPFAKHNDALTHPVLKQTGVSKITVDGFNGLTIFSANGSKIKHAAITVKRSSNVIIRNLE
FDELWEWDESTKGDYDKNDWDYITLEDSSGVWIDHCTFNKAYDGLVDSKKGTSGVTISWSTFKGDDGSANSWVTRQINEL
EANKASYPMYNYLRSSAVGLSKQDVIAISGPQKKGHLVGATSLESANANLSITLHHNLYKDIQDRMPRLRGGNAHAYNII
MDAADARSAQSRITSAMATAIASKGYKFGITSNGAISTESGAVLVEKSVIKDVQXPCTQQSDRSDQRHVHR*

Og1 (SEQ ID NO:5)
ATGGCCAAAGGTAAAAAGCTTTCTTTTTCGTTCCATACTTACCAGGATTCAGTCACCGGCACCGAAGTGGTGCGTCTCACTCCTCCCG
ATGTTATCTGCCACCGCAACTACTTCTATCAGAAGTGTTTTTCAGTGATGGCAGCAAGCTGCTTTTTTGGTGGCGCCTTTGACGGGCC
GTGGAACTACTATTTGCTGGATCTGAAAACTCAGCAGGCGACGCAACTGACCGAAGGTACCGGCGACAATACTTTTGGTGGTTTTCTG
TCACCAGATGATGACGCGCTTTATTATGTAAAGAACGTTCGTAATTTGATGCGTGTTGACCTGAATACACTGGAAGAAACCAATAT
TTATCAGGTGCCGGACGACTGGGTCGGGTACGGTACCTGGGTTGCCAACTCCGACTGCACCAAAATGGTCGGTATCGAGATCAAGAAA
GAGGATTGGAAACCACTGACCGACTGGAAAAAATTCCAGGAATTCTACTTTACCAATCCATGCTGCCGTTTGATTCGTATCGATCTGA
AAACCGGCGAAGCCACCACCATTCTGAAGGAAAAACCAATGGCTGGGTCATCGTATTTACCGTCCGGGTGACGATAATACGGTGGCCTT
CTGCCATGAAGGTCCGCATGACCTGGTTGATGCGCGTATGTGGTTCATCAATGAAGATGGCTCCAATATGCGTAAGGTAAAAGAGC
ATGCCGCCGGGCGAAAGCTGCACTCACGAATTCTGGGTGCCGAATGGTTCTGCGCTGGCCTACGTTTCCTATCTGAAAGGCAGTACTAA
CCGTTTCATTTGCAGCGTTGATCCGGTAACGCTGGAAAACCGTCAGTTGACTGAAATGCCGCCGTGTTCTCACCTGATGAGTAACTAC
GATGGTACGTTGATGGTGGGAGATGGGTGTAATGCGCCGGTGGATGTGAAAGATGACGGTGGCTACAAGACTGAAAACGATCCGTTCC
TGTATGTGTTCAATATGAAGACCGGGAAACATTTCCAGGTCGCTCAACACAACACCTCCTGGGAAGTGCTGGAGGGCGATCGTCAG
GTAACGCATCCACATCCGTCCTTTACGCCGGATGACAAGCACATTCTGTTTACGTCTGATGTCGATGGTAAGCCGGCGTTATATCTGG
CAAAAGTGCCTGATTCCGTCTGGCAATAA (SEQ ID NO:6)
MAKGKKLSFSFHTYQDSVTGTEVVRLTPPDVICHRNYFYQKCFSNDGSKLLFGGAFDGPWNYYLLDLKTQQATQLTEGTGDNTFGGFL
SPDDDALYYVKNVRNLMRVDLNTLEETNIYQVPDDWVGYGTWVANSDCTKMVGIEIKKEDWKPLTDWKKFQEFYFTNPCCRLIRIDLK
TGEATTILKENQWLGHPIYRPGDDNTVAFCHEGPHDLVDARMWFINEDGSNMRKVKEHAPGESCTHEFWVPNGSALAYVSYLKGSTNR
FICSVDPVTLENRQLTEMPPCSHLMSNYDGTLMVGDGCNAPVDVKDDGGYKTENDPFLYVFNMKTGKHFQVAQHNTSWEVLEGDRQ
VTHPHPSFTPDDKHILFTSDVDGKPALYLAKVPDSVWQ

Figure 12

SEQUENCE LISTING

```
<160> NUMBER OF SEQ ID NOS: 50

<210> SEQ ID NO 1
<211> LENGTH: 669
<212> TYPE: DNA
<213> ORGANISM: P. amylolyticus

<400> SEQUENCE: 1
atgaaaaaaa tgttaacgct attgttgtcc gccggtctgg tcgcttccat atttggtgtt      60
atgcctgcag cggctgcgcc aacggttgta aactcaacga ttgttgtacc taagggcacg     120
acgtatgatg gacaggggaa aacctttgtg gcgaatcctt ctaccttggg tgacggttct     180
caagcggaga atcagaagcc ggtcttccgg ttggaagcag gcgctacact gaaaaatgtc     240
atcattggtg ctccagcggc agacggtgtg cattgttatg gtaactgtaa tatctctaat     300
gtggtatggc aggatgtggg cgaggatgcg ttgacactga atcatctgg aacggttaat     360 attactggtg gtgcagcata taaagcgtac gataaggtat tccagatcaa tgcagcaggc     420
acaattaaca ttaaaaactt ccgtgccgat gatatcggca agctggtgcg gcaaaatgga     480
ggcacaacat tcacggtcaa catgactctt gataattcca atatttcgaa tgtaaaagat     540
gccattatgc gtacagacag tagcagttca caagggcgaa ttacgaatac acgttattcc     600
aaagtgccaa cactattcaa aggatttgct tcgggtaaaa cgagccagtc cggtaatacg     660
cagtattaa                                                            669

<210> SEQ ID NO 2
<211> LENGTH: 222
<212> TYPE: PRT
<213> ORGANISM: P. amylolyticus

<400> SEQUENCE: 2

Met Lys Lys Met Leu Thr Leu Leu Leu Ser Ala Gly Leu Val Ala Ser
1               5                   10                  15

Ile Phe Gly Val Met Pro Ala Ala Ala Ala Pro Thr Val Val Asn Ser
                20                  25                  30

Thr Ile Val Val Pro Lys Gly Thr Thr Tyr Asp Gly Gln Gly Lys Thr
            35                  40                  45

Phe Val Ala Asn Pro Ser Thr Leu Gly Asp Gly Ser Gln Ala Glu Asn
        50                  55                  60

Gln Lys Pro Val Phe Arg Leu Glu Ala Gly Ala Thr Leu Lys Asn Val
65                  70                  75                  80

Ile Ile Gly Ala Pro Ala Ala Asp Gly Val His Cys Tyr Gly Asn Cys
                85                  90                  95

Asn Ile Ser Asn Val Val Trp Gln Asp Val Gly Glu Asp Ala Leu Thr
                100                 105                 110

Leu Lys Ser Ser Gly Thr Val Asn Ile Thr Gly Gly Ala Ala Tyr Lys
            115                 120                 125
```

```
Ala Tyr Asp Lys Val Phe Gln Ile Asn Ala Ala Gly Thr Ile Asn Ile
        130                 135                 140

Lys Asn Phe Arg Ala Asp Asp Ile Gly Lys Leu Val Arg Gln Asn Gly
145                 150                 155                 160

Gly Thr Thr Phe Thr Val Asn Met Thr Leu Asp Asn Ser Asn Ile Ser
                165                 170                 175

Asn Val Lys Asp Ala Ile Met Arg Thr Asp Ser Ser Ser Gln Gly
            180                 185                 190

Arg Ile Thr Asn Thr Arg Tyr Ser Lys Val Pro Thr Leu Phe Lys Gly
        195                 200                 205

Phe Ala Ser Gly Lys Thr Ser Gln Ser Gly Asn Thr Gln Tyr
    210                 215                 220

<210> SEQ ID NO 3
<211> LENGTH: 1176
<212> TYPE: DNA
<213> ORGANISM: P. amylolyticus
<220> FEATURE:
<221> NAME/KEY: misc_feature
<222> LOCATION: (1125)..(1125)
<223> OTHER INFORMATION: n is a, c, g, or t

<400> SEQUENCE: 3
atgaaaaaaa cagtacgaag tttatgcagc acggctctgg ctctcacgct agggttcacc      60
ttattatccg gacctgcaag tgtgcaggca gcgggcaatg cagattacaa tctggccggt     120
ttctcccaag ggaacacagg tggcggaatc atcagtgagt cgaacacgtc cacgtataaa     180
aaagtgtata atgccaccga cctggcgctg gctctgaaaa agaactccgg tgtcaaagtc     240
gttgagatta tgaacgacct cgacttaggg tggaacgaga ttcctagcgc ggcacagact     300
tcaccttttg cgaagcataa cgatgcactg acacatccgg tattgaagca gacggggtc      360
agcaaaatta cggtggacgg ctttaatgga ctcaccattt tctcggcgaa tggctccaag     420
atcaaacacg ctgccatcac ggtgaaacga agctccaatg tgatcattcg caacctggaa     480
ttcgatgagc tgtgggagtg ggatgaatcc accaaagggg actatgacaa aaacgactgg     540
gactacatta ccctggagga cagcagcggt gtgtggatcg atcactgcac gtttaacaaa     600
gcgtatgacg gactcgtcga ttcgaaaaaa ggaaccagcg gtgtaaccat ctcctggtct     660
accttcaaag gggatgacgg cagtgcgaac agctgggtca cccgccagat caatgaactg     720
gaagcaaaca aagcttccta tcccatgtat aactacttgc gaagcagtgc ggtcggtcta     780
agtaaacaag acgtcattgc catctccggc ccgcagaaaa aggggcacct cgtcggtgcg     840
accagtctgg agtcggctaa cgctaatttg tcgatcaccc tgcatcataa cctgtataaa     900
gacatccagg atcgcatgcc tcgtctgcgt ggcggtaatg cccatgccta aacatcatc     960
atggatgctg ccgatgcccg ttcagctcag tcacgtatta ctagcgctat ggcaacagcc    1020
atcgcttcca aaggttacaa attcggtatt accagcaatg gagctatctc caccgaaagt    1080
ggcgctgtgc tggtcgaaaa atcagtaatc aaggatgtgc agtanccctg tacgcaacaa    1140
tcagacagat ccgaccaacg ccacgtacac cggtaa                              1176

<210> SEQ ID NO 4
<211> LENGTH: 391
<212> TYPE: PRT
<213> ORGANISM: P. amylolyticus
<220> FEATURE:
<221> NAME/KEY: misc_feature
<222> LOCATION: (375)..(375)
```

-continued

<223> OTHER INFORMATION: Xaa can be any naturally occurring amino acid

<400> SEQUENCE: 4

```
Met Lys Lys Thr Val Arg Ser Leu Cys Ser Thr Ala Leu Ala Leu Thr
1               5                   10                  15

Leu Gly Phe Thr Leu Leu Ser Gly Pro Ala Ser Val Gln Ala Ala Gly
            20                  25                  30

Asn Ala Asp Tyr Asn Leu Ala Gly Phe Ser Gln Gly Asn Thr Gly Gly
        35                  40                  45

Gly Ile Ile Ser Glu Ser Asn Thr Ser Thr Tyr Lys Lys Val Tyr Asn
50                  55                  60

Ala Thr Asp Leu Ala Leu Ala Leu Lys Lys Asn Ser Gly Val Lys Val
65                  70                  75                  80

Val Glu Ile Met Asn Asp Leu Asp Leu Gly Trp Asn Glu Ile Pro Ser
                85                  90                  95

Ala Ala Gln Thr Ser Pro Phe Ala Lys His Asn Asp Ala Leu Thr His
            100                 105                 110

Pro Val Leu Lys Gln Thr Gly Val Ser Lys Ile Thr Val Asp Gly Phe
        115                 120                 125

Asn Gly Leu Thr Ile Phe Ser Ala Asn Gly Ser Lys Ile Lys His Ala
130                 135                 140

Ala Ile Thr Val Lys Arg Ser Ser Asn Val Ile Ile Arg Asn Leu Glu
145                 150                 155                 160

Phe Asp Glu Leu Trp Glu Trp Asp Glu Ser Thr Lys Gly Asp Tyr Asp
                165                 170                 175

Lys Asn Asp Trp Asp Tyr Ile Thr Leu Glu Asp Ser Ser Gly Val Trp
            180                 185                 190

Ile Asp His Cys Thr Phe Asn Lys Ala Tyr Asp Gly Leu Val Asp Ser
        195                 200                 205

Lys Lys Gly Thr Ser Gly Val Thr Ile Ser Trp Ser Thr Phe Lys Gly
210                 215                 220

Asp Asp Gly Ser Ala Asn Ser Trp Val Thr Arg Gln Ile Asn Glu Leu
225                 230                 235                 240

Glu Ala Asn Lys Ala Ser Tyr Pro Met Tyr Asn Tyr Leu Arg Ser Ser
                245                 250                 255

Ala Val Gly Leu Ser Lys Gln Asp Val Ile Ala Ile Ser Gly Pro Gln
            260                 265                 270

Lys Lys Gly His Leu Val Gly Ala Thr Ser Leu Glu Ser Ala Asn Ala
        275                 280                 285

Asn Leu Ser Ile Thr Leu His His Asn Leu Tyr Lys Asp Ile Gln Asp
290                 295                 300

Arg Met Pro Arg Leu Arg Gly Gly Asn Ala His Ala Tyr Asn Ile Ile
305                 310                 315                 320

Met Asp Ala Ala Asp Ala Arg Ser Ala Gln Ser Arg Ile Thr Ser Ala
                325                 330                 335

Met Ala Thr Ala Ile Ala Ser Lys Gly Tyr Lys Phe Gly Ile Thr Ser
            340                 345                 350

Asn Gly Ala Ile Ser Thr Glu Ser Gly Ala Val Leu Val Glu Lys Ser
        355                 360                 365

Val Ile Lys Asp Val Gln Xaa Pro Cys Thr Gln Gln Ser Asp Arg Ser
370                 375                 380

Asp Gln Arg His Val His Arg
385                 390
```

<210> SEQ ID NO 5
<211> LENGTH: 1167
<212> TYPE: DNA
<213> ORGANISM: E. chrysanthemi

<400> SEQUENCE: 5

```
atggccaaag gtaaaaagct ttcttttcg ttccatactt accaggattc agtcaccggc      60
accgaagtgg tgcgtctcac tcctcccgat gttatctgcc accgcaacta cttctatcag     120
aagtgttttt ccaatgatgg cagcaagctg ctttttggtg gcgcctttga cgggccgtgg     180
aactactatt tgctggatct gaaaactcag caggcgacgc aactgaccga aggtaccggc     240
gacaatactt ttggtggttt tctgtcacca gatgatgacg cgctttatta tgtaaagaac     300
gttcgtaatt tgatgcgtgt tgacctgaat acactggaag aaaccaatat ttatcaggtg     360
ccggacgact gggtcgggta cggtacctgg gttgccaact ccgactgcac caaaatggtc     420
ggtatcgaga tcaagaaaga ggattggaaa ccactgaccg actggaaaaa attccaggaa     480
ttctacttta ccaatccatg ctgccgtttg attcgtatcg atctgaaaac cggcgaagcc     540
accaccattc tgaaggaaaa ccaatggctg ggtcatccta tttaccgtcc gggtgacgat     600
aatacggtgg ccttctgcca tgaaggtccg catgacctgg ttgatgcgcg tatgtggttc     660
atcaatgaag atggctccaa tatgcgtaag gtaaaagagc atgcgccggg cgaaagctgc     720
actcacgaat tctgggtgcc gaatggttct gcgctggcct acgtttccta tctgaaaggc     780
agtactaacc gtttcatttg cagcgttgat ccggtaacgc tggaaaaccg tcagttgact     840
gaaatgccgc cgtgttctca cctgatgagt aactacgatg gtacgttgat ggtgggagat     900
gggtgtaatg cgccggtgga tgtgaaagat gacggtggct acaagactga aaacgatccg     960
ttcctgtatg tgttcaatat gaagaccggg aaacatttcc aggtcgctca cacaacaccc    1020
tcctgggaag tgctggaggg cgatcgtcag gtaacgcatc cacatccgtc ctttacgccg    1080
gatgacaagc acattctgtt tacgtctgat gtcgatggta agccggcgtt atatctggca    1140
aaagtgcctg attccgtctg gcaataa                                         1167
```

<210> SEQ ID NO 6
<211> LENGTH: 388
<212> TYPE: PRT
<213> ORGANISM: E. chrysanthemi

<400> SEQUENCE: 6

```
Met Ala Lys Gly Lys Lys Leu Ser Phe Ser Phe His Thr Tyr Gln Asp
1               5                   10                  15

Ser Val Thr Gly Thr Glu Val Val Arg Leu Thr Pro Pro Asp Val Ile
            20                  25                  30

Cys His Arg Asn Tyr Phe Tyr Gln Lys Cys Phe Ser Asn Asp Gly Ser
        35                  40                  45

Lys Leu Leu Phe Gly Gly Ala Phe Asp Gly Pro Trp Asn Tyr Tyr Leu
    50                  55                  60

Leu Asp Leu Lys Thr Gln Gln Ala Thr Gln Leu Thr Glu Gly Thr Gly
65                  70                  75                  80

Asp Asn Thr Phe Gly Gly Phe Leu Ser Pro Asp Asp Ala Leu Tyr
            85                  90                  95

Tyr Val Lys Asn Val Arg Asn Leu Met Arg Val Asp Leu Asn Thr Leu
            100                 105                 110

Glu Glu Thr Asn Ile Tyr Gln Val Pro Asp Asp Trp Val Gly Tyr Gly
            115                 120                 125
```

-continued

Thr Trp Val Ala Asn Ser Asp Cys Thr Lys Met Val Gly Ile Glu Ile
     130                 135                 140

Lys Lys Glu Asp Trp Lys Pro Leu Thr Asp Trp Lys Lys Phe Gln Glu
145                 150                 155                 160

Phe Tyr Phe Thr Asn Pro Cys Cys Arg Leu Ile Arg Ile Asp Leu Lys
             165                 170                 175

Thr Gly Glu Ala Thr Thr Ile Leu Lys Glu Asn Gln Trp Leu Gly His
         180                 185                 190

Pro Ile Tyr Arg Pro Gly Asp Asp Asn Thr Val Ala Phe Cys His Glu
     195                 200                 205

Gly Pro His Asp Leu Val Asp Ala Arg Met Trp Phe Ile Asn Glu Asp
210                 215                 220

Gly Ser Asn Met Arg Lys Val Lys Glu His Ala Pro Gly Glu Ser Cys
225                 230                 235                 240

Thr His Glu Phe Trp Val Pro Asn Gly Ser Ala Leu Ala Tyr Val Ser
             245                 250                 255

Tyr Leu Lys Gly Ser Thr Asn Arg Phe Ile Cys Ser Val Asp Pro Val
         260                 265                 270

Thr Leu Glu Asn Arg Gln Leu Thr Glu Met Pro Pro Cys Ser His Leu
     275                 280                 285

Met Ser Asn Tyr Asp Gly Thr Leu Met Val Gly Asp Gly Cys Asn Ala
290                 295                 300

Pro Val Asp Val Lys Asp Gly Gly Tyr Lys Thr Glu Asn Asp Pro
305                 310                 315                 320

Phe Leu Tyr Val Phe Asn Met Lys Thr Gly Lys His Phe Gln Val Ala
             325                 330                 335

Gln His Asn Thr Ser Trp Glu Val Leu Glu Gly Asp Arg Gln Val Thr
         340                 345                 350

His Pro His Pro Ser Phe Thr Pro Asp Asp Lys His Ile Leu Phe Thr
     355                 360                 365

Ser Asp Val Asp Gly Lys Pro Ala Leu Tyr Leu Ala Lys Val Pro Asp
370                 375                 380

Ser Val Trp Gln
385

<210> SEQ ID NO 7
<211> LENGTH: 26
<212> TYPE: DNA
<213> ORGANISM: artificial
<220> FEATURE:
<223> OTHER INFORMATION: synthetic oligonucleotide primer

<400> SEQUENCE: 7
gagatcttaa ggaaaaacag catgga                                          26

<210> SEQ ID NO 8
<211> LENGTH: 18
<212> TYPE: DNA
<213> ORGANISM: artificial
<220> FEATURE:
<223> OTHER INFORMATION: synthetic oligonucleotide primer

<400> SEQUENCE: 8
atagccggcg tccagaat                                                   18

<210> SEQ ID NO 9
<211> LENGTH: 34

```
<212> TYPE: DNA
<213> ORGANISM: artificial
<220> FEATURE:
<223> OTHER INFORMATION: synthetic oligonucleotide primer

<400> SEQUENCE: 9
ttgctcttcc atgtactatt taaaaaacac aaac                              34

<210> SEQ ID NO 10
<211> LENGTH: 33
<212> TYPE: DNA
<213> ORGANISM: artificial
<220> FEATURE:
<223> OTHER INFORMATION: synthetic oligonucleotide primer

<400> SEQUENCE: 10
ttgctcttcg ttaagcgact tcattcacct gac                               33

<210> SEQ ID NO 11
<211> LENGTH: 34
<212> TYPE: DNA
<213> ORGANISM: artificial
<220> FEATURE:
<223> OTHER INFORMATION: synthetic oligonucleotide primer

<400> SEQUENCE: 11
ttgctcttcc atgccaatga ccgaagaata agag                              34

<210> SEQ ID NO 12
<211> LENGTH: 34
<212> TYPE: DNA
<213> ORGANISM: artificial
<220> FEATURE:
<223> OTHER INFORMATION: synthetic oligonucleotide primer

<400> SEQUENCE: 12
ttgctcttcg ttaaactgac gattcaactt tata                              34

<210> SEQ ID NO 13
<211> LENGTH: 20
<212> TYPE: DNA
<213> ORGANISM: artificial
<220> FEATURE:
<223> OTHER INFORMATION: synthetic oligonucleotide primer

<400> SEQUENCE: 13
ggtgaagtgc ctctggatgt                                              20

<210> SEQ ID NO 14
<211> LENGTH: 20
<212> TYPE: DNA
<213> ORGANISM: artificial
<220> FEATURE:
<223> OTHER INFORMATION: synthetic oligonucleotide primer

<400> SEQUENCE: 14
cgcctacccg agtgagaata                                              20

<210> SEQ ID NO 15
<211> LENGTH: 20
<212> TYPE: DNA
<213> ORGANISM: artificial
<220> FEATURE:
<223> OTHER INFORMATION: synthetic oligonucleotide primer

<400> SEQUENCE: 15
```

-continued

```
gcaaagcgga agtctaccag                                              20

<210> SEQ ID NO 16
<211> LENGTH: 20
<212> TYPE: DNA
<213> ORGANISM: artificial
<220> FEATURE:
<223> OTHER INFORMATION: synthetic oligonucleotide primer

<400> SEQUENCE: 16
atgccttcgg tgattaaacg                                              20

<210> SEQ ID NO 17
<211> LENGTH: 33
<212> TYPE: DNA
<213> ORGANISM: artificial
<220> FEATURE:
<223> OTHER INFORMATION: synthetic oligonucleotide primer

<400> SEQUENCE: 17
ctagttgaca tgatagaagc actctactat att                               33

<210> SEQ ID NO 18
<211> LENGTH: 33
<212> TYPE: DNA
<213> ORGANISM: artificial
<220> FEATURE:
<223> OTHER INFORMATION: synthetic oligonucleotide primer

<400> SEQUENCE: 18
aactgtacta tcttcgtgag atgatataac tag                               33

<210> SEQ ID NO 19
<211> LENGTH: 22
<212> TYPE: DNA
<213> ORGANISM: artificial
<220> FEATURE:
<223> OTHER INFORMATION: synthetic oligonucleotide primer

<400> SEQUENCE: 19
tgctcaacgg gaatcctgct ct                                           22

<210> SEQ ID NO 20
<211> LENGTH: 34
<212> TYPE: DNA
<213> ORGANISM: artificial
<220> FEATURE:
<223> OTHER INFORMATION: synthetic oligonucleotide primer

<400> SEQUENCE: 20
gcgcatgggc cccacacagg aaacagctat gacc                              34

<210> SEQ ID NO 21
<211> LENGTH: 36
<212> TYPE: DNA
<213> ORGANISM: artificial
<220> FEATURE:
<223> OTHER INFORMATION: synthetic oligonucleotide primer

<400> SEQUENCE: 21
gcatgcgggc ccgttaccaa tgcttaatca gtgagg                            36

<210> SEQ ID NO 22
<211> LENGTH: 24
<212> TYPE: DNA
<213> ORGANISM: artificial
```

```
<220> FEATURE:
<223> OTHER INFORMATION: synthetic oligonucleotide primer

<400> SEQUENCE: 22
tcagcacgaa cacgaaccgt ctta                                          24

<210> SEQ ID NO 23
<211> LENGTH: 24
<212> TYPE: DNA
<213> ORGANISM: artificial
<220> FEATURE:
<223> OTHER INFORMATION: synthetic oligonucleotide primer

<400> SEQUENCE: 23
tgtgctgcaa ggcgattaag ttgg                                          24

<210> SEQ ID NO 24
<211> LENGTH: 24
<212> TYPE: DNA
<213> ORGANISM: artificial
<220> FEATURE:
<223> OTHER INFORMATION: synthetic oligonucleotide primer

<400> SEQUENCE: 24
acactgaacg aaatgctcca aacc                                          24

<210> SEQ ID NO 25
<211> LENGTH: 74
<212> TYPE: DNA
<213> ORGANISM: artificial
<220> FEATURE:
<223> OTHER INFORMATION: synthetic oligonucleotide primer

<400> SEQUENCE: 25
gtacagggcc cggatccttg acatgataga agcactctac tatattctag tgcttctacg   60
gttctgtggg acaa                                                     74

<210> SEQ ID NO 26
<211> LENGTH: 56
<212> TYPE: DNA
<213> ORGANISM: artificial
<220> FEATURE:
<223> OTHER INFORMATION: synthetic oligonucleotide primer

<400> SEQUENCE: 26
cgatcaagct tgggcccgag cggccgcctc gagtccacat ggtttggagc atttcg       56

<210> SEQ ID NO 27
<211> LENGTH: 66
<212> TYPE: DNA
<213> ORGANISM: artificial
<220> FEATURE:
<223> OTHER INFORMATION: synthetic oligonucleotide primer

<400> SEQUENCE: 27
gcagtgagct cttgacatga tagaagcact ctactatatt ctagttatac ttatcgggag   60
gaatcg                                                              66

<210> SEQ ID NO 28
<211> LENGTH: 33
<212> TYPE: DNA
<213> ORGANISM: artificial
<220> FEATURE:
<223> OTHER INFORMATION: synthetic oligonucleotide primer
```

```
<400> SEQUENCE: 28
catgggatcc cggagcgctt aacttagtaa ctc                                      33

<210> SEQ ID NO 29
<211> LENGTH: 24
<212> TYPE: DNA
<213> ORGANISM: artificial
<220> FEATURE:
<223> OTHER INFORMATION: synthetic oligonucleotide primer

<400> SEQUENCE: 29
accgcagcat cgcttatgta ggta                                               24

<210> SEQ ID NO 30
<211> LENGTH: 24
<212> TYPE: DNA
<213> ORGANISM: artificial
<220> FEATURE:
<223> OTHER INFORMATION: synthetic oligonucleotide primer

<400> SEQUENCE: 30
agtatcactg ttgccacgga agga                                               24

<210> SEQ ID NO 31
<211> LENGTH: 24
<212> TYPE: DNA
<213> ORGANISM: artificial
<220> FEATURE:
<223> OTHER INFORMATION: synthetic oligonucleotide primer

<400> SEQUENCE: 31
tggtgagtcc attaaagccg tcca                                               24

<210> SEQ ID NO 32
<211> LENGTH: 175
<212> TYPE: PRT
<213> ORGANISM: B. licheniformis

<400> SEQUENCE: 32
```

Lys Gly Lys Arg Leu Ile Ala Gly Pro Glu Leu Gly Asp Gly Ser Gln
1               5                   10                  15

Arg Glu Asp Gln Lys Pro Ile Phe Lys Val Glu Asp Gly Ala Thr Leu
            20                  25                  30

Lys Asn Val Val Leu Gly Ala Pro Ala Ala Asp Gly Val His Thr Tyr
        35                  40                  45

Gly Asn Ala Ser Ile Asn Asn Val Val Trp Glu Asp Val Gly Glu Asp
    50                  55                  60

Ala Leu Thr Val Lys Ser Glu Gly Ser Val Thr Ile Asn Gly Gly Ser
65                  70                  75                  80

Ala Arg Leu Ala Ala Asp Lys Ile Phe Gln Ile Asn Lys Ala Ser Thr
                85                  90                  95

Phe Thr Val Lys Asn Phe Thr Ala Asp Gln Gly Lys Phe Ile Arg
            100                 105                 110

Gln Leu Gly Gly Ser Thr Phe Lys Ala Val Val Asn Ile Asp Asn Cys
        115                 120                 125

Thr Ile Thr Asn Met Lys Glu Ala Ile Phe Arg Thr Asp Ser Ser Thr
    130                 135                 140

Ser Ser Val Thr Met Ile Asn Thr Arg Tyr Ser Lys Val Gly Gln Lys
145                 150                 155                 160

Trp Ile Gly Val Lys His Val Thr Glu Arg Asn Asn His Glu Phe

```
              165                 170                 175

<210> SEQ ID NO 33
<211> LENGTH: 175
<212> TYPE: PRT
<213> ORGANISM: B. subtilis

<400> SEQUENCE: 33

Lys Gly Gln Arg Phe Val Ala Gly Lys Glu Leu Gly Asp Gly Ser Gln
1               5                   10                  15

Ser Glu Asn Gln Asp Pro Val Phe Arg Val Glu Asp Gly Ala Thr Leu
            20                  25                  30

Lys Asn Val Val Leu Gly Ala Pro Ala Asp Gly Val His Thr Tyr
        35                  40                  45

Gly Asn Val Asn Ile Gln Asn Val Lys Trp Glu Asp Val Gly Glu Asp
    50                  55                  60

Ala Leu Thr Val Lys Lys Glu Gly Lys Val Thr Ile Asp Gly Gly Ser
65                  70                  75                  80

Ala Gln Lys Ala Ser Asp Lys Ile Phe Gln Ile Asn Lys Ala Ser Thr
                85                  90                  95

Phe Thr Val Lys Asn Phe Thr Ala Asp Asn Gly Gly Lys Phe Ile Arg
            100                 105                 110

Gln Leu Gly Gly Ser Thr Phe His Val Asp Val Ile Asp Lys Cys
        115                 120                 125

Thr Ile Thr Asn Met Lys Glu Ala Ile Phe Arg Thr Asp Ser Lys Thr
    130                 135                 140

Ser Thr Val Arg Met Thr Asn Thr Arg Tyr Ser Asn Val Gly Gln Lys
145                 150                 155                 160

Trp Ile Gly Val Gln His Ile Tyr Glu Asn Asn Asn Thr Gln Phe
                165                 170                 175

<210> SEQ ID NO 34
<211> LENGTH: 175
<212> TYPE: PRT
<213> ORGANISM: Bacillus sp. P-2850

<400> SEQUENCE: 34

Lys Gly Lys Arg Leu Ile Ala Gly Pro Glu Leu Gly Asp Gly Ser Gln
1               5                   10                  15

Arg Glu Asp Gln Lys Pro Ile Phe Lys Val Glu Asp Gly Ala Thr Leu
            20                  25                  30

Lys Asn Val Val Leu Gly Ala Pro Ala Asp Gly Val His Thr Tyr
        35                  40                  45

Gly Asn Ala Ser Ile Asn Asn Val Val Trp Glu Asp Val Gly Glu Asp
    50                  55                  60

Ala Leu Thr Val Lys Ser Glu Gly Ser Val Thr Ile Asn Gly Gly Ser
65                  70                  75                  80

Ala Arg Leu Ala Ala Asp Lys Ile Phe Gln Ile Asn Lys Ala Ser Thr
                85                  90                  95

Phe Thr Val Lys Asn Phe Thr Ala Asp Gln Gly Gly Lys Phe Ile Arg
            100                 105                 110

Gln Leu Gly Gly Ser Thr Phe Lys Ala Val Val Asn Ile Asp Asn Cys
        115                 120                 125

Thr Ile Thr Asn Met Lys Glu Ala Ile Phe Arg Thr Asp Ser Ser Thr
    130                 135                 140

Ser Ser Val Thr Met Ile Asn Thr Arg Tyr Ser Lys Val Gly Gln Lys
```

```
                145                 150                 155                 160
Trp Ile Gly Val Lys His Val Thr Glu Arg Asn Asn His Glu Phe
                165                 170                 175

<210> SEQ ID NO 35
<211> LENGTH: 178
<212> TYPE: PRT
<213> ORGANISM: P. amylolyticus

<400> SEQUENCE: 35

Gln Gly Lys Thr Phe Val Ala Asn Pro Ser Thr Leu Gly Asp Gly Ser
1               5                   10                  15

Gln Ala Glu Asn Gln Lys Pro Val Phe Arg Leu Glu Ala Gly Ala Thr
                20                  25                  30

Leu Lys Asn Val Ile Ile Gly Ala Pro Ala Ala Asp Gly Val His Cys
                35                  40                  45

Tyr Gly Asn Cys Asn Ile Ser Asn Val Val Trp Gln Asp Val Gly Glu
            50                  55                  60

Asp Ala Leu Thr Leu Lys Ser Ser Gly Thr Val Asn Ile Thr Gly Gly
65                  70                  75                  80

Ala Ala Tyr Lys Ala Tyr Asp Lys Val Phe Gln Ile Asn Ala Ala Gly
                85                  90                  95

Thr Ile Asn Ile Lys Asn Phe Arg Ala Asp Asp Ile Gly Lys Leu Val
                100                 105                 110

Arg Gln Asn Gly Gly Thr Thr Phe Thr Val Asn Met Thr Leu Asp Asn
                115                 120                 125

Ser Asn Ile Ser Asn Val Lys Asp Ala Ile Met Arg Thr Asp Ser Ser
            130                 135                 140

Ser Ser Gln Gly Arg Ile Thr Asn Thr Arg Tyr Ser Lys Val Pro Thr
145                 150                 155                 160

Leu Phe Lys Gly Phe Ala Ser Gly Lys Thr Ser Gln Ser Gly Asn Thr
                165                 170                 175

Gln Tyr

<210> SEQ ID NO 36
<211> LENGTH: 178
<212> TYPE: PRT
<213> ORGANISM: P. barcinonensis

<400> SEQUENCE: 36

Gln Gly Lys Thr Phe Val Ala Asn Pro Ser Thr Leu Gly Asp Gly Ser
1               5                   10                  15

Gln Ala Glu Asn Gln Lys Pro Val Phe Arg Leu Glu Ala Gly Ala Thr
                20                  25                  30

Leu Lys Asn Val Ile Ile Gly Ala Pro Ala Ala Asp Gly Val His Cys
                35                  40                  45

Tyr Gly Ser Cys Asn Ile Ser Asn Val Val Trp Glu Asp Val Gly Glu
            50                  55                  60

Asp Ala Leu Thr Leu Lys Ser Ser Gly Thr Val Asn Ile Thr Gly Gly
65                  70                  75                  80

Ala Ala Tyr Lys Ala Tyr Asp Lys Val Phe Gln Met Asn Ala Ser Gly
                85                  90                  95

Thr Ile Asn Ile Lys Asn Phe Arg Ala Asp Asp Ile Gly Lys Leu Val
                100                 105                 110

Arg Gln Asn Gly Gly Thr Ser Tyr Ala Val Asn Met Thr Leu Asp Asn
                115                 120                 125
```

```
Ser Asn Ile Ser Asn Val Lys Asp Ser Ile Met Arg Thr Asp Ser Ser
        130                 135                 140

Val Ser Gln Gly Lys Ile Thr Asn Thr Arg Tyr Ser Lys Val Pro Thr
145                 150                 155                 160

Leu Phe Lys Gly Phe Ala Ser Gly Lys Thr Ser Gln Ser Gly Asn Thr
                165                 170                 175

Gln Tyr

<210> SEQ ID NO 37
<211> LENGTH: 178
<212> TYPE: PRT
<213> ORGANISM: Bacillus sp. KSM-P15

<400> SEQUENCE: 37

Lys Gly Gln Thr Tyr Val Ala Asn Pro Asn Thr Leu Gly Asp Gly Ser
1               5                   10                  15

Gln Ala Glu Asn Gln Lys Pro Ile Phe Arg Leu Glu Ala Gly Ala Ser
                20                  25                  30

Leu Lys Asn Val Val Ile Gly Ala Pro Ala Ala Asp Gly Val His Cys
            35                  40                  45

Tyr Gly Asp Cys Thr Ile Thr Asn Val Ile Trp Glu Asp Val Gly Glu
50                  55                  60

Asp Ala Leu Thr Leu Lys Ser Ser Gly Thr Val Asn Ile Ser Gly Gly
65                  70                  75                  80

Ala Ala Tyr Lys Ala Tyr Asp Lys Val Phe Gln Ile Asn Ala Ala Gly
                85                  90                  95

Thr Ile Asn Ile Arg Asn Phe Arg Ala Asp Asp Ile Gly Lys Leu Val
            100                 105                 110

Arg Gln Asn Gly Gly Thr Thr Tyr Lys Val Val Met Asn Val Glu Asn
            115                 120                 125

Cys Asn Ile Ser Arg Val Lys Asp Ala Ile Leu Arg Thr Asp Ser Ser
        130                 135                 140

Thr Ser Thr Gly Arg Ile Val Asn Thr Arg Tyr Ser Asn Val Pro Thr
145                 150                 155                 160

Leu Phe Lys Gly Phe Lys Ser Gly Asn Thr Thr Ala Ser Gly Asn Thr
                165                 170                 175

Gln Tyr

<210> SEQ ID NO 38
<211> LENGTH: 229
<212> TYPE: PRT
<213> ORGANISM: E. carotovora

<400> SEQUENCE: 38

Ala Ala Ser Pro Glu Cys Lys Ala Gly Ala Val Ile Lys Asp Lys Thr
1               5                   10                  15

Val Asp Cys Gly Gly Ile Thr Leu Gly Leu Ser Cys Ser Gly Asp Ser
                20                  25                  30

Asp Lys Gln Pro Pro Val Ile Thr Leu Glu Asn Ala Thr Ile Lys Asn
                35                  40                  45

Leu Arg Ile Ser Glu Lys Gly Gly Ser Asp Gly Ile His Cys Lys Ser
            50                  55                  60

Gly Asn Cys Arg Ile Glu Asn Val Ile Trp Glu Asp Ile Cys Glu Asp
65                  70                  75                  80

Ala Ala Thr Asn Leu Gly Lys Thr Met Thr Ile Val Gly Gly Val Ala
```

```
                         85                  90                  95
His Asn Thr Thr Asn Gly Pro Gly Gly Lys Pro Asp Lys Val Leu Gln
                100                 105                 110

Gln Asn Ala Lys Asn Ser His Thr Ile Val Gln Gly Lys Phe Thr Leu
            115                 120                 125

Thr Gly Gln His Gly Lys Leu Trp Arg Ser Cys Gly Asp Cys Thr Asn
        130                 135                 140

Asn Gly Gly Pro Arg Asn Leu Thr Ile Ile Ser Ala Thr Val Asn Gly
145                 150                 155                 160

Thr Ile Asp Ser Ile Ala Gly Val Asn Arg Asn Phe Gly Asp Val Ala
                165                 170                 175

Glu Ile Arg Asp Leu Arg Ile Lys Gly Tyr Lys Glu Gly Lys Pro Pro
            180                 185                 190

Val Cys Glu Glu Phe Asn Gly Val Glu Lys Gly Lys Gly Lys Ser Asp
        195                 200                 205

Lys Tyr Gly Glu Phe Trp Asp Thr Lys Asn Cys Lys Val Ser Arg Ser
210                 215                 220

Asn Val Lys Pro Leu
225

<210> SEQ ID NO 39
<211> LENGTH: 229
<212> TYPE: PRT
<213> ORGANISM: E. chrysanthemi

<400> SEQUENCE: 39

Lys Ala Ser Ser Glu Cys Lys Pro Gly Ala Thr Phe Glu Asn Arg Thr
1               5                   10                  15

Val Asp Cys Gly Gly Val Thr Ile Gly Thr Ser Cys Pro Asn Asp Ser
            20                  25                  30

Asp Lys Gln Lys Pro Leu Ile Ile Leu Lys Asn Ala Thr Val Lys Asn
        35                  40                  45

Leu Arg Ile Ser Ala Ser Gly Arg Ala Asp Gly Ile His Cys Asp Ser
    50                  55                  60

Gly Asn Cys Thr Ile Glu Asn Val Ile Trp Glu Asp Ile Cys Glu Asp
65                  70                  75                  80

Ala Ala Thr Asn Asn Gly Lys Thr Met Thr Ile Val Gly Gly Ile Ala
                85                  90                  95

His Asn Ala Lys Asp Gly Tyr Gly Gly Lys Pro Asp Lys Val Leu Gln
                100                 105                 110

His Asn Ser Lys Asn Ser Thr Thr Val Val Lys Gly Asn Phe Thr Leu
            115                 120                 125

Thr Gly Glu His Gly Lys Leu Trp Arg Ser Cys Gly Asp Cys Ser Asn
        130                 135                 140

Asn Gly Gly Pro Arg Phe Leu Thr Val Thr Ser Ala Thr Val Asn Gly
145                 150                 155                 160

Thr Ile Asp Ser Ile Ala Gly Val Asn Arg Asn Tyr Gly Asp Val Ala
                165                 170                 175

Thr Ile Ser Gly Leu Lys Ile Lys Asn Tyr Lys Glu Gly Lys Pro Pro
            180                 185                 190

Val Cys Glu Glu Phe Lys Gly Val Val Lys Gly Gln Gly Ser Thr Glu
        195                 200                 205

Lys Tyr Gly Glu Lys Trp Asp Thr Thr Asn Cys Lys Val Ser Arg Ser
210                 215                 220
```

```
Gly Val Ser Lys Leu
        225

<210> SEQ ID NO 40
<211> LENGTH: 199
<212> TYPE: PRT
<213> ORGANISM: F. solani

<400> SEQUENCE: 40

Gly Met Lys Arg Phe Val Arg Asn Pro Thr Thr Cys Lys Asp Gln Tyr
1               5                   10                  15

Glu Thr Gly Glu Lys Asp Ala Ser Phe Ile Leu Glu Asp Gly Ala Thr
            20                  25                  30

Leu Ser Asn Val Ile Ile Asp Arg Ser Ser Gly Glu Gly Val His Cys
        35                  40                  45

Lys Gly Thr Cys Thr Leu Asn Asn Val Trp Trp Ala Asp Val Cys Glu
    50                  55                  60

Asp Ala Ala Thr Phe Lys Gln Lys Ser Gly Thr Ser Thr Ile Asn Gly
65                  70                  75                  80

Gly Gly Ala Phe Ser Ala Gln Asp Lys Val Leu Gln Phe Asn Gly Arg
                85                  90                  95

Gly Thr Leu Asn Val Asn Asp Phe Tyr Val Gln Asp Tyr Gly Lys Leu
            100                 105                 110

Val Arg Asn Cys Gly Asn Cys Glu Gly Asn Gly Pro Arg Asn Ile
        115                 120                 125

Asn Ile Lys Gly Val Val Ala Lys Asn Gly Gly Glu Leu Cys Gly Val
    130                 135                 140

Asn His Asn Tyr Gly Asp Val Cys Thr Ile Thr Asp Ser Cys Gln Asn
145                 150                 155                 160

Lys Gly Lys Ser Cys Gln Ala Tyr Thr Gly Asn Asp Gln Lys Lys Glu
                165                 170                 175

Pro Pro Lys Phe Gly Pro Ala Gly Asp Asn Gly Lys Ser Cys Leu Val
            180                 185                 190

Lys Ser Leu Arg Thr Asn Cys
        195

<210> SEQ ID NO 41
<211> LENGTH: 5
<212> TYPE: PRT
<213> ORGANISM: artificial
<220> FEATURE:
<223> OTHER INFORMATION: pectate lyase conserved sequence pattern

<400> SEQUENCE: 41

Val Trp Ile Asp His
1               5

<210> SEQ ID NO 42
<211> LENGTH: 14
<212> TYPE: PRT
<213> ORGANISM: artificial
<220> FEATURE:
<223> OTHER INFORMATION: pectate lyase conserved sequence pattern
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
```

```
<221> NAME/KEY: misc_feature
<222> LOCATION: (13)..(13)
<223> OTHER INFORMATION: Xaa can be any naturally occurring amino acid

<400> SEQUENCE: 42

Ala Xaa Asp Ile Lys Gly Xaa Xaa Xaa Xaa Val Thr Xaa Ser
1               5                   10

<210> SEQ ID NO 43
<211> LENGTH: 19
<212> TYPE: PRT
<213> ORGANISM: artificial
<220> FEATURE:
<223> OTHER INFORMATION: pectate lyase conserved sequence pattern
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(18)
<223> OTHER INFORMATION: Xaa can be any naturally occurring amino acid

<400> SEQUENCE: 43

Val Xaa Xaa Arg Xaa Pro Xaa Xaa Arg Xaa Gly Xaa Xaa His Xaa Xaa
1               5                   10                  15

Xaa Xaa Asn

<210> SEQ ID NO 44
<211> LENGTH: 251
<212> TYPE: PRT
<213> ORGANISM: T. maritime

<400> SEQUENCE: 44

Met Leu Met Arg Phe Ser Arg Val Val Ser Leu Val Leu Leu Leu Val
1               5                   10                  15

Phe Thr Ala Val Leu Thr Gly Ala Val Lys Ala Ser Leu Asn Asp Lys
                20                  25                  30

Pro Val Gly Phe Ala Ser Val Pro Thr Ala Asp Leu Pro Glu Gly Thr
            35                  40                  45

Val Gly Gly Leu Gly Gly Glu Ile Val Phe Val Arg Thr Ala Glu Glu
        50                  55                  60

Leu Glu Lys Tyr Thr Thr Ala Glu Gly Lys Tyr Val Ile Val Val Asp
65              70                  75                  80

Gly Thr Ile Val Phe Glu Ile Lys Val Leu Ser Asp Lys Thr Ile Val
                85                  90                  95

Gly Ile Asn Asp Ala Lys Ile Val Gly Gly Leu Val Ile Lys Asp
            100                 105                 110

Ala Gln Asn Val Ile Ile Arg Asn Ile His Phe Glu Gly Phe Tyr Met
        115                 120                 125
```

Glu Asp Asp Pro Arg Gly Lys Lys Tyr Asp Phe Asp Tyr Ile Asn Val
            130                 135                 140

Glu Asn Ser His His Ile Trp Ile Asp His Cys Thr Phe Val Asn Gly
145                 150                 155                 160

Asn Asp Gly Ala Val Asp Ile Lys Lys Tyr Ser Asn Tyr Ile Thr Val
                165                 170                 175

Ser Trp Cys Lys Phe Val Asp His Asp Lys Val Ser Leu Val Gly Ser
                180                 185                 190

Ser Asp Lys Glu Asp Pro Glu Gln Ala Gly Gln Ala Tyr Lys Val Thr
                195                 200                 205

Tyr His His Asn Tyr Phe Lys Asn Cys Ile Gln Arg Met Pro Arg Ile
            210                 215                 220

Arg Phe Gly Met Ala His Val Phe Asn Asn Phe Tyr Ser Met Gly Leu
225                 230                 235                 240

Arg Thr Gly Val Ser Gly Asn Val Phe Pro Ile
                245                 250

<210> SEQ ID NO 45
<211> LENGTH: 279
<212> TYPE: PRT
<213> ORGANISM: B. subtilis

<400> SEQUENCE: 45

Met Lys Lys Met Leu Leu Met Leu Ala Val Cys Leu Cys Met Ile Pro
1               5                   10                  15

Ala Asp Val Tyr Ala Ala Asp Leu Gly Arg Gln Thr Leu Gly Thr Asn
                20                  25                  30

Asp Gly Trp Gly Ala Ala Ser Gly Thr Thr Gly Gly Ala Lys Ala
            35                  40                  45

Ser Ser Ser Asn Val Tyr Thr Val Ser Asn Arg Gln Gln Leu Val Ser
        50                  55                  60

Ala Leu Gly Gly Ser Ala Asn Ser Thr Pro Lys Ile Ile Tyr Ile Gln
65                  70                  75                  80

Gly Thr Ile Asn Met Asn Asn Gln Lys Ala Arg Val Val Ile Asp Ile
                85                  90                  95

Pro Ser Asn Thr Thr Ile Ile Gly Ser Gly Ser Asn Ala Lys Val Thr
                100                 105                 110

Gly Gly Ser Phe Asn Ile Lys Asn Gly Val Asp Asn Val Ile Val Arg
            115                 120                 125

Asn Ile Glu Phe Gln Asp Ala Tyr Asp Tyr Phe Pro Gln Trp Asp Pro
130                 135                 140

Thr Asp Gly Ser Ser Gly Asn Trp Asn Ser Glu Tyr Asp Asn Ile Thr
145                 150                 155                 160

Ile Asn Gly Ala Thr His Ile Trp Ile Asp His Cys Thr Phe Asn Asp
                165                 170                 175

Gly Ser Asn Pro Asp Ser Gly Phe Pro Tyr Tyr Gly Arg Lys Tyr
                180                 185                 190

Gln His His Asp Gly Gln Thr Asp Ile Ala Asn Gly Ala Asn Tyr Ile
            195                 200                 205

Thr Leu Ser Tyr Asn Lys Tyr His Asp His Asp Lys Gly Ser Val Ile
            210                 215                 220

Gly Asn Ser Asp Ser Lys Thr Ser Asp Glu Gly Lys Leu Lys Val Thr
225                 230                 235                 240

Ile His His Asn Tyr Tyr Gln Asn Ile Val Gln Arg Ala Pro Arg Val

```
                     245                 250                 255
Arg Tyr Gly Gln Val His Ile Tyr Asn Asn Phe Tyr Ala Gly Ser Lys
            260                 265                 270
Ser Ala Ala Tyr Pro Phe Ser
            275

<210> SEQ ID NO 46
<211> LENGTH: 279
<212> TYPE: PRT
<213> ORGANISM: B. amyloliquefaciens

<400> SEQUENCE: 46

Met Lys Lys Met Leu Leu Met Leu Ala Val Cys Leu Cys Met Ile Pro
1               5                   10                  15

Ala Asp Val Tyr Ala Ala Asp Leu Gly Arg Gln Thr Leu Gly Thr Asn
            20                  25                  30

Asp Gly Trp Gly Ala Ala Ser Gly Gly Thr Thr Gly Gly Ala Lys Ala
        35                  40                  45

Ser Ser Ser Asn Val Tyr Thr Val Ser Asn Arg Gln Gln Leu Val Ser
    50                  55                  60

Ala Leu Gly Gly Ser Ala Asn Ser Thr Pro Lys Ile Ile Tyr Ile Gln
65                  70                  75                  80

Gly Thr Ile Asn Met Asn Asn Gln Lys Ala Arg Val Val Ile Asp Ile
                85                  90                  95

Pro Ser Asn Thr Thr Ile Ile Gly Ser Gly Ser Asn Ala Lys Val Thr
            100                 105                 110

Gly Gly Ser Phe Asn Ile Lys Asn Gly Val Asp Asn Val Ile Val Arg
        115                 120                 125

Asn Ile Glu Phe Gln Asp Ala Tyr Asp Tyr Phe Pro Gln Trp Asp Pro
    130                 135                 140

Thr Asp Gly Ser Ser Gly Asn Trp Asn Ser Glu Tyr Asp Asn Ile Thr
145                 150                 155                 160

Ile Asn Gly Ala Thr His Ile Trp Ile Asp His Cys Thr Phe Asn Asp
                165                 170                 175

Gly Ser Asn Pro Asp Ser Gly Phe Pro Tyr Tyr Tyr Gly Arg Lys Tyr
            180                 185                 190

Gln His His Asp Gly Gln Thr Asp Ile Ala Asn Gly Ala Asn Tyr Ile
        195                 200                 205

Thr Leu Ser Tyr Asn Lys Tyr His Asp His Asp Lys Gly Ser Val Ile
    210                 215                 220

Gly Asn Ser Asp Ser Lys Thr Ser Asp Glu Gly Lys Leu Lys Val Thr
225                 230                 235                 240

Ile His His Asn Tyr Tyr Gln Asn Ile Val Gln Arg Ala Pro Arg Val
                245                 250                 255

Arg Tyr Gly Gln Val His Ile Tyr Asn Asn Phe Tyr Ala Gly Ser Lys
            260                 265                 270

Ser Ala Ala Tyr Pro Phe Ser
            275

<210> SEQ ID NO 47
<211> LENGTH: 278
<212> TYPE: PRT
<213> ORGANISM: Bacillus sp. YA-14

<400> SEQUENCE: 47

Met Lys Lys Val Met Leu Ala Thr Ala Leu Phe Leu Gly Leu Thr Pro
```

```
  1               5                  10                 15
Ala Gly Ala Asn Ala Ala Asp Leu Gly His Gln Thr Leu Gly Ser Asn
            20                  25                  30

Asp Gly Trp Gly Ala Tyr Ser Thr Gly Thr Thr Gly Gly Ser Lys Ala
            35                  40                  45

Ser Ser Ser Asn Val Tyr Thr Val Ser Asn Arg Asn Gln Leu Val Ser
 50                      55                  60

Ala Leu Gly Lys Glu Thr Asn Thr Thr Pro Lys Ile Ile Tyr Ile Lys
 65                 70                  75                  80

Gly Thr Ile Asp Met Asn Asn Gln Lys Ala Arg Val Met Val Asp Ile
                85                  90                  95

Pro Ala Asn Thr Thr Ile Val Gly Ser Gly Thr Asn Ala Lys Val Val
             100                 105                 110

Gly Gly Asn Phe Gln Ile Lys Ser Asp Asn Val Ile Ile Arg Asn Ile
             115                 120                 125

Glu Phe Gln Asp Ala Tyr Asp Tyr Phe Pro Gln Trp Asp Pro Thr Asp
 130                     135                 140

Gly Ser Ser Gly Asn Trp Asn Ser Gln Tyr Asp Asn Ile Thr Ile Asn
 145                 150                 155                 160

Gly Gly Thr His Ile Trp Ile Asp His Cys Thr Phe Asn Asp Gly Ser
                 165                 170                 175

Arg Pro Asp Ser Thr Ser Pro Lys Tyr Tyr Gly Arg Lys Tyr Gln His
             180                 185                 190

His Asp Gly Gln Thr Asp Ala Ser Asn Gly Ala Asn Tyr Ile Thr Met
             195                 200                 205

Ser Tyr Asn Tyr Tyr His Asp His Asp Lys Ser Ser Ile Phe Gly Ser
 210                     215                 220

Ser Asp Ser Lys Thr Ser Asp Asp Gly Lys Leu Lys Ile Thr Leu His
 225                 230                 235                 240

His Asn Arg Tyr Lys Asn Ile Val Gln Arg Ala Pro Arg Val Arg Phe
             245                 250                 255

Gly Gln Val His Val Tyr Asn Asn Tyr Tyr Glu Gly Ser Thr Ser Ser
             260                 265                 270

Ser Ser Tyr Pro Phe Ser
             275

<210> SEQ ID NO 48
<211> LENGTH: 278
<212> TYPE: PRT
<213> ORGANISM: B. subtilis

<400> SEQUENCE: 48

Met Lys Lys Val Met Leu Ala Thr Ala Leu Phe Leu Gly Leu Thr Pro
 1               5                  10                 15

Ala Gly Ala Asn Ala Ala Asp Leu Gly His Gln Thr Leu Gly Ser Asn
            20                  25                  30

Asp Gly Trp Gly Ala Tyr Ser Thr Gly Thr Thr Gly Gly Ser Lys Ala
            35                  40                  45

Ser Ser Ser Asn Val Tyr Thr Val Ser Asn Arg Asn Gln Leu Val Ser
 50                      55                  60

Ala Leu Gly Lys Glu Thr Asn Thr Thr Pro Lys Ile Ile Tyr Ile Lys
 65                 70                  75                  80

Gly Thr Ile Asp Met Asn Asn Gln Lys Ala Arg Val Met Val Asp Ile
                85                  90                  95
```

-continued

```
Pro Ala Asn Thr Thr Ile Val Gly Ser Gly Thr Asn Ala Lys Val Val
                100                 105                 110

Gly Gly Asn Phe Gln Ile Lys Ser Asp Asn Val Ile Ile Arg Asn Ile
            115                 120                 125

Glu Phe Gln Asp Ala Tyr Asp Tyr Phe Pro Gln Trp Asp Pro Thr Asp
130                 135                 140

Gly Ser Ser Gly Asn Trp Asn Ser Gln Tyr Asp Asn Ile Thr Ile Asn
145                 150                 155                 160

Gly Gly Thr His Ile Trp Ile Asp His Cys Thr Phe Asn Asp Gly Ser
                165                 170                 175

Arg Pro Asp Ser Thr Ser Pro Lys Tyr Tyr Gly Arg Lys Tyr Gln His
            180                 185                 190

His Asp Gly Gln Thr Asp Ala Ser Asn Gly Ala Asn Tyr Ile Thr Met
        195                 200                 205

Ser Tyr Asn Tyr Tyr His Asp His Asp Lys Ser Ser Ile Phe Gly Ser
    210                 215                 220

Ser Asp Ser Lys Thr Ser Asp Asp Gly Lys Leu Lys Ile Thr Leu His
225                 230                 235                 240

His Asn Arg Tyr Lys Asn Ile Val Gln Arg Ala Pro Arg Val Arg Phe
                245                 250                 255

Gly Gln Val His Val Tyr Asn Asn Tyr Tyr Glu Gly Ser Thr Ser Ser
            260                 265                 270

Ser Ser Tyr Pro Phe Ser
        275

<210> SEQ ID NO 49
<211> LENGTH: 283
<212> TYPE: PRT
<213> ORGANISM: B. licheniformis

<400> SEQUENCE: 49

Met Lys Arg Phe Phe Ser Val Ile Ile Leu Gly Ala Leu Leu Leu Leu
1               5                   10                  15

Gly Thr Ser Ala Pro Ile Glu Ala Ala Asp Tyr Gly Arg Asp Val Leu
            20                  25                  30

Gly Ser Lys Asp Gly Trp Gly Ala Tyr Gly Lys Gly Thr Thr Gly Gly
        35                  40                  45

Ala Asp Ala Ser Ser Asp Gln Val Tyr Thr Val Lys Asn Arg Lys Gln
    50                  55                  60

Leu Val Glu Ala Leu Gly Gly Asp Asn Lys Lys Asn Ser Glu Asn Asp
65                  70                  75                  80

Thr Pro Lys Ile Ile Tyr Val Lys Gly Thr Ile Asn Leu Ser Asn Gln
                85                  90                  95

Lys Glu Arg Val Leu Ile Arg Val Gly Ser Asn Thr Thr Ile Ile Gly
            100                 105                 110

Leu Gly Asp Ala Lys Ile Val Gly Gly Gly Leu Tyr Val Lys Asn
            115                 120                 125

Ala Glu Asn Val Ile Ile Arg Asn Ile Glu Phe Glu Asn Ala Tyr Asp
    130                 135                 140

Phe Phe Pro Gly Trp Asp Pro Thr Asp Gly Ser Ser Gly Asn Trp Asn
145                 150                 155                 160

Ser Glu Tyr Asp Asn Leu Leu Ile Glu Met Ser Lys Asn Ile Trp Ile
                165                 170                 175

Asp His Cys Ser Phe Asn Asp Gly Asp Gln Pro Asp Glu Leu Thr Glu
            180                 185                 190
```

```
Thr His Phe Gly Arg Glu Phe Gln His His Asp Gly Leu Leu Asp Ile
        195                 200                 205

Lys Lys Gln Ser Asp Phe Ile Thr Val Ser Tyr Ser Ile Phe Ser Gly
    210                 215                 220

His Ser Lys Asn Thr Ile Ile Gly Ser Ser Asp Ser Tyr Lys Ala Asp
225                 230                 235                 240

Asn Gly His Leu Arg Val Thr Phe His Asn Leu Tyr Glu Asn Ile
                245                 250                 255

Lys Glu Arg Ala Pro Arg Val Arg Tyr Gly Lys Val His Ile Tyr Asn
            260                 265                 270

Asn Tyr Phe Lys Ser Thr Lys Asp Ser Tyr Asn
        275                 280

<210> SEQ ID NO 50
<211> LENGTH: 260
<212> TYPE: PRT
<213> ORGANISM: P. amylolyticus

<400> SEQUENCE: 50

Met Lys Lys Thr Val Arg Ser Leu Cys Ser Thr Ala Leu Ala Leu Thr
1               5                   10                  15

Leu Gly Phe Thr Leu Leu Ser Gly Pro Ala Ser Val Gln Ala Ala Gly
            20                  25                  30

Asn Ala Asp Tyr Asn Leu Ala Gly Phe Ser Gln Gly Asn Thr Gly Gly
        35                  40                  45

Gly Ile Ile Ser Glu Ser Asn Thr Ser Thr Tyr Lys Lys Val Tyr Asn
50                  55                  60

Ala Thr Asp Leu Ala Leu Ala Leu Lys Lys Asn Ser Gly Val Lys Val
65                  70                  75                  80

Val Glu Ile Met Asn Asp Leu Asp Leu Gly Thr Gly Val Ser Lys Ile
                85                  90                  95

Thr Val Asp Gly Phe Asn Gly Leu Thr Ile Phe Ser Ala Asn Gly Ser
            100                 105                 110

Lys Ile Lys His Ala Ala Ile Thr Val Lys Arg Ser Ser Asn Val Ile
        115                 120                 125

Ile Arg Asn Leu Glu Phe Asp Glu Leu Trp Glu Trp Asp Glu Ser Thr
130                 135                 140

Lys Gly Asp Tyr Asp Lys Asn Asp Trp Asp Tyr Ile Thr Leu Glu Asp
145                 150                 155                 160

Ser Ser Gly Val Trp Ile Asp His Cys Thr Phe Asn Lys Ala Tyr Asp
                165                 170                 175

Gly Leu Val Asp Ser Lys Lys Gly Thr Ser Gly Val Thr Ile Ser Trp
            180                 185                 190

Ser Thr Phe Lys Gly Asp Asp Gly Ser Ala Asn Ser Trp Val Thr Arg
        195                 200                 205

Gln Ile Asn Glu Leu Glu Ala Asn Lys Ala Ser Tyr Pro Met Tyr Asn
210                 215                 220

Tyr Leu Arg Ser Ser Ala Val Gly Leu Ser Lys Gln Asp Val Ile Ala
225                 230                 235                 240

Ile Ser Gly Pro Gln Lys Lys Gly His Leu Val Gly Ala Thr Ser Leu
                245                 250                 255

Glu Ser Ala Asn
        260
```

METHODS AND COMPOSITIONS FOR DEGRADING PECTIN

CONTINUING APPLICATION DATA

This application is a divisional of U.S. patent application Ser. No. 13/063,272, filed on Mar. 10, 2011, Confirmation No. 1513, now abandoned, which is the §371 U.S. National Stage of International Application No. PCT/US2009/057508, filed 18 Sep. 2009, which claims the benefit of U.S. Provisional Application Ser. No. 61/097,975, filed Sep. 18, 2008, and 61/179,570, filed May 19, 2009, each of which are incorporated by reference herein in their entireties.

BACKGROUND

The US Energy Independence and Security Act (EISA) of 2007 states that transportation fuel introduced into commerce in the US (annual average) contain at least 12.95 billion gallons of renewable fuels by the year 2010. Ethanol is the most prevalent renewable fuel, with the US producing over 6 billion gallons in 2007 (Peterson and Ingram, 2008, Ann. N.Y. Acad. Sci., 1125:363-372) and 9 billion gallons in 2009. Currently, the majority of ethanol is produced from corn; however, limited supply will force ethanol production from other sources of biomass, of which the US produces over a billion tons annually—enough to produce 80 billion gallons of renewable fuel (Gray et al., 2006, Bioethanol. Curr. Opin. Chem. Biol., 10:141). Moreover, use of waste biomass for fuel production positively affects greenhouse gases and carbon debt without causing land-use change (Fargione et al., 2008, Science, 319:1235-1237, Searchinger et al., 2008, Science, 319:1238-1240). The EISA of 2007 also requires that ethanol, and other liquid transportation fuels such as butanol and biomass-based diesel, derived from any of the following: cellulose, hemicellulose, lignin, sugar, starch (other than corn starch), waste material and residues, be incorporated into our 2010 fuel supply at 0.95 billion gallons. By the year 2015 over 5 billion gallons of advanced renewable fuel from biomass other than corn starch are required to be available for use in our transportation sector.

Unlike corn grain, where the major component is starch, other sources of biomass are composed of 40-50% cellulose, 25-35% hemicellulose, and 15-20% lignin (Gray et al., 2006, Bioethanol. Curr. Opin. Chem. Biol., 10:141, Doran-Peterson et al., 2008, The Plant J., 54:582-592). The highly complex biomass structure has necessitated development of many processes for fuel ethanol conversions from substrates containing lignocellulose, which can include thermochemical and/or mechanical pretreatment to allow enzymatic access, enzymatic degradation to reduce substrates to fermentable sugars, and finally fermentation of those sugars by microorganisms. Commercially available enzyme mixtures are usually culture supernatants from fungi, and sometimes bacteria, containing a complex of enzyme activities. In order to efficiently degrade cellulose several major classes of enzymes are required, such as endo-β-1,4-glucanases (endocellulase, Cx-cellulase; EC 3.2.1.4) which cleave internal β-1,4-glycosidic bonds generating oligosaccharides; exo-β-1,4-glucanases (exocellulase, cellobiohydrolaseC1-cellulase; EC 3.2.1.91) which cleave the non-reducing end to release a dimer of glucose called cellobiose; and β-glucosidase (cellobiase, EC 3.2.1.21) which cleaves cellobiose into monomeric glucose molecules (Whitaker, 1994, Principles of Enzymology for the Food Sciences, 2nd Ed. Marcel Dekker, New York, Gilkes et al., 1991, Microbiol Rev., 55:303-315, Henrissat et al., 1989, Gene, 81(1):83-95, Béguin et al., 1994, FEMS Microbiol Rev., 1994 13(1):25-58). Many commercial preparations are deficient in cellobiase, and when this dissacharide accumulates it can inhibit further enzyme deconstruction of the cellulose microfibrils.

In some biomass types, such as sugar beet pulp and citrus peel, pectin can also compose a significant portion of the lignocellulose structure and functions as a matrix to hold cellulose and hemicellulose fibers. The pectin backbone can consist of a homopolymer of α-1,4-D-galacturonic acid (homogalacturonan) or repeats of the disaccharide α-1,2-L-rhamnose-α-1,4-D-galacturonic acid (rhamnogalacturonan-I), and, typically, 70% to 80% of galacturonic acid residues are methylated. Homogalacturonan can be substituted with xylose or apiose, while rhamnogalacturonan-I is often substituted with galactose, arabinose, or galactan (Willats et al., 2001, Plant Mol. Biol., 47:9-27, Ridley et al., 2001, Phytochemistry, 57:929-967).

The degradation of pectin requires both methylesterases and depolymerases. Pectin methylesterases are responsible for the hydrolysis of methylester linkages from the polygalacturonic acid backbone (Whitaker, 1984, Enzyme Microbial Technol., 6:341-347). Pectin depolymerases act upon the polygalacturonate backbone and belong to one of two families: polygalacturonases or lyases. Polygalacturonases are responsible for the hydrolytic cleavage of the polygalacturonate chain, while lyases cleave by β-elimination giving a Δ4,5-unsaturated product (Jayani et al., 2005, Process Biochem., 40:2931-2944, Sakai et al., 1993, Adv. Appl. Microbiol., 39:231-294). There are two types of lyases: pectate lyases, which cleave unesterified polygalacturonate, or pectate; and pectin lyases, which cleave methyl esterified pectin. Pectate lyases have been classified into families based on amino acid similarity, which in turn suggests structural features (Coutinho and Henrissat, 1999, In: Gilbert et al. (Eds.) Recent Advances in Carbohydrate Bioengineering. Cambridge, The Royal Society of Chemistry).

Once the lignocellulosic biomass is degraded into fermentable sugars, many different types of sugars, including pentose and acidic sugars are liberated for metabolism to a product(s) (Doran-Peterson et al., 2008, The Plant J., 54:582-592). Most ethanol fermentations in the U.S. today use the yeast *Saccharomyces cerevisiae* to convert starch glucose into ethanol and $CO_2$; however, lignocellulosic biomass contains many sugars that *S. cerevisiae* is unable to ferment (Peterson and Ingram, 2008, Ann. N.Y. Acad. Sci., 1125:363-372). Thus, *Escherichia coli*, which is capable of using these hexoses and pentoses, was engineered as a biocatalyst for ethanol production by integration of the pyruvate decarboxylase (pdc) and alcohol dehydrogenase II (adhB) genes from *Zymomonas mobilis* into the chromosome of *E. coli* to generate strain K011 (Ohta et al., 1991, Appl. Environ. Microbiol., 57:893-900).

SUMMARY OF THE INVENTION

Provided herein are polynucleotides that may be enriched, isolated, or purified. The polynucleotides include (a) a nucleotide sequence encoding a polypeptide having pectinase activity, wherein the amino acid sequence of the polypeptide and the amino acid sequence of SEQ ID NO:4 have at least 80% identity, (b) a nucleotide sequence encoding a polypeptide having pectinase activity, wherein the nucleotide sequence of the isolated polynucleotide and the nucleotide sequence of SEQ ID NO:3 have at least 80% identity, (c) a nucleotide sequence encoding a polypeptide having pectinase activity, wherein the amino acid sequence of the polypeptide and the amino acid sequence of SEQ ID NO:2 have at least 80% identity, and (d) a nucleotide sequence encoding a polypeptide having pectinase activity, wherein the nucleotide sequence of the isolated polynucleotide and the nucleotide sequence of SEQ ID NO:1 have at least 80% identity. Also disclosed are the full complements of the nucleotide sequences. The polynucleotide may be operably linked to at least one regulatory sequence, and may further include heterologous nucleotides. The polynucleotide may be part of a vector. Also disclosed are genetically modified microbes that include an exogenous polynucleotide described herein.

Also provided are polypeptides that may be enriched, isolated, or purified. The polypeptides have pectinase activity. The polypeptides include an amino acid sequence, wherein the amino acid sequence and the amino acid sequence of SEQ ID NO:2 or SEQ ID NO:4 have at least 80% identity. The polypeptide may be an exogenous polypeptide present in a genetically modified microbe, such as a gram-negative microbe (e.g., *E. coli*) or a fungus (e.g., *S. cerevisiae*). The genetically modified microbe may also include a polynucleotide encoding a polypeptide having oligogalacturonate activity. Further provided are compositions that include the polynucleotides and/or the polypeptides described herein, as well as compositions that include the genetically modified microbes described herein.

Yet further provided are methods for using the polynucleotides and/or polypeptides described herein. Methods for degrading pectin may include contacting a composition that contains pectin with a polypeptide having pectinase activity and disclosed herein under conditions suitable for the degradation of the pectin. The polypeptide used in the method may be enriched, isolated, or purified. The polypeptide may be expressed by a genetically modified microbe, and the contacting may include contacting the pectin with the genetically modified microbe. The genetically modified microbe may produce a metabolic product, such as ethanol, and the method may further include recovering the metabolic product. The composition may include a lignocellulosic material that is obtained from, for instance, a fruit or a vegetable. The pectin may be esterified or unesterified. If esterified, the level of esterification may be at least 8.5%, at least 20%, at least 30%, at least 40%, at least 50%, at least 60%, at least 70%, or at least 80%. The method may further include contacting the degraded pectin with a polypeptide having oligogalacturonate activity.

Also provided are methods for producing a metabolic product. The methods may include contacting a composition containing pectin with a genetically modified microbe under conditions suitable for the degradation of the pectin, wherein the genetically modified microbe includes a polypeptide having pectinase activity and disclosed herein. The method may further include contacting the degraded pectin with a polypeptide having oligogalacturonate activity. In another embodiment, the methods may include contacting a composition that contains pectin with a genetically modified microbe under conditions suitable for the degradation of the pectin, wherein the genetically engineered microbe comprises an exogenous polypeptide having pectinase activity and an exogenous polypeptide having oligogalacturonate activity. The metabolic product may be ethanol, and the method may further include recovering the metabolic product. The composition may include a lignocellulosic material that is obtained from, for instance, a fruit or a vegetable. The pectin may be esterified or unesterified. If esterified, the level of esterification may be at least 8.5%, at least 20%, at least 30%, at least 40%, at least 50%, at least 60%, at least 70%, or at least 80%.

As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions.

As used herein, the terms "coding region" and "coding sequence" are used interchangeably and refer to a nucleotide sequence that encodes a polypeptide and, when placed under the control of appropriate regulatory sequences expresses the encoded polypeptide. The boundaries of a coding region are generally determined by a translation start codon at its 5' end and a translation stop codon at its 3' end. A "regulatory sequence" is a nucleotide sequence that regulates expression of a coding sequence to which it is operably linked. Non-limiting examples of regulatory sequences include promoters, enhancers, transcription initiation sites, translation start sites, translation stop sites, and transcription terminators. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

A polynucleotide that includes a coding region may include heterologous nucleotides that flank one or both sides of the coding region. As used herein, "heterologous nucleotides" refer to nucleotides that are not normally present flanking a coding region that is present in a wild-type cell. For instance, a coding region present in a wild-type microbe and encoding a PelA polypeptide is flanked by homologous sequences, and any other nucleotide sequence flanking the coding region is considered to be heterologous. Examples of heterologous nucleotides include, but are not limited to regulatory sequences. Typically, heterologous nucleotides are present in a polynucleotide of the present invention through the use of standard genetic and/or recombinant methodologies well known to one skilled in the art. A polynucleotide of the present invention may be included in a suitable vector.

As used herein, an "exogenous polynucleotide" refers to a polynucleotide that is not normally or naturally found in a microbe. As used herein, the term "endogenous polynucleotide" refers to a polynucleotide that is normally or naturally found in a cell microbe. An "endogenous polynucleotide" is also referred to as a "native polynucleotide."

The terms "complement" and "complementary" as used herein, refer to the ability of two single stranded polynucleotides to base pair with each other, where an adenine on one strand of a polynucleotide will base pair to a thymine or uracil on a strand of a second polynucleotide and a cytosine on one strand of a polynucleotide will base pair to a guanine on a strand of a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary. The term "substantial complement" and cognates thereof as used herein, refer to a polynucleotide that is capable of selectively hybridizing to a specified polynucleotide under stringent hybridization conditions. Stringent hybridization can take place under a number of pH, salt and temperature conditions. The pH can vary from 6 to 9, preferably 6.8 to 8.5. The salt concentration can vary from 0.15 M sodium to 0.9 M sodium, and other cations can be used as long as the ionic strength is equivalent to that specified for sodium. The temperature of the hybridization reaction can vary from 30° C. to 80° C., preferably from 45° C. to 70° C. Additionally, other compounds can be added to a hybridization reaction to promote specific hybridization at lower temperatures, such as at or approaching room temperature. Among the compounds contemplated for lowering the temperature requirements is formamide. Thus, a polynucleotide is typically substantially complementary to a second polynucleotide if hybridization occurs between the polynucleotide and the second polynucleotide. As used herein, "specific hybridization" refers to hybridization between two polynucleotides under stringent hybridization conditions.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, tetramers). Thus, the terms peptide, oligopeptide, enzyme, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

As used herein, a polypeptide "fragment" includes any polypeptide which retains at least some of the activity of the corresponding native polypeptide. Examples of fragments of polypeptides described herein include, but are not limited to, proteolytic fragments and deletion fragments.

As used herein, an "enriched" polypeptide or polynucleotide is one that constitutes a significantly higher fraction (2 to 5 fold) of the total of amino acids or nucleotides present in the cells of interest than in the cells from which the sequence was separated. A skilled person can preferentially reduce the amount of other amino acids or nucleotides present, or preferentially increase the amount of specific amino acid sequences or nucleotide sequences of interest, or both. However, the term "enriched" does not imply that there are no other polypeptides or polynucleotides present. Enriched simply means the relative amount of the sequence of interest has been significantly increased. The term "significant" indicates that the level of increase is useful to the person making such an increase.

As used herein, an "isolated" polypeptide or polynucleotide is one that has been removed from its natural environment, produced using recombinant techniques, or chemically or enzymatically synthesized. For instance, a polypeptide or a polynucleotide can be isolated. As used herein, a purified" substance is one that is at least 80% free, preferably at least 90% free, and most preferably at least 95% free from other components with which they are naturally associated.

As used herein, "pectinase activity" refers to the ability of a polypeptide to catalyze the depolymerization of the polygalacturonate backbone of pectin by β-elimination giving a Δ4,5-unsaturated product (Jayani et al., 2005, *Process Biochem.*, 40:2931-2944, Sakai et al., 1993, *Adv. Appl. Microbiol.*, 39:231-294). The polypeptide having pectinase activity may have pectate lyase activity, pectin lyase activity, or both pectate lyase activity and pectin lyase activity. "Pectate lyase activity" refers to the ability of a polypeptide to degrade unesterified polygalacturonate, and "pectin lyase activity" refers to the ability of a polypeptide to degrade methyl esterified pectin. A pectinase disclosed herein may degrade pectin to oligogalacturonides having a degree of polymerization of less than 8, less than 7, less than 6, less than 5, less than 4, or less than 3.

As used herein, "oligogalacturonate activity" refers to the ability of a polypeptide to catalyze the degradation of short oligogalacturonates, such as oligogalacturonates with a degree of polymerization less than seven, to result in dimeric or monomeric sugars.

As used herein, "degrade" and "degradation" refers to the breakdown of a polysaccharide, typically by cleaving a polysaccharide between two saccharides. A single saccharide may be released if it is at the end of a polysaccharide, or two shorter polysaccharides may result if the cleavage site is present elsewhere in the polysaccharide. For instance, when the polysaccharide is pectin, a single galacturonic acid may be released, or a rhamnose-galacturonic acid disaccharide may be released As used herein, "identity" refers to sequence similarity between two polypeptides or two polynucleotides. The sequence similarity between two polypeptides is determined by aligning the residues of the two polypeptides (e.g., a candidate amino acid sequence and a reference amino acid sequence, such as SEQ ID NO:2 or SEQ ID NO:4) to optimize the number of identical amino acids along the lengths of their sequences; gaps in either or both sequences are permitted in making the alignment in order to optimize the number of shared amino acids, although the amino acids in each sequence must nonetheless remain in their proper order. The sequence similarity is typically at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. Sequence similarity may be determined, for example, using sequence techniques such as the BESTFIT algorithm in the GCG package (Madison Wis.), or the Blastp program of the BLAST search algorithm, available through the World Wide Web, for instance at the internet site maintained by the National Center for Biotechnology Information, National Institutes of Health. Preferably, sequence similarity between two amino acid sequences is determined using the Blastp program of the BLAST search algorithm. Preferably, the default values for all Blastp search parameters are used. In the comparison of two amino acid sequences using the Blastp search algorithm, structural similarity is referred to as "identities."

The sequence similarity between two polynucleotides is determined by aligning the residues of the two polynucleotides (e.g., a candidate nucleotide sequence and a reference nucleotide sequence, such as SEQ ID NO:1 or SEQ ID NO:3) to optimize the number of identical nucleotides along the lengths of their sequences; gaps in either or both sequences are permitted in making the alignment in order to optimize the number of shared nucleotides, although the nucleotides in each sequence must nonetheless remain in their proper order. The sequence similarity is typically at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. Sequence similarity may be determined, for example, using sequence techniques such as GCG FastA (Genetics Computer Group, Madison, Wis.), MacVector 4.5 (Kodak/IBI software package) or other suitable sequencing programs or methods known in the art. Preferably, sequence similarity between two nucleotide sequences is determined using the Blastn program of the BLAST search algorithm, available through the World Wide Web, for instance at the internet site maintained by the National Center for Biotechnology Information, National Institutes of Health. Preferably, the default values for all Blastn search parameters are used. In the comparison of two nucleotide sequences using the Blastn search algorithm, sequence similarity is referred to as "identities."

Conditions that "allow" an event to occur or conditions that are "suitable" for an event to occur, such as an enzymatic reaction, or "suitable" conditions are conditions that do not prevent such events from occurring. Thus, these conditions permit, enhance, facilitate, and/or are conducive to the event. Such conditions, known in the art and described herein, may depend upon, for example, the enzyme being used.

As used herein, a "microbe" refers to a prokaryotic cell, including bacteria and archaea, and a eukaryotic cell, including fungi (such as yeast).

As used herein, "genetically modified microbe" refers to a microbe into which has been introduced an exogenous polynucleotide, e.g., an expression vector. For example, a microbe is a genetically modified microbe by virtue of introduction into a suitable microbe of an exogenous polynucleotide that is foreign to the microbe. "Genetically modified microbe" also refers to a microbe that has been genetically manipulated such that endogenous nucleotides have been altered. For example, a microbe is a genetically modified microbe by virtue of introduction into a suitable microbe of an alteration of endogenous nucleotides. For instance, an endogenous coding region could be deleted or mutagenized. Such mutations may result in a polypeptide having a different amino acid sequence than was encoded by the endogenous polynucleotide. Another example of a genetically modified microbe is one having an altered regulatory sequence, such as a promoter, to result in increased or decreased expression of an operably linked endogenous coding region.

"Metabolic product" refers to any product (e.g., oxalic acid, succinic acid, lactic acid, pyruvic acid, salts thereof, amino acids, ethanol, etc.) from the fermentation of plant biomass, e.g., lignocelluosic biomass. Metabolic products include, but are not limited to, commodity chemicals such as small organic (e.g., C1-C8) acids such as, for example, succinic acid, lactic acid, citric acid, oxaloacetic acid, malic acid, adipic acid, fumaric acid, or pyruvic acid, and alcohols such as, for example, ethanol, n-butanol, 1,4-butanediol, sec-butanol, and/or methanol.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The term "and/or" means one or all of the listed elements or a combination of any two or more of the listed elements.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 4. Amino acid alignment of pectate lyase class 3 enzymes (CLUSTAL W). Numbering begins at the N-termini of the proteins. Gaps are indicated by dashes. In the final line, identical amino acids are indicated by asterisks and conserved and semi-conserved residues by colons and dots, respectively. Family PL3 conserved residues are boxed. Amino acids identical in at least six of the sequences aligned are shaded. BliYvpA, *B. licheniformis* protein from gene yvpA (SEQ ID NO: 32); BsuPe1C, *B. subtilis* pectate lyase C (SEQ ID NO: 33); BspP2850, *Bacillus* sp. P-2850 pectate lyase (SEQ ID NO: 34); PamPelA, *P. amylolyticus* pectate lyase A (SEQ ID NO: 35); PbaPelA, *P. barcinonensis* pectate lyase A (SEQ ID NO: 36); BspKSM15, *Bacillus* sp. KSM-P15 pectate lyase (SEQ ID NO: 37); EcaPe13, *E. carotovora* pectate lyase 3 (SEQ ID NO: 38); EchPelI, *E. chrysanthemi* pectate lyase I (SEQ ID NO: 39); and FsoPelB, *F. solani* pectate lyase B (SEQ ID NO: 40). The conserved arginine, which may play a role in the active site, is in bold.

FIG. 5. Amino acid alignment of pectate lyase class 1 enzymes (CLUSTAL W). Numbering begins at the N-termini of the proteins. Gaps are indicated by dashes. In the final line, identical amino acids are indicated by asterisks and conserved and semi-conserved residues by colons and dots, respectively. Pectate lyase conserved sequence patterns are boxed, vWIDH (SEQ ID NO: 41), AxDIKGxxxxVTxS (SEQ ID NO: 42), and VxxRxPxxRxGxxHxxxxN (SEQ ID NO: 43) (Henrissat et al., 1995, Plant Physiol., 107:963-976). Residues of sites conserved in all thermostable PL1 pectate lyase are highlighted in grey, conserved catalytic sites are highlighted in black, and conserved calcium binding sites are labeled with © symbol. TmaPelA, *T. maritime* MSB8 pectate lyase A (SEQ ID NO: 44); BsuBS2, *B. subtilis* BS-2 pectate lyase (SEQ ID NO: 45); BamPel, *B. amyloliquefaciens* TB-2 pectate lyase (SEQ ID NO: 46); BspYA14, *Bacillus* sp. YA-14 pectate lyase K (SEQ ID NO: 47); BsuPel, *B. subtilis* reference strain 168 pectate lyase (SEQ ID NO: 48); BliPel, *B. licheniformis* ATCC 14580 pectate lyase (SEQ ID NO: 49); and PamPelB, *P. amylolyticus* pectate lyase B (SEQ ID NO: 50).

Figure 6:
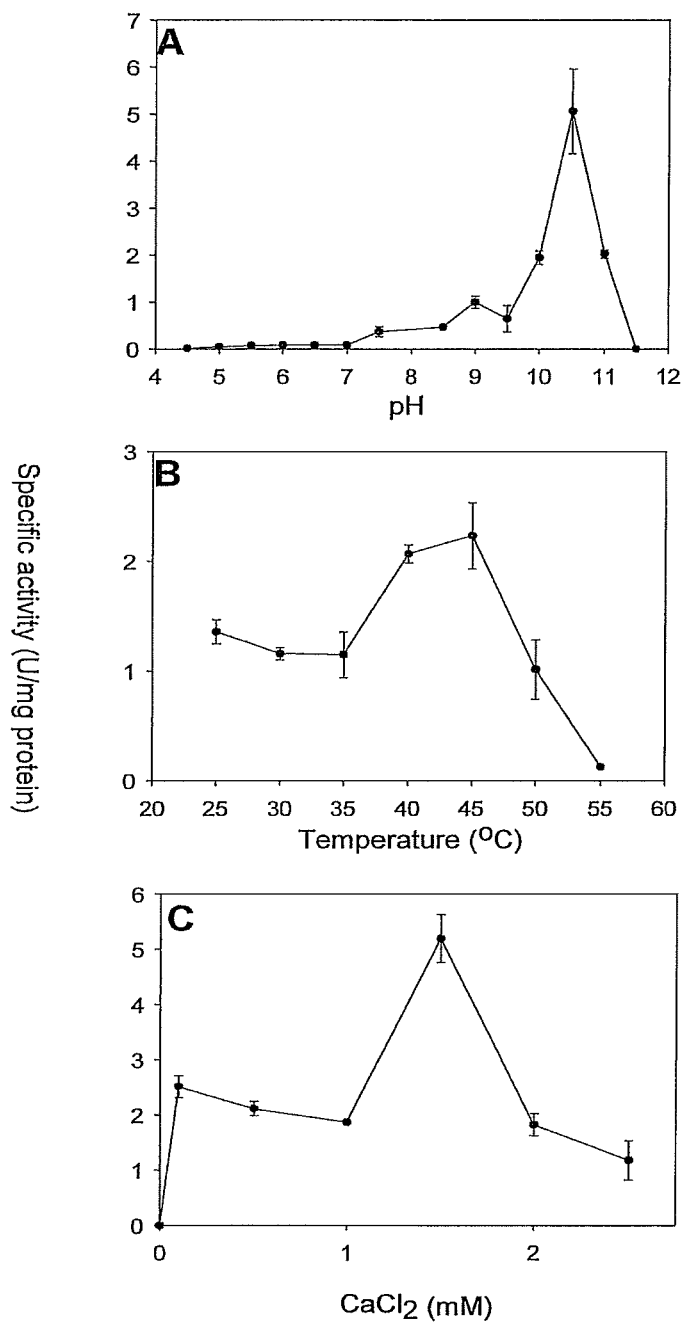

FIG. 6. PelA optima for pH (A), temperature (B), and $CaCl_2$ (C).

Figure 7:
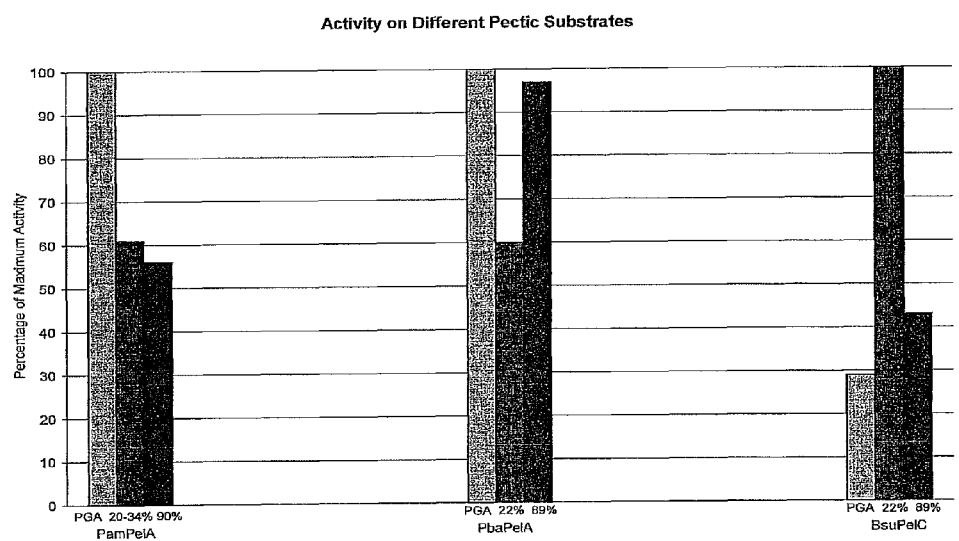

FIG. 7. Activity on different pectic substrates for *P. amylolyticus* pectate lyase A, PamPelA; *P. barcinonensis* pectate lyase A, PbaPelA; and *B. subtilis* pectate lyase C, BsuPelC.

Figure 8:
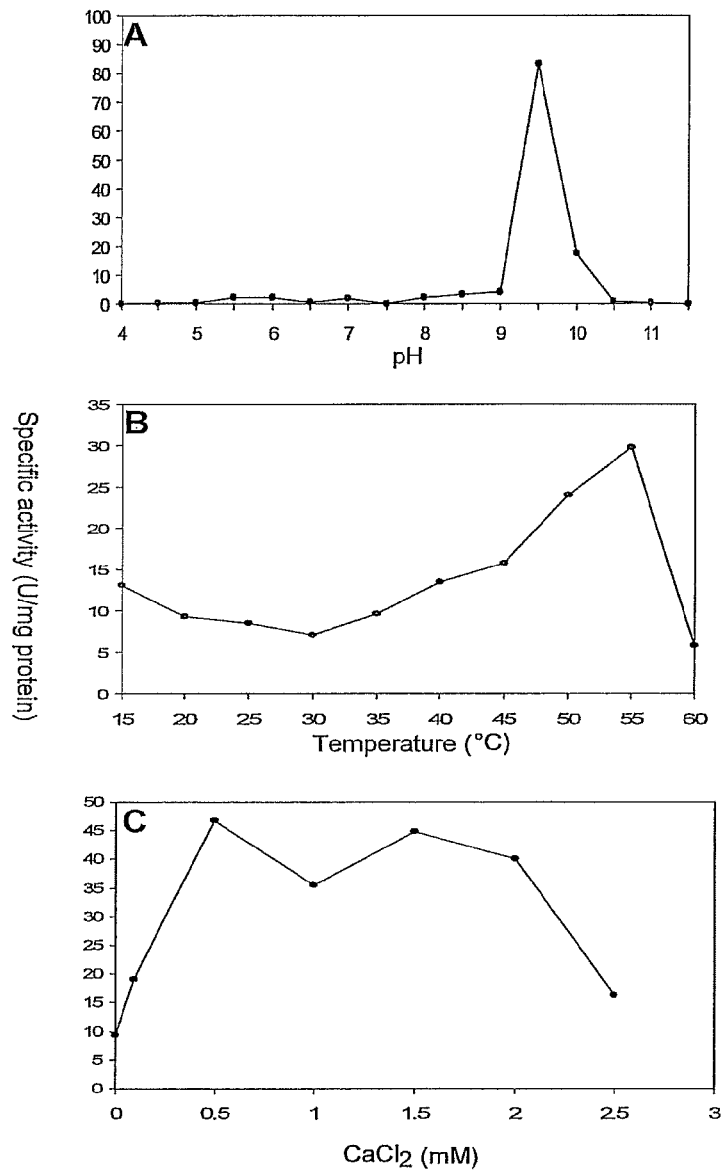

FIG. 8. PelB optima for pH (A), temperature (B), and $CaCl_2$ (C).

Figure 9:
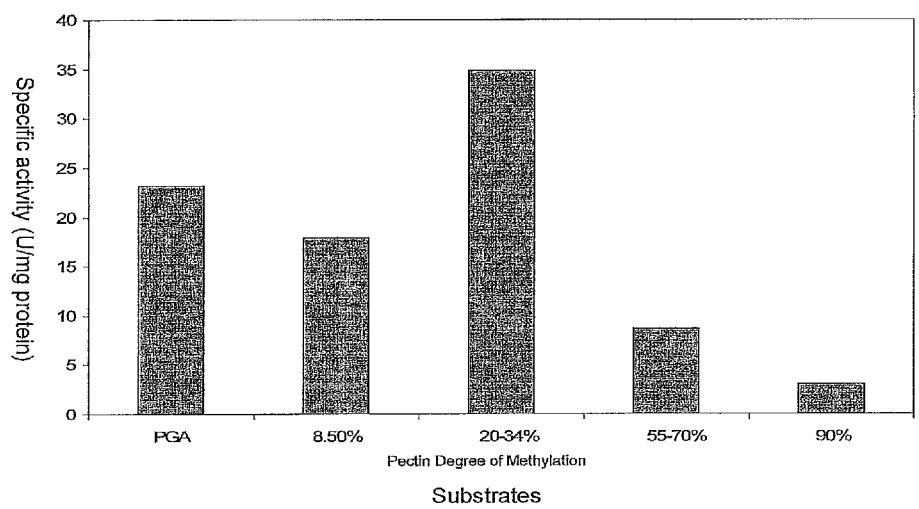

FIG. 9. *P. amylolyticus* pectate lyase B activity on different pectic substrates.

Figure 10:
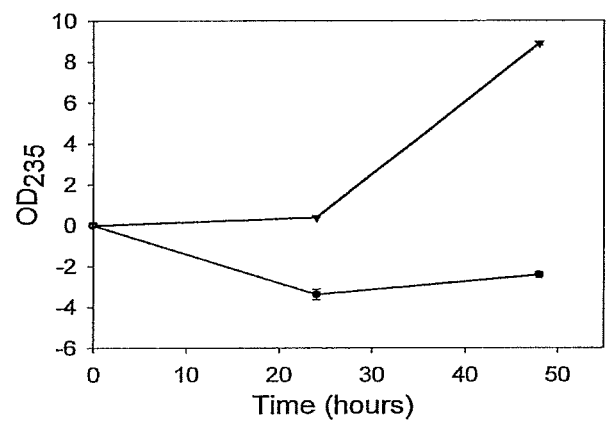

FIG. 10. Comparison of oligogalacturonides with a dp <7 after growth on sugar beet pulp for *E. coli* DH5α with pUC19 (●) or p13C2 (▼).

Figure 11:
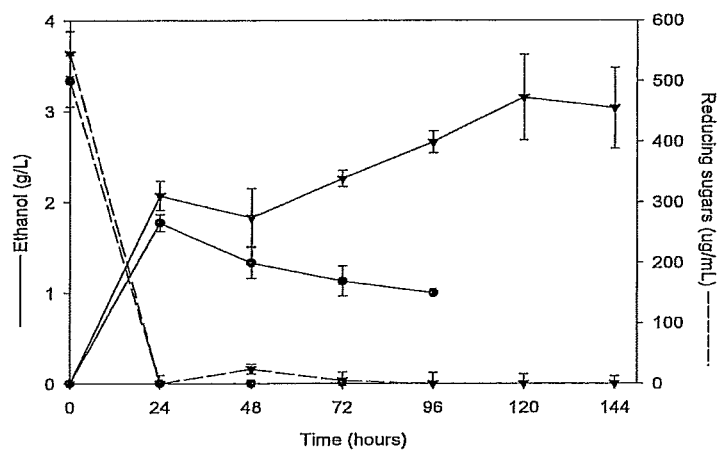

FIG. 11. Ethanol production and reducing sugars from sugar beet pulp fermentation for *E. coli* LY40A (●) and JP27 (▼) (standard error, n=3; solid lines indicate ethanol concentration and dashed line represent reducing sugar concentrations).

FIG. 12. Nucleotide sequence (SEQ ID NO:1) encoding a PelA polypeptide (SEQ ID NO:2), nucleotide sequence (SEQ ID NO:3) encoding a PelB polypeptide (SEQ ID NO:4), and nucleotide sequence (SEQ ID NO:5) encoding an Ogl polypeptide (SEQ ID NO:6).

DETAILED DESCRIPTION OF ILLUSTRATIVE EMBODIMENTS

The present invention includes isolated polypeptides having pectinase activity. One type of polypeptide having pectinase activity is referred to herein as a PelA polypeptide. An example of a PelA polypeptide is depicted at SEQ ID NO:2. Other examples of PelA polypeptides of the present invention include those having sequence similarity with the amino acid sequence of SEQ ID NO:2. A PelA polypeptide having sequence similarity with the amino acid sequence of SEQ ID NO:2 has pectinase activity. A PelA polypeptide may be isolated from a microbe, such as a member of the genera *Paenibacillus*, preferably *P. amylolyticus*, or may be produced using recombinant techniques, or chemically or enzymatically synthesized using routine methods.

The amino acid sequence of a PelA polypeptide having sequence similarity to SEQ ID NO:2 may include conservative substitutions of amino acids present in SEQ ID NO:2. A conservative substitution is typically the substitution of one amino acid for another that is a member of the same class. For example, it is well known in the art of protein biochemistry that an amino acid belonging to a grouping of amino acids having a particular size or characteristic (such as charge, hydrophobicity, and/or hydrophilicity) may generally be substituted for another amino acid without substantially altering the secondary and/or tertiary structure of a polypeptide. Conservative amino acid substitutions can result from exchange of amino acids residues from within one of the following classes of residues: Class I: Gly, Ala, Val, Leu, and Ile (representing aliphatic side chains); Class II: Gly, Ala, Val, Leu, Ile, Ser, and Thr (representing aliphatic and aliphatic hydroxyl side chains); Class III: Tyr, Ser, and Thr (representing hydroxyl side chains); Class IV: Cys and Met (representing sulfur-containing side chains); Class V: Glu, Asp, Asn and Gln (carboxyl or amide group containing side chains); Class VI: His, Arg and Lys (representing basic side chains); Class VII: Gly, Ala, Pro, Trp, Tyr, Ile, Val, Leu, Phe and Met (representing hydrophobic side chains); Class VIII: Phe, Trp, and Tyr (representing aromatic side chains); and Class IX: Asn and Gln (representing amide side chains). The classes are not limited to naturally occurring amino acids, but also include artificial amino acids, such as beta or gamma amino acids and those containing non-natural side chains, and/or other similar monomers such as hydroxyacids. A portion of SEQ ID NO:2 is shown in FIG. 4 in a multiple protein alignment with other pectate lyase class 3 enzymes. Identical amino acids are marked with an asterisk, and conserved and semi-conserved amino acids are marked with colons and dots, respectively.

Guidance concerning how to make phenotypically silent amino acid substitutions is provided in Bowie et al. (1990, Science, 247:1306-1310), wherein the authors indicate proteins are surprisingly tolerant of amino acid substitutions. For example, Bowie et al. disclose that there are two main approaches for studying the tolerance of a polypeptide sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As stated by the authors, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, and the references cited therein.

The present invention also includes isolated polynucleotides encoding a polypeptide of the present invention, e.g., a PelA polypeptide. A polynucleotide encoding a PelA polypeptide is referred to herein as a PelA polynucleotide. PelA polynucleotides may have a nucleotide sequence encoding a polypeptide having the amino acid sequence shown in SEQ ID NO:2. An example of the class of nucleotide sequences encoding such a polypeptide is SEQ ID NO:1. It should be understood that a polynucleotide encoding an PelA polypeptide represented by SEQ ID NO:2 is not limited to the nucleotide sequence disclosed at SEQ ID NO:1, but also includes the class of polynucleotides encoding such polypeptides as a result of the degeneracy of the genetic code. For example, the naturally occurring nucleotide sequence SEQ ID NO:1 is but one member of the class of nucleotide sequences encoding a polypeptide having the amino acid sequence SEQ ID NO:2. The class of nucleotide sequences encoding a selected polypeptide sequence is large but finite, and the nucleotide sequence of each member of the class may be readily determined by one skilled in the art by reference to the standard genetic code, wherein different nucleotide triplets (codons) are known to encode the same amino acid.

A PelA polynucleotide of the present invention may have sequence similarity with the nucleotide sequence of SEQ ID NO:1. PelA polynucleotides having sequence similarity with the nucleotide sequence of SEQ ID NO:1 encode a PelA polypeptide. A PelA polynucleotide may be isolated from a microbe, such as a member of the genera *Paenibacillus*, preferably *P. amylolyticus*, or may be produced using recombinant techniques, or chemically or enzymatically synthesized. A PelA polynucleotide of the present invention may further include heterologous nucleotides flanking the open reading frame encoding the PelA polynucleotide. Typically, heterologous nucleotides may be at the 5' end of the coding region, at the 3' end of the coding region, or the combination thereof. The number of heterologous nucleotides may be, for instance, at least 10, at least 100, or at least 1000.

Another type of polypeptide having pectinase activity is referred to herein as a PelB polypeptide. An example of a PelB polypeptide is depicted at SEQ ID NO:4. Other examples of PelB polypeptides of the present invention include those having sequence similarity with the amino acid sequence of SEQ ID NO:4. A PelB polypeptide having sequence similarity with the amino acid sequence of SEQ ID NO:4 has pectinase activity. A PelB polypeptide may be isolated from a microbe, such as a member of the genera *Paenibacillus*, preferably *P. amylolyticus*, or may be produced using recombinant techniques, or chemically or enzymatically synthesized using routine methods.

The amino acid sequence of a PelB polypeptide having sequence similarity to SEQ ID NO:4 may include conservative substitutions of amino acids present in SEQ ID NO:4. A portion of SEQ ID NO:4 is shown in FIG. 5 in a multiple protein alignment with other pectate lyase class 1 enzymes. Identical amino acids are marked with an asterisk, and conserved and semi-conserved amino acids are marked with colons and dots, respectively. Conserved regions are boxed, residues of sites conserved in all thermostable PL1 pectate lyases are highlighted in grey, conserved catalytic sites are highlighted in black, and conserved calcium binding sites are labeled with the © symbol. Further characteristics of PelB polypeptides are disclosed in Example 4.

The present invention also includes isolated polynucleotides encoding a polypeptide of the present invention, e.g., a PelB polypeptide. A polynucleotide encoding a PelB polypeptide is referred to herein as a PelB polynucleotide. PelB polynucleotides may have a nucleotide sequence encoding a polypeptide having the amino acid sequence shown in SEQ ID NO:4. An example of the class of nucleotide sequences encoding such a polypeptide is SEQ ID NO:3. It should be understood that a polynucleotide encoding a PelB polypeptide represented by SEQ ID NO:4 is not limited to the nucleotide sequence disclosed at SEQ ID NO:3, but also includes the class of polynucleotides encoding such polypeptides as a result of the degeneracy of the genetic code. For example, the naturally occurring nucleotide sequence SEQ ID NO:3 is but one member of the class of nucleotide sequences encoding a polypeptide having the amino acid sequence SEQ ID NO:4. The class of nucleotide sequences encoding a selected polypeptide sequence is large but finite, and the nucleotide sequence of each member of the class may be readily determined by one skilled in the art by reference to the standard genetic code, wherein different nucleotide triplets (codons) are known to encode the same amino acid.

A PelB polynucleotide of the present invention may have sequence similarity with the nucleotide sequence of SEQ ID NO:3. PelB polynucleotides having sequence similarity with the nucleotide sequence of SEQ ID NO:3 encode a PelB polypeptide. A PelB polynucleotide may be isolated from a microbe, such as a member of the genera *Paenibacillus*, preferably *P. amylolyticus*, or may be produced using recombinant techniques, or chemically or enzymatically synthesized. A PelB polynucleotide of the present invention may further include heterologous nucleotides flanking the open reading frame encoding the PelB polynucleotide. Typically, heterologous nucleotides may be at the 5' end of the coding region, at the 3' end of the coding region, or the combination thereof. The number of heterologous nucleotides may be, for instance, at least 10, at least 100, or at least 1000.

Whether a polypeptide has pectinase activity may be determined by in vitro assays. Preferably, an in vitro assay is carried out essentially as described (Collmer et at, 1988, In: Wood & Kellogg (Eds.) *Methods in Enzymology*. San Diego, Calif., Academic Press, Inc., Soriano et al., 2000, *Microbiology*, 146:89-95). Briefly, a polypeptide to be tested for pectinase activity may be expressed in a cell, such as a genetically modified microbial cell, and a cell extract may be prepared by, for instance, sonication. A standard enzyme assay mixture may include 0.2% weight/volume (w/v) of the substrate. Suitable substrates include unesterified polygalacturonic acid or an esterified pectin. Examples of suitable esterified pectins include those having between 8.5% and 90% esterification. The substrate may be present in a final volume of 1 mL of 50 mM glycine buffer containing $CaCl_2$. The pH of the buffer may be between 9 and 10.5; however, when the polypeptide has sequence similarity to a PelA polypeptide the pH may be between 10.25 and 10.75, such as 10.5, and when the polypeptide has sequence similarity to a PelB polypeptide the pH may be between 9.25 and 9.75, such as 9.5. The $CaCl_2$ concentration may be between 0.3 mM and 1.75 mM; however, when the polypeptide has sequence similarity to a PelA polypeptide the $CaCl_2$ concentration may be between 1.25 mM and 1.75 mM, such as 1.5 mM, and when the polypeptide has sequence similarity to a PelB polypeptide the $CaCl_2$ concentration may be between 0.3 mM and 0.7 mM, such as 0.5 mM. The assay mixture and enzyme preparation may be equilibrated to an appropriate temperature and monitored for the formation of $\Delta$-4,5-unsaturated products at 235 nm for 1 to 3 min. The temperature of the reaction may be between 40° C. and 57° C.; however, when the polypeptide has sequence similarity to a PelA polypeptide the temperature may be between 42° C. and 47° C., such as 45° C., and when the polypeptide has sequence similarity to a PelB polypeptide the temperature may be between 53° C. and 57° C., such as 55° C. One unit of enzyme activity is defined as the amount of enzyme that produces 1 μmol 4,5-unsaturated product per minute.

The present invention also includes fragments of the polypeptides described herein, and the polynucleotides encoding such fragments, PelA polypeptides and PelB polypeptides, such as SEQ ID NOs:2 and 4, respectively. A polypeptide fragment may include a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 amino acid residues.

A polypeptide of the present invention or a fragment thereof may be expressed as a fusion polypeptide that includes a polypeptide of the present invention or a fragment thereof and an additional amino acid sequence. For instance, the additional amino acid sequence may be useful for purification of the fusion polypeptide by affinity chromatography. Various methods are available for the addition of such affinity purification moieties to proteins. Representative examples may be found in Hopp et al. (U.S. Pat. No. 4,703,004), Hopp et al. (U.S. Pat. No. 4,782,137), Sgarlato (U.S. Pat. No. 5,935, 824), and Sharma (U.S. Pat. No. 5,594,115). In another example, the additional amino acid sequence may be a carrier polypeptide. The carrier polypeptide may be used to increase the immunogenicity of the fusion polypeptide to increase production of antibodies that specifically bind to a polypeptide of the invention. The invention is not limited by the types of carrier polypeptides that may be used to create fusion polypeptides. Examples of carrier polypeptides include, but are not limited to, keyhole limpet hemacyanin, bovine serum albumin, ovalbumin, mouse serum albumin, rabbit serum albumin, and the like.

Another example of an additional amino acid sequence is a secretory sequence. In certain embodiments, for instance, where a polynucleotide encoding a PelA polypeptide of the present invention or a fragment thereof, a PelB polypeptide or a fragment thereof, or a combination thereof is expressed in a prokaryotic cell, the polypeptide may include a signal sequence that is present at the amino terminal end. The signal sequence targets the polypeptide for export out of the cytoplasm of the cell. Signal sequences that function in eukaryotic cells and in prokaryotic cells are known to the skilled person and are used routinely to engineer polypeptides for export.

A polynucleotide of the present invention may be present in a vector. A vector is a replicating polynucleotide, such as a plasmid, phage, or cosmid, to which another polynucleotide may be attached so as to bring about the replication of the attached polynucleotide. Construction of vectors containing a polynucleotide of the invention employs standard ligation techniques known in the art. See, e.g., Sambrook et al, Molecular Cloning: A Laboratory Manual., Cold Spring Harbor Laboratory Press (1989). A vector may provide for further cloning (amplification of the polynucleotide), i.e., a cloning vector, or for expression of the polynucleotide, i.e., an expression vector. The term vector includes, but is not limited to, plasmid vectors, viral vectors, cosmid vectors, and artificial chromosome vectors. Examples of viral vectors include, for instance, lambda phage vectors, P1 phage vectors, M13 phage vectors, adenoviral vectors, adeno-associated viral vectors, lentiviral vectors, retroviral vectors, and herpes virus vectors. Typically, a vector is capable of replication in a microbial host, for instance, a fungus, such as *S. cerevisiae*, or a prokaryotic bacterium, such as *E. coli*. Preferably the vector is a plasmid.

Selection of a vector depends upon a variety of desired characteristics in the resulting construct, such as a selection marker, vector replication rate, and the like. In some aspects, suitable host cells for cloning or expressing the vectors herein include eukaryotic cells. Suitable eukaryotic cells include fungi, such as *S. cerevisiae* and *P. pastoris*. In other aspects, suitable host cells for cloning or expressing the vectors herein include prokaryotic cells. Suitable prokaryotic cells include eubacteria, such as gram-negative microbes, for example, *E. coli*. Vectors may be introduced into a host cell using methods that are known and used routinely by the skilled person. For example, calcium phosphate precipitation, electroporation, heat shock, lipofection, microinjection, and viral-mediated nucleic acid transfer are common methods for introducing nucleic acids into host cells.

Polynucleotides of the present invention may be obtained from microbes, for instance, members of the genus *Paenibacillus*, such as *P. amylolyticus*. Members of the genus *Paenibacillus* useful in the methods disclosed herein may be obtained from soil, such as soil containing organic material, for example rice fields, food products (Yoshikatsu et al., 2006, Biocontro. Sci., 11:43-47; Kim et al., 2009, Int. J. Syst. Evol. Microbiol., 59:1002-1006), or the digestive tract of insects that have a diet that includes lignocellulosic biomass, for instance, termites, honeybee (Neuendorf et al., 2004, Microbiol., 150:2381-2390), and *Tipula abdominalis* (Cook et al., 2007, Appl. Environ. Microbiol., 73:5683-5686). Polynucleotides of the present invention may be produced in vitro or in vivo. For instance, methods for in vitro synthesis include, but are not limited to, chemical synthesis with a conventional DNA/RNA synthesizer. Commercial suppliers of synthetic polynucleotides and reagents for such synthesis are well known. Likewise, polypeptides of the present invention may be obtained from microbes, or produced in vitro or in vivo.

An expression vector optionally includes regulatory sequences operably linked to the coding region. The invention is not limited by the use of any particular promoter, and a wide variety of promoters are known. Promoters act as regulatory signals that bind RNA polymerase in a cell to initiate transcription of a downstream (3' direction) coding region. The promoter used may be a constitutive or an inducible promoter. It may be, but need not be, heterologous with respect to the host cell. Examples of promoters include, but are not limited to, promoters that function in anaerobic conditions and promoters that are not subject to inhibition by glucose.

An expression vector may optionally include a ribosome binding site and a start site (e.g., the codon ATG) to initiate translation of the transcribed message to produce the polypeptide. It may also include a termination sequence to end translation. A termination sequence is typically a codon for which there exists no corresponding aminoacetyl-tRNA, thus ending polypeptide synthesis. The polynucleotide used to transform the host cell may optionally further include a transcription termination sequence.

A vector introduced into a host cell optionally includes one or more marker sequences, which typically encode a molecule that inactivates or otherwise detects or is detected by a compound in the growth medium. For example, the inclusion of a marker sequence may render the transformed cell resistant to an antibiotic, or it may confer compound-specific metabolism on the transformed cell. Examples of a marker sequence are sequences that confer resistance to kanamycin, ampicillin, chloramphenicol, tetracycline, and neomycin.

The present invention also includes antibodies that specifically bind a polypeptide of the present invention. An antibody that specifically binds a PelA polypeptide of the present invention, preferably, SEQ ID NO:2 or a fragment thereof, does not bind to a pectate lyase expressed by *P. barcinonensis*, and described at Genbank accession number CAB40884. An antibody that specifically binds a PelB polypeptide of the present invention, preferably, SEQ ID NO:4 or a fragment thereof, does not bind to a pectate lyase expressed by *Bacillus* sp. YA-14, and described at Genbank accession number BAA05383.

Antibody may be produced using a polypeptide of the present invention, or a fragment thereof. The antibody may be polyclonal or monoclonal. Laboratory methods for producing, characterizing, and optionally isolating polyclonal and monoclonal antibodies are known in the art (see, for instance, Harlow E. et al., 1988, Antibodies: A laboratory manual, Cold Spring Harbor Laboratory Press, Cold Spring Harbor. For instance, a polypeptide of the present invention may be administered to an animal, preferably a mammal, in an amount effective to cause the production of antibody specific for the administered polypeptide. Optionally, a polypeptide may be mixed with an adjuvant, for instance Freund's incomplete adjuvant, to stimulate the production of antibodies upon administration. Whether an antibody of the present invention specifically binds to a polypeptide of the present invention may be determined using methods known in the art. For instance, specificity may be determined by testing antibody binding to SEQ ID NO:2 and a polypeptide having the amino acid sequence described at Genbank accession number CAB40884. Other examples include testing the kinetics of antibody binding to different polypeptides, and testing competition in binding using as competitors known polypeptides containing or not containing an epitope against which the antibody is directed.

The present invention also includes genetically modified microbes and compositions that include genetically modified microbes. In some embodiments a genetically modified microbe has a polynucleotide encoding a polypeptide having pectinase activity, such as a PelA polypeptide, a PelB polypeptide, or a combination thereof. Compared to a control microbe that is not genetically modified, a genetically modified microbe may exhibit production of a PelA polypeptide or a fragment thereof, production of a PelB polypeptide or a fragment thereof, or the combination thereof. A polynucleotide encoding a PelA polypeptide, a PelB polypeptide, or a combination thereof, may be present in the microbe as a vector or integrated into a chromosome.

Examples of microbes that can be genetically modified to encode a polypeptide having pectinase activity include, but are not limited to, microbes known to be capable of producing cellulolytic enzymes, e.g., species of *Humicola, Coprinus, Thielavia, Fusarium, Myceliophthora, Acremonium, Cephalosporium, Scytalidium, Penicillium* or *Aspergillus* (see, for example, Shun-Ichi et al., U.S. Pat. No. 5,258,297), especially those produced by a strain selected from the species *Humicola insolens* (reclassified as *Scytalidium thermophilum*, see for example, Barbesgaard et al., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum*, and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Trichoderma* (particularly *Trichoderma viride, Trichoderma reesei*, and *Trichoderma koningii*), alkalophilic *Bacillus* (see, for example, Horikoshi et al., U.S. Pat. No. 3,844,890 and Shun-Ichi et al., U.S. Pat. No. 5,258,297), and *Streptomyces* (see, for example, Shun-Ichi et al., U.S. Pat. No. 5,258,297).

Examples of microbes that can be genetically modified to encode a polypeptide having pectinase activity include, but are not limited to, microbes known to be capable of producing ethanol. Useful eukaryotic cells include, but are not limited to, *Saccharomyces* (such as *Saccharomyces cerevisiae*), and *Pichia* (such as *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica*).

Examples of *S. cerevisiae* include, but are not limited to, Baker's yeast, Tembec T1 (Keating et al., 2004, J. Ind. Microbiol. Biotechnol. 31:235), Y-1528 (Keating et al., 2004, J. Ind. Microbiol. Biotechnol. 31:235), TMB3000 (Alkasrawi et al., 2006, Enzyme Microb. Tech., 38:279), CBS 8066, CEN/PK 113-7D, TMB3500, USM21, and NRRL Y-12632. Examples of *Pichia stipitis* include, but are not limited to, NRRL Y-7124. Other examples of commercially available yeast which can be used include, for instance, RED STAR and ETHANOL RED yeast (available from Fermentis/Lesaffie, USA), FALI (available from Fleischmann's Yeast, USA), SUPERSTART and THERMOSACC fresh yeast (available from Ethanol Technology, Wis., USA), BIOFERM AFT and XR (available from NABC—North American Bioproducts Corporation, Ga., USA), GERT STRAND (available from Gert Strand AB, Sweden), and FERMIOL (available from DSM Specialties).

Examples of prokaryotic ethanologenic microbes include, but are not limited to, *Escherichia*, in particular *Escherichia coli*, members of the genus *Zymomonas*, in particular *Zymomonas mobilis*, members of the genus *Zymobacter*, in particular *Zymobactor palmae*, members of the genus *Klebsiella*, in particular *Klebsiella oxytoca*, members of the genus *Leuconostoc*, in particular *Leuconostoc mesenteroides*, members of the genus *Lactobacillus*, in particular *Lactobacillus helveticus* and *Lactobacillus delbruckii*, members of the genus *Lactococcus*, in particular *Lactococcus lactic*, members of the genus *Clostridium*, in particular *Clostridium butyricum*, members of the genus *Enterobacter*, in particular *Enterobacter aerogenes*, and members of the genus *Thermoanaerobacter*, in particular *Thermoanaerobacter* BG1L1, *Thermoanarobacter ethanolicus, Thermoanaerobacter thermosaccharolyticum*, or *Thermoanaerobacter mathranii*. Examples of *E. coli* include, but are not limited to, KO11, LY01.

A genetically modified microbe of the present invention may include other modifications. For instance, a genetically modified microbe of the present invention may include other modifications that provide for increased ability to use renewable resources, such as lignocellulosic biomass, for the production of desired metabolic products, such as commodity chemicals. Modifications may provide for increased production of commodity chemicals by, for instance, increasing production of enzymes in metabolic pathways, reducing feedback inhibition at different locations in metabolic pathways, increasing importation of substrates used in metabolic pathways to produce a commodity chemical, and/or increasing secretion of polypeptides. Polypeptides involved in the degradation of polysaccharides to glucose, xylose, mannose, galactose, and arabinose include, for instance, endoglucanases, cellobiohydrolases, glucohydrolases, beta-glucosidases, methylesterases, depolymerases, pectin and pectate lyases, and cellobioases (e.g., casAB coding regions, such as those described at Genbank accession U61727).

Polypeptides involved in producing metabolic products, such as commodity chemicals, can vary with the chemical being produced, and may include those useful when the substrate includes a 6-carbon sugar and/or a 5-carbon sugar. For instance, when lactic acid is to be produced the genetically modified microbe may include polynucleotides encoding a lactate dehydrogenase that catalyses the formation of L-(+) or D-(−) lactic acid. When ethanol is to be produced the genetically modified microbe may include polynucleotides encoding a pyruvate decarboxylase, an alcohol dehydrogenase, and/or a phosphotransferase (Ingram et al., U.S. Pat. No. 6,102,690, Ingram et at, U.S. Pat. No. 7,026,152). Under anaerobic conditions pyruvate is converted to acetyl CoA, catalysed by the enzyme pyruvate formate lyase (PFL). Acetyl CoA is subsequently converted into acetaldehyde by the enzyme acetaldehyde dehydrogenase (AcDH) and ethanol is produced by the reduction of acetaldehyde catalyzed by ADH. When butanol is to be produced the genetically modified microbe may include polynucleotides encoding a 3-hydroxybutyryl-CoAdehydrogen-ase, a crotonase, a butyryl-CoAdehydrogenase, and/or an aldehyde/alcoholdehydrogenase (Atsnmi et at, 2008, Metabolic Engineering, 10:305-311). A genetically modified microbe may be engineered to include exogenous polynucleotides encoding useful enzymes, or endogenous polynucleotides may be modified, for instance, to increase expression of an endogenous coding region. Metabolic pathways of microbes are known to the skilled person and metabolic engineering to modify the production metabolic products is routinely practiced. Coding regions encoding polypeptides involved in metabolic pathways are also known to the skilled person and readily available.

In other aspects, modifications can include disrupting the activity of one or more endogenous coding regions in a way that inhibits the production of non-desired metabolic products and/or redirects the metabolism of intermediates toward the production of desired metabolic products. Examples of modifications that disrupt a metabolic pathway include, for example, "knock out" mutations that significantly reduce or eliminate biological activity of the mutated coding region (and/or the polypeptide encoded by the mutated coding region). Methods for introducing knock out mutations in many cellular models are routine and known to those skilled in the art. In other words, one may direct metabolism toward pathways that produce desired products by reducing or eliminating metabolism via pathways that compete with the desired pathway for metabolic resources.

In those embodiments where a genetically modified microbe includes a pectinase, such as a PelA polypeptide or a fragment thereof, or a PelB polypeptide or a fragment thereof, the genetically modified microbe may also include a polynucleotide encoding an enzyme having oligogalacturonate activity. One type of polypeptide having oligogalacturonate activity is referred to herein as an oligogalacturonide lyase (Ogl) polypeptide (Reverchon et al., 1989, Gene, 85:125-134, Shevchik et al., 1999, J. Bacteriol., 181:3912-3919). Ogl polypeptides are known to the art, and an example of an oligogalacturonide lyase is described at Genbank Accession number AAA24825 (SEQ ID NO:6). Other examples of Ogl polypeptides of the present invention include those having sequence similarity with the amino acid sequence of SEQ ID NO:6. An Ogl polypeptide having sequence similarity with the amino acid sequence of SEQ ID NO:6 has oligogalacturonate activity. The amino acid sequence of an Ogl polypeptide having sequence similarity to SEQ ID NO:6 may include conservative substitutions of amino acids present in SEQ ID NO:6. Methods for detecting and measuring oligogalacturonate activity using direct UV detection are known to the skilled person and routinely used (Shevchik et al., 1999, J. Bacteriol., 181:3912-3919).

A polynucleotide encoding an Ogl polypeptide is referred to herein as an Ogl polynucleotide. Ogl polynucleotides may have a nucleotide sequence encoding a polypeptide having the amino acid sequence shown in SEQ ID NO:6. An example of the class of nucleotide sequences encoding such a polypeptide is SEQ ID NO:5. It should be understood that a polynucleotide encoding an Ogl polypeptide represented by SEQ ID NO:6 is not limited to the nucleotide sequence disclosed at SEQ ID NO:5, but also includes the class of polynucleotides encoding such polypeptides as a result of the degeneracy of the genetic code. For example, the naturally occurring nucleotide sequence SEQ ID NO:5 is but one member of the class of nucleotide sequences encoding a polypeptide having the amino acid sequence SEQ ID NO:6.

An Ogl polynucleotide of the present invention may have sequence similarity with the nucleotide sequence of SEQ ID NO:5. Ogl polynucleotides having sequence similarity with the nucleotide sequence of SEQ ID NO:5 encode an Ogl polypeptide. An Ogl polynucleotide may be isolated from a microbe, such as a member of the genera Erwinia, preferably Erwinia chrysanthemi, or may be produced using recombinant techniques, or chemically or enzymatically synthesized. An Ogl polynucleotide may further include heterologous nucleotides flanking the open reading frame encoding the Ogl polynucleotide.

A genetically modified microbe of the present invention may include other modifications that provide for export of a polypeptide from the cytoplasm of a cell to the exterior of the cell. In some embodiments, such modifications include the addition of polynucleotides encoding polypeptides that act to impart secretory activity to a gram-negative cell. Examples of secretory systems in gram-negative microbes include Type I, Type II, Type III, Type IV, and the Type VI secretion systems. Examples of useful secretory systems include, but are not limited to, the out system present in Erwinia spp., or the pul system present in Klebsiella spp. (Pugsley et al., 1993, Microbiological Reviews, 57:50-108; Lindeberg et al., 1996, Mol. Micro., 20:175-190; Lindeberg et al., 1992, J. Bacteriol., 174:7385-7397; He et al., 1991, Proc. Natl. Acad. Sci. USA, 88:1079-1083). The introduction of one or more secretory polypeptides into a genetically modified microbe may result in an increase in the secretion of the selected polypeptide, e.g., a pectinase, as compared to secretion of the polypeptide in the cell without the secretory polypeptides. The increase in secretion may be at least 10%, at least 100%, at least 200%, at least 300%, at least 400%, at least 500%, at least 600%, at least 700%, at least 800%, at least 900%, or at least 1000%, as compared to levels of secretion in the cell without the secretory polypeptides.

Also included in the present invention are methods of making the polypeptides, polynucleotides, and genetically modified microbes described herein. Polypeptides may be obtained from a microbe that naturally produces a polypeptide of the present invention, for instance, a Paenibacillus spp., such as P. amylolyticus. Alternatively, a genetically modified microbe may be used. The methods may include culturing a microbe under conditions suitable for expression of the polypeptide, and recovering the polypeptide. The polypeptide may be recovered from the culture medium by conventional procedures including separating the cells from the medium by centrifugation or filtration, or if necessary, disrupting the cells and separating the supernatant from the cellular fragments and debris. Typically, the proteinaceous components of the supernatant or filtrate are precipitated by means of a salt, e.g., ammonium sulfate. Optionally, the precipitated polypeptides may be solubilized and isolated or purified by a variety of chromatographic procedures, e.g., ion exchange chromatography, affinity chromatography or another similarly art-recognized procedure. Polypeptides and fragments thereof useful in the present invention may be produced using recombinant DNA techniques, such as an expression vector present in a cell. Such methods are routine and known in the art. The polypeptides and fragments thereof may also be synthesized in vitro, e.g., by solid phase peptide synthetic methods. The solid phase peptide synthetic methods are routine and known in the art. A polypeptide produced using recombinant techniques or by solid phase peptide synthetic methods may be further purified by routine methods, such as fractionation on immunoaffinity or ion-exchange columns, ethanol precipitation, reverse phase HPLC, chromatography on silica or on an anion-exchange resin such as DEAE, chromatofocusing, SDS-PAGE, ammonium sulfate precipitation, gel filtration using, for example, Sephadex G-75, or ligand affinity. Also included in the present invention are compositions that include a PelA polypeptide or a fragment thereof, or a PelB polypeptide or a fragment thereof.

Provided herein are methods for using the polypeptides, polynucleotides, and genetically modified microbes described herein. In one embodiment, the methods include degrading pectin to produce metabolic products. Methods for degrading pectin to produce metabolic products may include culturing a genetically engineered microbe described herein in a composition that includes pectin under conditions suitable for degrading the pectin. Typically, the pectin is present in a lignocellulosic material. Any suitable lignocellulosic material is contemplated in context of the present methods. Lignocellulosic material may be any material containing lignocellulose and pectin. In some aspects, the lignocellulosic material contains at least 40 wt %, at least 50 wt %, at least 60 wt %, at least 70 wt %, at least 80 wt %, at least 90 wt % lignocellulose. It is to be understood that the lignocellulosic material may also include other constituents such as cellulosic material, such as cellulose, hemicellulose, and may also include constituents such as sugars, such as fermentable sugars and/or un-fermentable sugars.

Ligmocellulosic material useful in the methods described herein is generally found, for example, fruits, such as apple, pear, grape, strawberry, raspberry, blackberry, apricot, mango, guava, papaya, pineapple, and banana, and members of the genus Citrus, such as lemon, lime, orange, tangerine, grapefruit. Sources of lignocellulosic materials include other plants such as vegetables, including sugar beets, soy beans, carrots, tomatoes, and the like. Other examples of lignocellulosic material useful in the methods described herein include agricultural residues, such as wheat straw, corn stover, pulps such as citrus pulp and sugar beet pulp, and pomace. It is understood that lignocellulose material may be in the form of plant cell wall material containing lignin, cellulose, hemicellulose, and pectin in a mixed matrix.

The pectin may be unesterified, or may be esterified. If the pectin is esterified, the level of esterification may be at least 8.5%, at least 20%, at least 30%, at least 40%, at least 50%, at least 60%, at least 70%, or at least 80%, no greater than 90%, no greater than 80%, no greater than 70%, no greater than 60%, no greater than 50%, no greater than 40%, or no greater than 30%, or a combination thereof.

A process of producing a metabolic product from lignocellulosic materials may include pretreatment, enzymatic hydrolysis through the use of enzymes such as cellulases, fermentation, and/or recovery of the metabolic product. The process may also include, for instance, separation of the sugar solution from residual materials such as lignin.

Biomass from agricultural residues, like sugar beet pulp, may not require thermochemical or mechanical pretreatments because they are already partially processed; however, in certain embodiments pretreatment may be desirable. There are numerous pretreatment methods or combinations of pretreatment methods known in the art and routinely used. Physical pretreatment breaks down the size of lignocellulosic material by milling or aqueous/steam processing. Chipping or grinding may be used to typically produce particles between 0.2 and 30 mm in size. Methods used for lignocelluosic materials typically require intense physical pretreatments such as steam explosion and other such treatments (Peterson et al., U.S. Patent Application 20090093028). The most common chemical pretreatment methods used for lignocellulosic materials include dilute acid, alkaline, organic solvent, ammonia, sulfur dioxide, carbon dioxide or other chemicals to make the biomass more available to enzymes. Biological pretreatments are sometimes used in combination with chemical treatments to solubilize the lignin in order to make cellulose more accessible to hydrolysis and fermentation.

Steam explosion is a common method for pretreatment of lignocellulosic biomass and increases the amount of cellulose available for enzymatic hydrolysis (Foody, U.S. Pat. No. 4,461,648). Generally, the material is treated with high-pressure saturated steam and the pressure is rapidly reduced, causing the materials to undergo an explosive decompression. Steam explosion is typically initiated at a temperature of 160-260° C. for several seconds to several minutes at pressures of up to 4.5 to 5 MPa. The biomass is then exposed to atmospheric pressure. The process typically causes hemicellulose degradation and lignin transformation. Addition of $H_2SO_4$, $SO_2$, or $CO_2$ to the steam explosion reaction can improve subsequent cellulose hydrolysis, decrease production of inhibitory compounds and lead to the more complete removal of hemicellulose (Morjanoff and Gray, 1987, Biotechnol. Bioeng. 29:733-741).

In ammonia fiber explosion (AFEX) pretreatment, biomass is treated with approximately 1-2 kg ammonia per kg dry biomass for approximately 30 minutes at pressures of 1.5 to 2 MPa. (Dale, U.S. Pat. No. 4,600,590; Dale, U.S. Pat. No. 5,037,663; Mes-Hartree, et al. 1988, Appl. Microbiol. Biotechnol., 29:462-468). Like steam explosion, the pressure is then rapidly reduced to atmospheric levels, boiling the ammonia and exploding the lignocellulosic material. APEX pretreatment appears to be especially effective for biomass with a relatively low lignin content, but not for biomass with high lignin content such as newspaper or aspen chips (Sun and Cheng, 2002, Bioresource Technol., 83:1-11).

Concentrated or dilute acids may also be used for pretreatment of lignocellulosic biomass. $H_2SO_4$ and HCl have been used at high concentrations, for instance, greater than 70%. In addition to pretreatment, concentrated acid may also be used for hydrolysis of cellulose (Hester et al., U.S. Pat. No. 5,972,118). Dilute acids can be used at either high (>160° C.) or low (<160° C.) temperatures, although high temperature is preferred for cellulose hydrolysis (Sun and Cheng, 2002, Bioresource Technol., 83:1-11). $H_2SO_4$ and HCl at concentrations of 0.3 to 2% (wt/wt) and treatment times ranging from minutes to 2 hours or longer can be used for dilute acid pretreatment.

Other pretreatments include alkaline hydrolysis (Qian et al., 2006, Appl. Biochem. Biotechnol., 134:273; Galbe and Zacchi, 2002, Appl. Microbiol. Biotechnol., 59:618), oxidative delignification, organosolv process (Pan et al., 2005, Biotechnol. Bioeng., 90:473; Pan et al., 2006, Biotechnol. Bioeng., 94:851; Pan et al., 2006, J. Agric. Food Chem., 54:5806; Pan et al., 2007, Appl. Biochem. Biotechnol., 137-140:367), or biological pretreatment.

Some of the pretreatment processes described above include hydrolysis of the hemicellulose and cellulose to monomer sugars. Others, such as organosolv, prepare the substrates so that they will be susceptible to hydrolysis. This hydrolysis step can in fact be part of the fermentation process if some methods, such as simultaneous saccharification and fermentation (SSF), is used. Otherwise, the pretreatment may be followed by enzymatic hydrolysis with cellulases.

A cellulase may be any enzyme involved in the degradation of lignocellulose to glucose, xylose, mannose, galactose, and arabinose. The cellulolytic enzyme may be a multicomponent enzyme preparation, e.g., cellulase, a monocomponent enzyme preparation, e.g., endoglucanase, cellobiohydrolase, glucohydrolase, beta-glucosidase, or a combination of multicomponent and monocomponent enzymes. The cellulolytic enzymes may have activity, e.g., hydrolyze cellulose, either in the acid, neutral, or alkaline pH-range.

A cellulase may be of fungal or bacterial origin, which may be obtainable or isolated from microorganisms which are known to be capable of producing cellulolytic enzymes. Examples of such microbes are described herein. Useful cellulases may be produced by fermentation of the above-noted microbial strains on a nutrient medium containing suitable carbon and nitrogen sources and inorganic salts, using procedures known in the art.

Examples of cellulases suitable for use in the present invention include, for example, CELLUCLAST (available from Novozymes A/S) and NOVOZYME (available from Novozymes A/S). Other commercially available preparations including cellulase which may be used include CELLUZYME, CEREFLO and ULTRAFLO (Novozymes A/S), LAMINEX and SPEZYME CP (Genencor Int.), and ROHAMENT 7069 W (Rohm GmbH).

The hydrolysis/fermentation of lignocellulosic materials may, and typically does, require addition of cellulases (e.g., cellulases available from Novozymes A/S). Typically, cellulase enzymes may be added in amounts effective from 5 to 35 filter paper units of activity per gram of substrate, or 0.001% to 5.0% wt. of solids. The amount of cellulases appropriate for the hydrolysis may be decreased by using a genetically modified microbe described herein. For instance, a genetically modified microbe that expresses a pectinase and a cellulase, such as cellobiase, will degrade polysaccharides such as pectin and cellobiose (a glucose disaccharide formed during saccharification) to result in substrate for the genetically modified microbe to produce desirable metabolic products, thus requiring addition of less cellulases compared to the same microbe without the modifications. The amount of cellulases (e.g., cellulases available from Novozymes A/S) required for hydrolysis of the pretreated lignocellulosic material may be decreased by at least 5%, at least 10%, at least 15%, at least 20%, at least 25%, or at least 30%. This decreased need for cellulases can result in a significant decrease in costs associated with producing metabolic products from lignocellulosic materials.

The steps following pretreatment, e.g., hydrolysis and fermentation, can be performed separately or simultaneously. Conventional methods used to process the lignocellulosic material in accordance with the methods disclosed herein are well understood to those skilled in the art. Detailed discussion of methods and protocols for the production of ethanol from biomass are reviewed in Wyman (1999, Annu. Rev. Energy Environ., 24:189-226), Gong et al. (1999, Adv. Biochem. Engng. Biotech., 65: 207-241), Sun and Cheng (2002, Bioresource Technol., 83:1-11), and Olsson and Hahn-Hagerdal (1996, Enzyme and Microb. Technol., 18:312-331). The methods of the present invention may be implemented using any conventional biomass processing apparatus (also referred to herein as a bioreactor) configured to operate in accordance with the invention. Such an apparatus may include a batch-stirred reactor, a continuous flow stirred reactor with ultrafiltration, a continuous plug-flow column reactor (Gusakov, A. V., and Sinitsyn, A. P., 1985, Enz. Microb. Technol., 7: 346-352), an attrition reactor (Ryu, S. K., and Lee, J. M., 1983, Biotechnol. Bioeng., 25: 53-65), or a reactor with intensive stirring induced by an electromagnetic field (Gusakov, A. V., Sinitsyn, A. P., Davydkin, I. Y., Davydkin, V. Y., Protas, O. V., 1996, Appl. Biochem. Biotechnol., 56: 141-153). Smaller scale fermentations may be conducted using, for instance, a flask or a fleaker.

The conventional methods include, but are not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC). The fermentation can be carried out by batch fermentation or by fed-batch fermentation.

SHF uses separate process steps to first enzymatically hydrolyze cellulose to glucose and then ferment glucose to ethanol. In SSF, the enzymatic hydrolysis of cellulose and the fermentation of glucose to ethanol are combined in one step (Philippidis, G. P., 1996, Cellulose bioconversion technology, in Handbook on Bioethanol: Production and Utilization, Wyman, C. E., ed., Taylor & Francis, Washington, D.C., 179-212). SSCF includes the coferementation of multiple sugars (Sheehan, J., and Himmel, M., 1999, Enzymes, energy and the environment: A strategic perspective on the U.S. Department of Energy's research and development activities for bioethanol, Biotechnol. Prog., 15: 817-827). HHF includes two separate steps carried out in the same reactor but at different temperatures, i.e., high temperature enzymatic saccharification followed by SSF at a lower temperature that the fermentation strain can tolerate. DMC combines all three processes (cellulase production, cellulose hydrolysis, and fermentation) in one step (Lynd, L. R., Weimer, P. J., van Zyl, W. H., and Pretorius, I. S., 2002, Microbiol. Mol. Biol. Reviews, 66: 506-577).

The final step may be recovery of the metabolic product. The method depends upon the metabolic product that is to be recovered, and methods for recovering metabolic products resulting from microbial fermentation of lignocellulosic material are known to the skilled person and used routinely. For instance, when the metabolic product is ethanol, the ethanol may be distilled using conventional methods. For example, after fermentation the metabolic product, e.g., ethanol, may be separated from the fermented slurry. The slurry may be distilled to extract the ethanol, or the ethanol may be extracted from the fermented slurry by micro or membrane filtration techniques. Alternatively the fermentation product may be recovered by stripping.

Also provided herein are methods for using the polypeptides described herein. The methods typically include contacting a lignocellulosic material with a polypeptide described herein, such as a PelA polypeptide, a PelB polypeptide, or a fragment thereof, under conditions suitable for the degradation of pectin. The conditions may be alkaline, such as pH 9 to 10.5. The polypeptide may be used in combination with other carbohydrate degrading enzymes, such as arabinanase and/or xyloglucanase, as well as other pectinases. The polypeptides described herein are useful in processing of materials, such as the pretreatment of lignocellulosic material to prepare for the production of metabolic products, decreasing viscosity of solutions containing pectin, clarifying solutions such as fruit juices, retting and/or degumming of fiber crops such as hemp, flax, or linen, treatment of pectic wastewater, production of Japanese paper, paper making, and oil extraction from oil-rich plant material, such as soy-bean oil from soy-beans, olive-oil from olives or rapeseed-oil from rape-seed or sunflower oil from sunflower (Hoondal et al., 2002, Appl. Microbiol. Biotechnol., 59:409-418, Kashyap et al., 2001, Bioresour. Technol., 77:215-227). The polypeptides described herein may be used for the preparation of fibers or for cleaning of fibers, typically in combination with detergents. Cotton fibers consist of a primary cell wall layer containing pectin and a secondary layer containing mainly cellulose (Andersen et al., U.S. Pat. No. 7,273,745). During cotton preparation or cotton refining part of the primary cell wall may be removed. The polypeptides disclosed herein may be used as an aid during cotton refining by removal of the primary cell wall or during cleaning of the cotton to remove residual pectic substances and prevent graying of the textile.

The above summary of the present invention is not intended to describe each disclosed embodiment or every implementation of the present invention. The description that follows more particularly exemplifies illustrative embodiments. In several places throughout the application, guidance is provided through lists of examples, which examples can be

Example 1

Ethanologen *Escherichia coli* KO11 was sequentially engineered to produce the *Klebsiella oxytoca* EnzymeII$^{cellulose}$ and phospho-βglucosidase genes (casAB) as well as a pectate lyase (pelE) from *Erwinia chrysanthemi*, yielding strains LY40A (casAB) and JP07 (casAB; pelE), respectively. To obtain effective secretion of PelE, the Sec-independent pathway out genes from *E. chrysanthemi* on the cosmid pCPP2006 were provided to strain JP07 to construct strain JP07C. *E. coli* strains LY40A, JP07, and JP07C possessed significant cellobiase activity in cell lysates, while only strain JP07C demonstrated extracellular pectate lyase activity. Fermentation with sugar beet pulp at very low fungal enzyme loads during saccharification revealed significantly higher ethanol production for LY40A and JP07C compared to KO11. While JP07C ethanol yields were not considerably higher than LY40A, investigation of oligogalacturonate polymerization showed an increased breakdown of biomass to small chain (degree of polymerization ≤6) oligogalacturonides. Further engineering of *E. coli* JP07C to express Ogl, an oligogalacturonide lyase also from *E. chrysanthemi*, achieved even further breakdown of polygalacturonate to monomeric sugars and lead to higher ethanol yields.

Materials and Methods

Bacterial strains and media. Bacterial strains, plasmids, and oligonucleotides used in this study are listed in Table 1. *E. coli* strains were grown at 37° C. in Luria-Bertani (LB) medium supplemented with 2% wt/vol glucose for ethanologenic strains. When indicated, antibiotics were used at the following concentrations unless otherwise stated: chloramphenicol (Cm), 40 mg/L; ampicillin (Ap), 50 mg/L; kanamycin (Kn), 40 mg/L; erythromycin (Em), 150 mg/L; and spectinomycin (Spc), 50 mg/L. For enzyme assays, ethanologenic *E. coli* were grown in minimal media (MM) (Atlas, et al., 1993, Handbook of Microbiological Media. CRC Press, Inc., Boca Raton, Fla.) [0.02 M $(NH_4)_2SO_4$, 0.01 M sodium citrate, 8 mM $Na_2PO_4$, 2 mM $MgSO_4.7H_2O$, 1 mM KCl, 30 nM $FeSO_4.7H_2O$] with 0.5% wt/vol glucose and either 0.5% wt/vol polygalacturonic acid or cellobiose. All chemicals were obtained from Sigma Chemical Co. (St. Louis, Mo.). Oligonucleotides were synthesized by Integrated DNA Technologies (Coralville, Iowa). Restriction enzymes and T4 DNA ligase were obtained from New England BioLabs (Ipswich, Mass.). DNA sequencing reactions were performed at the Sequencing and Synthesis Facility at the University of Georgia (Athens, Ga.).

TABLE 1

*E. coli* strains and plasmids used in this study.

| Strain, plasmid, or oligonucleotide | Relevant characteristics | Source or reference |
|---|---|---|
| *Escherichia coli* | | |
| KO11 | pdc*adhB$^+$; Cm$^r$ | A |
| LY40A | KO11 with casAB | This study |
| JP07 | LY40A with pelE; Cm$^r$ Ap$^r$ | This study |
| JP07C | JP07 with pCPP2006; Cm$^r$ Ap$^r$ Spe$^r$ | This study |
| Plasmids | | |
| pLOI1998 | casR' AB | B |
| pST76-K | Ts; Cm$^r$ | C |
| pLOI2708 | pST76-K derivative, lacY: casAB: lacA, Zm promoter | This study |
| pPEL748 | pelE | D |
| pLOI2090 | pelE; Ap$^r$ | This study |
| pCPP2006 | out genes; Spc$^r$ | E |
| pDMA160 | pEVS107 derivative, mini-Tn7; mob; Em$^r$ Kn$^r$ | E. V. Stabb |
| pEDH24 | pDMA160 derivative, consensus promoter | This study |
| pEDH25 | pEDH24 derivative, pe/E; Ap$^r$ | This study |
| pUXBF13 | R6K ori; tns genes; Ap$^r$ | F |
| pEVS104 | pRK2013 derivative; conjugal tra and trb genes | G |
| Oligonucleotides | | |
| LPY1 | 5'-G<u>AGATCT</u>TAAGGAAAAACAG CATGGA-3' (SEQ ID NO : 7) | This study |
| LPY2 | 5'-ATAGCCGGCGTCCAGAAT-3' (SEQ ID NO : 8) | This study |
| LacYF | 5'-TTGCTCTTCCATGTACTATTTAAAAAACACAAAC-3' (SEQ ID NO: 9) | Sigma Genosys |
| LacYR | 5'-TTGCTCTTCGTTAAGCGACTTCATTCACCTGAC-3' (SEQ ID NO: 10) | Sigma Genosys |
| LacAF | 5'-TTGCTCTTCCATGCCAATGACCGAAGAATAAGAG-3' (SEQ ID NO: 11) | Sigma Genosys |
| LacAR | 5'-TTGCTCTTCGTTAAACTGACGATTCAACTTTATA-3' (SEQ ID NO: 12) | Sigma Genosys |
| LacZ | 5'-GGTGAAGTGCCTCTGGATGT-3' (SEQ ID NO: 13) | This study |
| CasA | 5'-CGCCTACCCGAGTGAGAATA-3' (SEQ ID NO: 14) | This study |
| CasB | 5'-GCAAAGCGGAAGTCTACCAG-3' (SEQ ID NO: 15) | This study |
| CynX | 5'-ATGCCTTCGGTGATTAAACG-3' (SEQ ID NO: 16) | This study |
| Promoter | 5'-CTAGTTGACATGATAGAAGCACTCTACTATATT-3' (SEQ ID NO: 17) <br> 3'-AACTGTACTATCTTCGTGAGATGATATAACTAG-5' (SEQ ID NO: 18) | E. V. Stabb |
| EDH160 | 5'-TGCTCAACGGGAATCCTGCTCT-3' (SEQ ID NO:19) | This study |
| EDH2090F | 5'-GCGCAT<u>GGGCCC</u>ACACAGGAAACAGCTATGACC-3' (SEQ ID NO: 20) | This study |
| EDT2090R | 5'-GCATGC<u>GGGCCC</u>GTTACCAATGCTTAATCAGTGAGG-3' (SEQ ID NO: 21) | This study |

TABLE 1-continued

E. coli strains and plasmids used in this study.

| Strain, plasmid, or oligonucleotide | Relevant characteristics | Source or reference |
|---|---|---|
| EDHPelB | 5'-TCAGCACGAACACGAACCGTCTTA-3' (SEQ ID NO: 22) | This study |
| EDHPelE | 5'-TGTGCTGCAAGGCGATTAAGTTGG-3' (SEQ ID NO: 23) | This study |

A, Ohta et al., 1991, Appl. Environ. Microbiol., 57: 893-900; B, Lai et al., 1997, Appl. Environ. Microbiol. 63: 355-363; C, Posfai et al., 1997, J. Bacteriol., 179: 4426-4428; D, Keen et al., 1986, J. Bacteriol., 168: 595-606; E, He et al., 1991, Proc. Natl. Acad. Sci., 88: 1079-1083; F, Bao et al., 1991, Gene, 109: 167-168; G, Stabb et al,. 2002, Methods Enzymol., 358: 413-426.

Genetic procedures and recombinant techniques. Standard methods were employed to construct plasmids and transfer DNA (Sambrook, et al., 1989. Molecular cloning: a laboratory manual, 2 ed. Cold Spring Harbor Laboratory, Cold Spring Harbor, N.Y.). PCR was performed using either Platinum Taq (Invitrogen, Carlsbad, Calif.) or Phusion™ High-Fidelity DNA Polymerase Kit (New England BioLabs, Ipswich, Mass.), following the manufacturer's recommendations for reaction programs.

Figure 1:
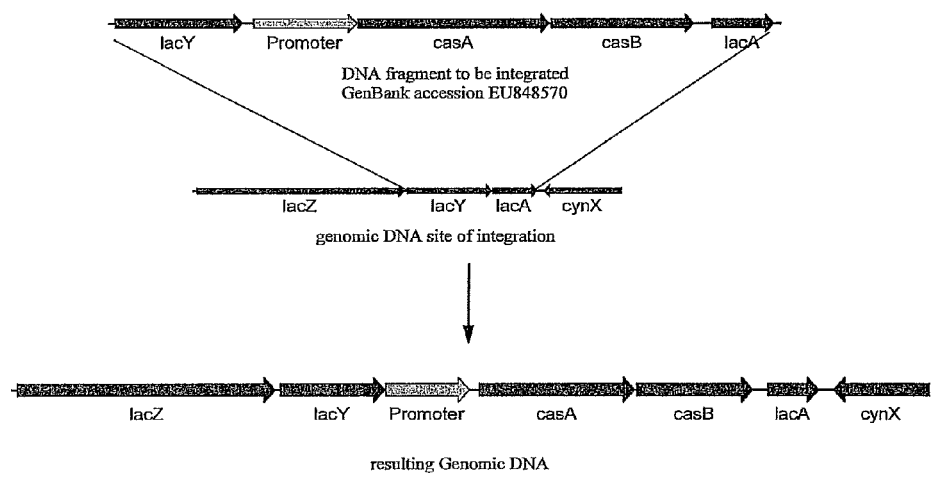
FIG. 1. Integration of casAcasB into the lac operon of *E. coli* KO11.

Chromosomal insertion of K. oxytoca casAB genes in E. coli KO11. The casAB genes from K. oxytoca (Lai, et al., 1997, Appl. Environ. Microbiol. 63:355-363) were chromosomally integrated into E. coli KO11 (Ohta, et al., 1991. Appl Environ Microbiol 57:893-900), between the lacY and lacA genes after adding a strong surrogate promoter, (Zhou, et al., 1999, J. Ind. Microbiol. Biotechnol. 22:600-607 (FIG. 1). The DNA fragment constructed for integration has been deposited in GenBank (Accesssion No. EU848570). Primers used in construction are listed in Table 1 (LPY1, LPY2, LacYF, LacYR, LacAF, and LacAR)

For chromosomal insertion, the casAB genes were amplified from pLOI1998 (Lai, et al., 1997, Appl. Environ. Microbiol. 63:355-363) and ultimately engineered into pLOI2707, a temperature conditional vector, with lacY and lacA flanking the casAB genes. Z. mobilis genomic DNA was randomly inserted upstream of casAB on pLOI2707 to create a library; these clones were screened for large colony size and dark red color on MacConkey agar plates with 2% wt/vol cellobiose to find a strong surrogate promoter for cellobiose utilization. One plasmid, designated pLOI2708, which contained an insert of approximately 1 kb with a promoter, was chosen for further study. After electroporating E. coli KO11 with pLOI2708 and selecting for casAB recombinants, cells were screened for red colony color on MacConkey agar containing 2% wt/vol cellobiose and LB agar containing 2% wt/vol glucose and 600 mg/L chloramphenicol to select for high expression of casAB and Z. mobilis pdc and adhB, respectively. The strain generated was named E. coli LY40A.

Chromosomal insertion of E. chrysanthemi pelE gene in E. coli LY40A. A double-stranded E. coli consensus promoter sequence was constructed by heating two complementary single-stranded DNA oligos with overhangs at 98° C. for 10 min (Table 1). The oligos were cooled to room temperature, cloned into the AvrII site of pDMA160 to make pEDH24, and transformed into E. coli BW23474 using a standard heat shock protocol (Sambrook, et al., 1989. Molecular cloning: a laboratory manual, 2 ed. Cold Spring Harbor Laboratory, Cold Spring Harbor, N.Y.). Directionality of the promoter was confirmed via DNA sequencing using the EDH160 primer. The BsrBI fragment carrying the pelE gene from pPEL748 (Keen, et al. 1986, J. Bacteriol. 168:595-606) was inserted into the SmaI-PstI site of pUC18 to generate pLOI2090. The pelE and bla genes were amplified from pLOI2090 via PCR using primers EDH2090F and EDH2090R with engineered ApaI sites and cloned into pEDH24 at the ApaI site. Subsequent clones were investigated for directionality of the pelE-bla fragment, and the plasmid with pelE-bla in the correct orientation to the consensus promoter was named pEDH25. A triparental mating of E. coli LY40A with E. coli BW23474 pUXBF13), E. coli BW23473 pEVS104 (Stabb, et al., 2002, Methods Enzymol. 358:413-426), and E. coli BW23474 pEDH25, was performed to insert the mini-Tn7 transposon with pelE and bla into the chromosome, yielding strain E. coli JP07 after selection on LB containing Cm and Ap. Strain verification was accomplished by sequence analyses using primers EDHPelB and EDHPelE. Cosmid pCPP2006 (He, et at, 1991, Proc. Natl. Acad. Sci. 88:1079-1083) was transformed into E. coli JP07 using standard heat shock protocol (Sambrook, et al., 1989. Molecular cloning: a laboratory manual, 2 ed. Cold Spring Harbor Laboratory, Cold Spring Harbor, N.Y.), giving strain E. coli JP07C.

Construction of E. coli JP08C. To construct pTOGL, the oligogalacturonide lyase gene, ogl, was PCR amplified from Erwinia chrysanthemi 3937 using primers OglF and OglR and cloned into pCR2.1 using the TOPO TA Cloning Kit (Invitrogen, Carlsbad, Calif.). OglF contained the consensus E. coli promoter sequence employed in previous experiments. pTOGL was then transformed into JP07C via heat shock (Sambrook, et al., 1989. Molecular Cloning: a Laboratory Manual, 2nd edition), giving strain E. coli JP08C.

Cellobiase assay. Assays for cellobiase activity were performed essentially as described previously (Moniruzzaman, et al., 1997, Appl. Environ. Microbiol. 63:4633-4637). Briefly, ethanologenic E. coli were grown in LB with 2% wt/vol cellobiose for 24 hours at 37° C. with shaking. Cells were harvested via centrifugation at 10,000 g for 10 minutes and lysed by sonication in 50 mM phosphate buffer, pH 7.2. Lysates were assayed for 15 minutes in 50 mM phosphate buffer with 2 mM p-nitrophenyl-β-D-1,4-glucopyranoside (PNPG). The reaction was terminated by the addition of 1 M $Na_2CO_3$ and ρ-nitrophenol content was measured at 410 nm. Units are defined as μmol product formed per minute per mL. Protein assays were performed on the supernatant by the Bradford method (Bradford, 1976, Anal. Biochem. 72:248-254), and enzyme activity reported as specific activity in U/mg protein. Data represents the mean of three separate experiments.

Pectate lyase assay. Assays for pectate lyase activity were performed as described previously (Collmer, et al., 1988, Methods in Enzymology, vol. 161. Academic Press, Inc., San Diego, Calif.). Briefly, ethanologenic E. coli were grown in MM with 0.5% wt/vol glucose and 0.5% wt/vol polygalacturonic acid for 48 hours at 37° C. with shaking. Culture supernatant was harvested via centrifugation at 10,000 g for 10 minutes. Supernatant was assayed by rapidly mixing with substrate [60 mM Tris-HCl, pH 7.2, 0.6 mM $CaCl_2$, 0.24% wt/vol polygalacturonic acid], both previously equilibrated to 37° C., and monitoring the formation of 4,5-unsaturated products at 232 nm for 5 min with a linear rate of reaction for at least 30 s. Units are defined as µmol product formed per min per mL. Protein assays were performed on the supernatant by the Bradford method (Bradford, M. 1976, Anal. Biochem. 72:248-254), and enzyme activity reported as specific activity in U/mg protein. Data represents at least four separate experiments.

Sugar beet fermentations and analysis of ethanol production and reduced sugars. Fermentations were performed essentially as described previously (Doran, et al., 2000, Appl. Biochem. Biotechnol. 84-86:141-152). Sugar beet pulp dry weight was calculated using a Denver Instrument IR 35 Moisture Analyzer (Denver, Colo.). In a blender, 10 g dry wt sugar beet pulp, 100 mL of 2× LB liquid media, and water to a final volume of 200 mL were blended at full speed for 10 s and then autoclaved in a 500 mL fleaker; blending was necessary to reduce particle size as very low fungal enzymes loads were used. The fleakers were placed in a water bath at 45° C. and mixed with magnetic stirrers. The pH was adjusted to 4.5 using a Jenco 3671 pH controller (San Diego, Calif.). Spezyme CP (Genencor; Copenhagen, Denmark) and pectinase from *Aspergillus niger* (Sigma P2736) (Novozymes; Franidinton, N.C.) were added to the fleaker at concentrations of 0.5 filter paper units (FPU) per g dry wt and 4 polygalacturonase units (PGU) per g dry wt, respectively. After 24 h, the pH was increased to 6.8 and the temperature was decreased to 35° C. and maintained throughout the fermentation. Appropriate antibiotics were added to each fleaker, and they were inoculated to an $OD_{550}$ 1.0 with cells collected via centrifugation (10 000×g; 10 min) from overnight cultures of *E. coli* strains KO11, LY40A, JP07C, or JP08C. Fermentations were run for 72 h with samples collected every 24 h.

To quantify ethanol production, gas chromatography (GC) was performed; fermentation supernatant samples were filtered with a 0.22 µm filter prior to analysis. Ethanol concentrations were normalized to zero to account for ethanol added from antibiotic stocks. Reducing sugar analysis was performed using the dinitrosalicylic acid assay method (Miller, et al., 1959, Anal. Chem. 31:426-428).

Examination of oligogalacturonides. To quantify oligogalacturonides with a degree of polymerization (dp) less than 6, fermentation supernatant was diluted 1:3 in water and ethanol was added to a final concentration of 11% (vol/vol). The solution was incubated with agitation for 16 h at 4° C. and then centrifuged at 7500 g for 15 min. This supernatant was diluted and analyzed at 235 nm (Spiro, et al., 1993. Carbohydr. Res 247:9-20). The absorbance of fermentation supernatant preparation of *E. coli* KO11 at 72 hours was used as the baseline. Data represents the average of two experiments.

Results and Discussion

Construction of *E. coli* LY40A. Previous research identified cellobiose phosphoenolpyruvate-dependent phosphotransferase genes (casAB) from *K. oxytoca* that allowed rapid growth of *E. coli* DH5α with cellobiose as the sole carbon source (Lai, et al., 1997. Appl. Environ. Microbiol. 63:355-363). However, when a plasmid containing casAB was transferred to *E. coli* KO11, expression was poor; mutational studies of this plasmid in KO11 suggested the native promoter was more tightly controlled in this strain (Moniruzzaman, et al., 1997, Appl. Environ. Microbiol. 63:4633-4637). To create a stable, cellobiose-fermenting strain of *E. coli* KO11, the casAB genes were inserted into the chromosome with a strong surrogate promoter. The strain generated was named *E. coli* LY40A. Enzyme assays with ρ-nitrophenyl-β-D-1,4-glucopyranoside verified the absence and presence of cellobiase activity in KO11 and LY40A, respectively (Table 2). Integration by double homologous recombination was verified using primers (LacZ, CasA, CasB, and CynX) that included the lacZ and cynX genes flanking the genomic insertion site (Table 1).

TABLE 2

Cellobiase and extracellular pectate lyase specific activity for *E. coli* KO11 and derivative strains (standard deviation; n = 3)

| E. coli Strain | Specific Activity (IU/mg protein) | |
|---|---|---|
| | Cellobiase | Pectate Lyase |
| KO11 | 0 | 0 |
| LY40A | 15.0 ± 0.4 | 0 |
| JP07 | 15.8 ± 1.0 | 0.2 ± 0.3 |
| JP07C | 15.3 ± 1.1 | 18.9 ± 1.2 |
| JP08C | 5.4 ± 0.3 | 49.3 ± 0.9 |

While chromosomal insertion of casAB improves *E. coli* KO11 by enabling breakdown of cellobiose without supplemental cellobiase, the complexity of lignocellulosic substrates necessitates many other types of enzymes for breakdown. Further engineering of *E. coli* LY40A with additional types of enzymes should therefore enable decreased use of exogenous enzymes.

Construction of *E. coli* JP07 and JP07C. In lignocellulosic substrates, pectin interacts with lignin, hemicellulose, and cellulose, and degradation of pectin is necessary to allow the disintegration of other components. Therefore, a pectate lyase, which cleaves the polygalacturonate repeating chains of pectin, was engineered into *E. coli* LY40A with a surrogate promoter.

For chromosomal integration, a mini Tn7 system was used, which inserts as a single copy in the neutral att site in the *E. coli* chromosome (Bao, et al., 1991. Gene 109:167-168). pelE and bla were PCR amplified from pLOI2090 and cloned into pDMA160 with an *E. coli* consensus promoter, resulting in plasmid pEDH25. The plasmid was sequenced to verify promoter directionality and pelE sequence; a 61 bp deletion occurred between the promoter and pelE, but did not affect expression (data not shown). pEDH25 was conjugated into *E. coli* LY40A, and pelE transposed into the att site resulting in strain *E. coli* JP07.

Previous studies with *E. chrysanthemi* pectate lyases showed that a Sec-independent pathway, encoded by the out genes, was necessary for secretion of these enzymes (He, et al., 1991, Proc. Natl. Acad. Sci. 88:1079-1083). A cosmid with a 40 kb fragment of the *E. chrysanthemi* genome containing the out genes, pCPP2006, was electroporated into strain *E. coli* JP07 to give strain *E. coli* JP07C (He, et al., 1991, Proc. Natl. Acad. Sci. 88:1079-1083). Enzyme assays with ρ-nitrophenyl-β-D-1,4-glucopyranoside were performed to ensure that cellobiase activity in *E. coli* JP07 and JP07C was not affected by the addition of pelf (Table 2). Subsequently, assays were performed with polygalacturonic acid to demonstrate extracellular pectate lyase activity (Table 2). *E. coli* KO11 and LY40A demonstrated no activity, while JP07 varied greatly, reaching, at the most, 0.5 U/mg protein; the occasional presence of activity could be attributed to cell lysis. *E. coli* JP07C, however, exhibited 18.9 U/mg protein of extracellular pectate lyase activity, demonstrating the functionality of the out genes secretion system.

Figure 2:
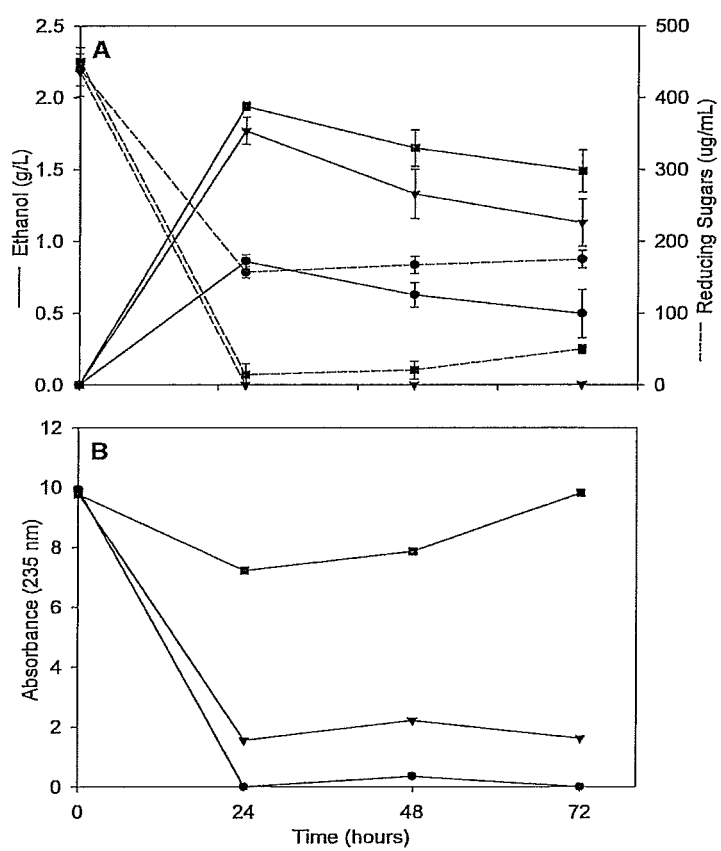
FIG. 2. (A) Ethanol production and reducing sugars from sugar beet pulp fermentation for *E. coli* KO11, LY40A, and JP07C (standard error, n=3; solid lines indicate ethanol concentration and dashed lines represent reducing sugar concentrations). (B) Absorbance at 235 nm of oligogalacturonides with dp ≤6 from the above sugar beet pulp fermentation (data represents average of two experiments); ● KO11; ▼ LY40A; ■ JP07C.

Comparison of *E. coli* KO11, LY40A, and JP07C. To demonstrate use of these engineered *E. coli* strains, sugar beet pulp fermentations were performed with very low fungal enzyme loads during pretreatment (FIG. 2A). A typical fermentation of sugar beet pulp with *E. coli* KO11 would be performed with 10.5 FPU/g dry wt cellulase, 120.4 PGU/g dry wt pectinase, and 6.4 CBU/g dry wt cellobiase (Doran, et al., 2000, Int. Sugar. J. 102:336-340). To determine the effect of the engineered enzymes, 0.5 FPU/g dry wt cellulase and 4 PGU/g dry wt polygalacturonase were used; with such low loads of exogenous enzymes, only a small portion of the lignocellulose structure is degraded, which sequesters much of the sugar available for conversion to ethanol and leads to low ethanol yields. Both *E. coli* LY40A and JP07C had significantly higher ethanol yields than *E. coli* KO11. Examination of reducing sugars demonstrates *E. coli* KO11's low yield: the high amount (140-185 µg/mL) of reducing sugars present throughout the fermentation corresponds to oligomeric substrates the strain is unable to metabolize. Comparison with casAB-containing *E. coli* LY40A and JP07C, whose reducing sugar concentrations decrease to near zero within 24 hours, suggests a major component of the reducing sugars which *E. coli* KO11 is unable to consume is cellobiose, illustrating the significance of the addition of casAB to the strain.

Ethanol yields for *E. coli* JP07C were not significantly higher than those for LY40A. However, the concentration of reducing sugars for *E. coli* JP07C continually increased after 24 h while that of LY40A did not (FIG. 2A). If PelE produced by *E. coli* JP07C is cleaving large polygalacturonate chains without releasing large amounts of monomeric sugars, the reducing sugar concentration would increase while ethanol production would not. To test this hypothesis, oligogalacturonides with a degree of polymerization (dp) greater than six were precipitated from the fermentation samples and the remaining oligogalacturonides with a dp of six or less were measured by absorbance at 235 nm. As seen in FIG. 2B, the absorbance of *E. coli* JP07C is significantly higher than that of KO11 or LY40A throughout the fermentation, and, after fermentation of sugars released from the fungal enzymes, continues to increase from 24 to 72 h; this difference in absorbance corresponds to an increase of short chain oligogalacturonides throughout fermentation, demonstrating the enzymatic breakdown of polygalacturonate.

Figure 3:
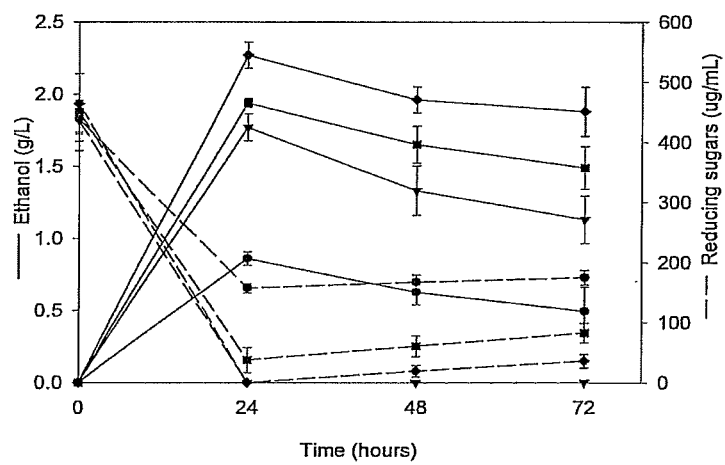
FIG. 3. Ethanol production and reducing sugars from sugar beet pulp fermentation for *E. coli* KO11, LY40A, JP07C, and JP08C (standard error, n=3; solid lines indicate ethanol concentration and dashed lines represent reducing sugar concentrations); ● KO11; ▼ LY40A; ■ JP07C; ◆ JP08C.

Comparison of JP07C and JP08C. The oligogalacturonide lyase of *Erwinia chrysanthemi* 3937 (Collmer, et al., 1981, Proc. Natl. Acad. Sci. 78:3920-3924) was transformed into *E. coli* JP07C to give strain JP08C, where ogl is maintained on plasmid pTOGL. Enzyme assays with JP08C demonstrated a large increase in the production of 4,5-unsaturated products, indicating ogligogalacturonide activity in addition to pectate lyase activity (Table 2). Sugar beet pulp fermentations were performed to determine if this Ogl activity leads to higher ethanol yields than that of predecessor strains. The combination of pelE and ogl significantly increased ethanol production when compared to LY40A (FIG. 3). Examination of reducing sugar concentrations for JP08C shows that while they are decreased in comparison to JP07C, they do continue to increase slightly throughout the fermentation; this suggests that polygalacturonic acid chains are being released from the sugar beet pulp, but are not being cleaved into di- and tri-galacturonides subject to oligogalacturonide lyase activity. As sugar beet pulp is highly methyl esterified (60%), the activities of both PelE and Ogl might be partially inhibited, and further addition of a pectin methylesterase could increase the activity of these two enzymes (Sun, et al., 1998, Polymer J. 30:671-677).

Engineering these ethanologenic *E. coli* strains to produce lignocellulose degrading enzymes during fermentation can allow partial saccharification and co-fermentation, which enables decreased use of exogenous fungal enzymes in biomass saccharification steps, reducing the cost of the entire process. The addition of casAB for cellobiose utilization significantly impacts ethanol production from lignocellulosic biomass and drastically reduces the need for fungal cellobiases, possibly eliminating the need for this type of enzyme altogether. While the addition of pelE did not display the same effect, secretion of pectate lyase did considerably increase degradation of polygalacturonate, and further engineering of *E. coli* JP07C to produce an oligogalaturonate lyase, ogl, allowed breakdown of polygalacturonate to monomeric sugars during fermentation and increased ethanol yield. Engineering of *E. coli* JP08C demonstrates the possibility of creating a strain of *E. coli* for consolidated bioprocessing, thereby eliminating the need for exogenous enzymes altogether (Lynd, et al., 2008, Nature Biotechnol. 26:169-172). Further work to integrate cellulases, hemicellulases, and other pectinases will advance this goal of a single microorganism capable of both degradation and fermentation of lignocellulosic biomass.

Example 2

*Paenibacillus amylolyticus* C27 was isolated from the hindgut of *Tipula abdominalis* and found to produce lignocellulose-degrading enzymes. A library was constructed with C27 genomic DNA for heterologous expression of biological characteristics in *Escherichia coli*. Two pectate lyase genes, pelA and pelB, were identified while screening a genomic library in *E. coli* for pectinase activity. PelA encodes a 222 amino acid protein and demonstrated highest activity on polygalacturonic acid, but retained 60% and 56% of maximum activity on 8.5% and 90% methylated pectin, respectively. $CaCl_2$ was required for activity, and optima were pH 10.5, 45° C., and 1.5 mM $CaCl_2$. PelA has high identity (95%) to PelA from *P. barcinonensis*, and is a subclass of the pectate lyase family III from saprophytic, non-pathogenic bacteria. On the other hand, pelB encodes a 392 amino acid protein. Although PelB showed the highest activity on 20-34% methylated pectin, it retained 67%, 51%, 25%, and 1% of its maximum activity on polygalacturonic acid, 8.5%, 55-70%, and 90% methylated pectin, respectively. The optima were pH 9.5, 55° C., and 0.5 mM $CaCl_2$, and $CaCl_2$ was required for the enzymatic activity. PelB shows no significant similarity to any known enzyme, but contains many conserved sites of the pectate lyase family I subclass. It shows highest amino acid identity of only 28% to *Bacillus* sp. YA-14 PelK, *B. licheniformis* ATCC 14580 Pel, and *B. subtilis* reference strain 168 Pel.

Materials and Methods

Bacterial strains and plasmids. *P. amylolyticus* C27 was isolated from the hindgut of *Tipula abdominalis* (Cook, et al., 2007, Appl. Environ. Microbiol., 73, 5683-5686) and grown as described previously (Henriksen et al., 2007, Lett. Appl. Microbiol., 45, 491-496) in either tryptic soy broth or Davis minimal media. Strains and plasmids used for cloning are listed in Table 1. *Escherichia coli* strains were grown at 37° C. in Luria Bertani (LB) broth with 50 mg $L^{-1}$ ampicillin (Ap), where indicated.

TABLE 1

Cloning strains and plasmids used in this study

| Strain, plasmid, or oligonucleotide | Relevant characteristics | Source or reference |
|---|---|---|
| *Escherichia coli* | | |
| DH5α | F⁻endA1glnV44thi-1recA1relA1gyrA96 deoR nupG Φ80dlacZΔM15 Δ(lacZYA-argF)U169, hsdR17(rK⁻ mK⁺), λ⁻ | A |
| Plasmids | | |
| pUC19 | lacZα⁺; Apʳ | Invitrogen (Carlsbad, CA) |
| pEDH13C2 | pUC19 derivative; *P. amylolyticus* DNA fragment with pelA | This study |
| pEDH27 | pUC19 derivative; pelA⁺ | This study |
| pUC19-19F6 | pUC19 derivative; *P. amylolyticus* DNA fragment with pelB | This study |
| pWEB1 | pUC19 derivative; pelB⁺ | This study |
| Oligonucleotides | | |
| Seq2 | 5'-ACACTGAACGAAATGCTCCAAACC-3' (SEQ ID NO: 24) | This study for Pel A |
| PLAscF | 5'-GTACAGGGCCCGGATCCTTGACATGATAGAAGCACTCTACT ATATTCTAGTGCTTCTACGGTTCTGTGGGACAA-3' (SEQ ID NO: 25) | This study |
| PLAscR | 5'-CGATCAAGCTTGGGCCCGAGCGGCCGCCTCGAGTCCACATG GTTTGGAGCATTTCG-3' (SEQ ID NO: 26) | This study |
| SCpelBF | 5'-GCAGTGAGCTCTTGACATGATAGAAGCACTCTACTATATTC TAGTTATACTTATCGGGAGGAATCG-3' (SEQ ID NO: 27) | This study |
| SCpelBR | 5'-CATGGGATCCCGGAGCGCTTAACTTAGTAACTC-3' (SEQ ID NO: 28) | This study |
| Seq2 | 5'-ACCGCAGCATCGCTTATGTAGGTA-3' (SEQ ID NO: 29) | This study |
| Seq3 | 5'-AGTATCACTGTTGCCACGGAAGGA-3' (SEQ ID NO: 30) | This study |
| Seq4 | 5'-TGGTGAGTCCATTAAAGCCGTCCA-3' (SEQ ID NO: 31) | This study |

A, Meselson and Yuan, 1968, *Nature*, 217: 1110-1114.

Library construction and enzymatic screening. Genomic DNA from *P. amylolyticus* C27 was prepared using the DNeasy Blood and Tissue Kit (Qiagen, Valencia, Calif.). After partial digestion with Sau3AI and agarose gel extraction of 2-5 kb fragments, *P. amylolyticus* C27 genomic fragments were ligated into BamHI digested pUC19, transformed into *E. coli* DH5α by heat shock (Sambrook, et al., 1989, *Molecular cloning: a laboratory manual*, Cold Spring Harbor, N.Y., Cold Spring Harbor Laboratory), and grown on LB agar with 50 mg/L ampicillin, 1 mg/L X-Gal, and 2.5 mg/L IPTG. Insert-containing transformants were screened for pectinase activity on polygalacturonase medium (Starr, et al., 1977, *J. Clin. Microbiol.*, 6, 379-386). After growth, plates were flooded with 2N HCl and pectinase-producing colonies were identified by the appearance of clearing surrounding colonies.

Pectinase identification and subcloning. At the Sequencing and Synthesis Facility at the University of Georgia, plasmid pEDH13C2 from a pectinase-producing clone (13C2) was first sequenced with primer M13F followed by primer Seq2 Primers. PLAscF and PLAscR were used to subclone the pectinase gene, pelA, from pEDH13C2 into pUC19 using BamHI and HindIII sites, which were engineered into the forward and reverse primer, respectively, giving plasmid pEDH27. The forward primer also contained a consensus *E. coli* promoter (E. V. Stabb). Plasmid pUC19-19F6 from another pectinase-producing clone (19F6) was sequenced with primer 19F6 M13R followed by Seq 2, Seq3, Seq4. SCpelBF and SCpelBR were used to subclone the pectinase gene, pelB, from pUC19-19F6 into pUC19 using SacI and BamHI restriction enzyme sites that were engineered into the forward and reverse primers, respectively, creating plasmid pWEB1. The forward primer contained the same consensus *E. coli* promoter (E. V. Stabb) as the forward primer used to create pEDH27.

Enzyme assays. PelA pectate lyase assays were performed essentially as described (Collmer, et al., 1988, *Methods in Enzymology*. San Diego, Calif., Academic Press, Inc.) (Soriano, et al., 2000, *Microbiology*, 146, 89-95) with *E. coli* DH5α pEDH27 cell extracts prepared by sonication. The standard enzyme assay mixture for PelA contained 0.2% (w/v) polygalacturonic acid (PGA, Sigma) or pectin (8.5% esterified citrus pectin MP Biomedicals (Irvine, Calif.) or 90% esterified citrus pectin purchased from Sigma (St. Louis, Mo.)) in a final volume of 1 mL 50 mM glycine buffer pH 10.5 with 1.5 mM $CaCl_2$; the assay mixture and enzyme preparation were equilibrated to 45° C. and monitored for the formation of Δ-4,5-unsaturated products at 235 nm for 1 to 3 min.

Pectate lyase assays for PelB were performed similar to PelA but with *E. coli* DH5α pWEB1 supernatant. The standard enzyme assay mixture for PelB contained 0.2% (w/v) polygalacturonic acid (PGA, Sigma) or pectin (8.5% esterified citrus pectin MP Biomedicals (Irvine, Calif.), 20-34%, 55-70%, and 90% esterified citrus pectin Sigma (St. Louis, Mo.)) in a final volume of 1 mL 50 mM glycine buffer pH 9.5 with 0.5 mM $CaCl_2$; the assay mixture and enzyme preparation were equilibrated to 55° C. and monitored for the formation of Δ-4,5-unsaturated products at 235 nm for 1 min. One unit of enzyme activity was defined as the amount of enzyme that produces 1 μmol 4,5-unsaturated product per minute under both assay conditions described. Specific activity is reported as U/mg protein and the Bradford method was used to determine protein concentration of enzyme preparations.

The pH optimum was determined at 40° C. with 1 mM $CaCl_2$ using the following buffers over the stated pH ranges: 50 mM sodium citrate, pH 3.0-4.0; 50 mM sodium acetate, pH 4.0-6.0; 50 mM sodium phosphate, pH 6.0-8.0; 50 mM Tris-HCl, pH 8.0-9.0; and 50 mM glycine, pH 9.0-12.0. For PelA the temperature optimum was determined at pH 10.5 in a range of 25-55° C., and the CaCl₂ concentration optimum was determined at pH 10.5 and 45° C. in a range of 0-2.5 mM. For PelB the temperature optimum was determined at pH 9.5 in a range of 15-60° C., and the CaCl₂ concentration optimum was determined at pH 9.5 and 55° C. in a range of 0-2.5 mM.

Results and Discussion

Cloning and identification of the pectate lyase. A library containing 2- to 5-kb chromosomal fragments of *P. amylolyticus* C27 was constructed in *E. coli* DH5α. Two pectinase-positive clones, 13C2 and 19F6, were identified after screening approximately more than 6,000 clones. Sequencing of the plasmid carried in the 13C2 clone, pEDH13C2, showed an insert of 2 kb. A single ORF of 669 bp was identified and named pelA. A putative ribosomal-binding (AAGGGAGGA) site is located eight nucleotides upstream of the ATG start codon; also upstream of pelA is a putative promoter with −10 (TTGTAA) and −35 (TTCTGT) elements. The deduced protein sequence of the ORF is 222 amino acids. The protein has an N-terminal region with features of a *Bacillus* signal peptide, and the most likely cleavage site is between amino acids 26 and 27 (Nielsen, et al., 1997, *Protein Eng.,* 10:1-6).

Sequencing of the plasmid carried in the 19F6 clone, pUC10-19F6, showed an insert of 1.5-kb. A single ORF of 1176 bp was identified and named pelB and encodes a 302 amino acid protein. Located eight nucleotides upstream of the ATG start codon is a putative ribosomal-binding (GGGAGGAA) similar to a Shine-Dalgerno site. Also, located upstream of pelB is a putative promoter with −10 (TATACT) and −35 (TTGTGA) elements.

PelA and PelB were compared to known proteins by performing a protein-protein BLAST (blastp) using the NCBI database (Altschul, et al., 1997, *Nucleic Acids Res.,* 25, 3389-3402). Homology was found for PelA to pectate lyases within family III (PL3), but not any other class. PelA was 95% identical to PelA from *P. barcinonensis* (Soriano, et al., 2000, *Microbiology,* 146, 89-95), but also showed high identity to other *Bacillus* sp. pectate lyases: 78% to *Bacillus* sp. KSM-P15 pectate lyase (Hatada, et al., 2000, *Eur. J. Biohcem.,* 267, 2268-2275), 55% to *B. subtilis* PelC (Soriano et al., 2006, *Microbiology,* 152, 617-625), 54% to *B. licheniformis* YvpA, and 53% to *Bacillus* sp. P-2850 pectate lyase. PelA has lower identity to phytopathogens *Fusarium solani* PelB (31%) (Guo, et al., 1995, *J. Bacteriol.,* 177, 7070-7077), *Erwinia chrysanthemi* PelI (15%) (Shevchik, et al., 1997, *J. Bacteriol.,* 179, 7321-7330), and *E. carotovora* Pel3 (12%) (Liu, et al., 1994, *Appl. Environ. Microbiol.,* 60, 2545-2552). All of these enzymes have an arginine residue (Arg-157 in C27 PelA), which is believed to extract a proton during the β-elimination mechanism of the reaction (Akita, et al., 2001, *Acta Cryst.,* D57, 1786-1792). Three of four signature blocks of conserved residues for PL3 enzymes (Shevchik, et al., 1997, *J. Bacteriol.,* 179, 7321-7330) are found in PelA, but, like *P. barcinonensis* PelA, *Bacillus* sp. KSM-P15 PL, *B. subtilis* PelC, *B. licheniformis* YvpA, and *Bacillus* sp. P-2850 PL enzymes, the fourth block of residues is not conserved; it is replaced by another domain, not found in other pectate lyases (FIG. 4) (Soriano, et al., 2006, *Microbiology,* 152, 617-625). Additionally, these enzymes have high homology to each other and lower cysteine content than other family PL3 pectate lyases. PelA appears to belong to a subgroup of family PL3 enzymes from saprophytic bacteria (Soriano, et al., 2006, *Microbiology,* 152, 617-625) which includes *P. barcinonensis* PelA, *Bacillus* sp. KSM-P15 PL, *B. subtilis* PelC, *B. licheniformis* YvpA, and *Bacillus* sp. P-2850 PL.

PelB showed homology to family I pectate lyases (PL1), but not to any other class. PelB showed highest identity of only 28% to *Bacillus* sp. YA-14 PelK (Kim, et al., 1994, *Biotech. Biochem.* 58, 947-949), *B. licheniformis* ATCC 14580 Pel (Rey, et al., 2004, *Genome Biology,* 5, R77), and *B. subtilis* reference strain 168 Pel (Kunst, F. et al. 1997, *Nature,* 390:249-256). In addition, PelB showed lower identity to other pectate lyases: 27% to *Thermotoga maritime* PelA (Kluskens, et al., 2003, *Biochem. J.,* 370, 651-659), and 26% to *B. subtilis* BS-2 Pel, and *B. amyloliquefaciens* TB-2 Pel. All of the enzymes listed above contain the core structure of the parallel β-helix (vWIDH region), conserved catalytlic sites, conserved calcium binding sites, and sites conserved in all thermostable PL1 pectate lyases (FIG. 5). On the other hand, PelB only contains six of the seven conserved sites in all thermostable PL 1 pectate lyases and does not contain any of the three conserved catalytic sites. PelB does contain the core structure of the parallel β-helix, vWIDH, but does not contain the other two pectate lyase conserved sequence patterns, AxDIKGxxxxVTxS and VxxRxPxxRxGxxHxxxxN (Xiao, et al., 2007, *Appl. Environ. Microbiol.:* 10: 1-28). (Henrissat, et al., 1995, *Plant Physiol.,* 107, 963-976). All of these enzymes, including PelB (Arg-157 in C27 Pel B), also have the arginine residue, like PelA, that is thought to extract a proton during the β-elimination mechanism of the reaction (Akita et al., 2001, Acta Cryst., D57, 1786-1792). It appears as though PelB is mostly likely a subclass of family I pectate lyase (PL1).

Characterization of *P. amylolyticus* C27 PelA and PelB. SDS-PAGE analysis of *E. coli* DH5α carrying plasmid pEDH27 cell extract showed a band of approximately 23 kDa (the predicted size of PelA) not present in the extract of *E. coli* DH5α pUC 19 (data not shown). These extracts exhibited pectate lyase activity on polygalacturonic acid (PGA), but did not show polygalacturonase, xylanase, or cellulase activity using dinitrosalycylic acid assays. PelA was active within a pH range of 7.5 to 11.5, with optimal activity at pH 10.5 (FIG. 6A). The temperature optimum was 45° C., but PelA retained at least 50% of its activity within a range of 25 to 50° C. (FIG. 6B). CaCl₂ was necessary for activity, as it is for all known pectate lyases (Jurnak et al., 1996, IN VISSER, J. & VORAGEN, A. G. J. (Eds.) *Pectin and Pectinases.* Amsterdam, Elsevier), with maximum activity at 1.5 mM (FIG. 6C). The activity of PelA on citrus pectin was also investigated. Assays with 20-34% and 90% methylesterified citrus pectin demonstrated activity at 60% and 56% of the maximum activity on PGA, respectively (FIG. 7).

The high activity of PelA on both PGA and pectins with low and high levels of methylation is unusual, but was also observed for PelA from *P. barcinonensis* and PelC from *B. subtilis* (Soriano, et al., 2000, *Microbiology,* 146, 89-95) (Soriano, et al., 2006, *Microbiology,* 152, 617-625. Other family PL3 enzymes, like PelB and PelC from *E. chrysanthemi,* are active on PGA, but have highest activity on pectin with low levels of methylation with no activity on highly methylated pectin (Tardy, et al., 1997, *J. Bacteriol.,* 179, 2503-2511). Conversely, PelI from *E. chrysanthemi* and PelB from *E. carotovora* have highest activity on 45% and 68% methylated pectin, respectively, and low or no activity on PGA (Shevchik, et al., 1998, *Mol. Microbiol.,* 29, 1459-1469) (Heikinheimo, et al., 1995, *Mol Plant Microbe nteract.,* 8, 207-217). Thus, the *P. amylolyticus* C27 PelA, *P. barcinonensis* PelA, and *B. subtilis* PelC substrate utilization range, with activity on PGA as well as pectin with any degree of methylation, are unique among the pectate lyases described to date (FIG. 7).

While highly similar, *P. amylolyticus* C27 PelA, *P. barcinonensis* PelA (Soriano, et al., 2000, *Microbiology,* 146, 89-95), and *B. subtilis* PelC (Soriano, et al., 2006, *Microbiology,* 152, 617-625) do have distinct differences in activity optima and substrate preference. While the optima for C27 PelA is pH 10.5, both the *P. barcinonensis* PelA and PelC from *B. subtilis* have highest activity at pH 10 when assayed using the same method. The temperature optima differ for all three enzymes: for C27 PelA, it is 45° C., *P. barcinonensis* PelA, 50° C., and *B. subtilis* PelC, 65° C. Likewise, activity on pectic substances differs; the *B. subtilis* PelC shows highest activity on 22% methylated pectin, *P. barcinonensis* PelA on PGA or 22% methylated pectin, and C27 PelA on PGA.

PelB from *P. amylolyticus* was active within a pH range of 7.5 to 10.5, but the optimal activity was at pH 9.5 (FIG. 8A). PelB showed greatest activity from 40-55° C. The optimum temperature was 55° C., but significantly less activity was observed at 60° C. (FIG. 8B). PelB is similar to all other pectate lyases, in that, it requires $CaCl_2$ in order to be active (Jurnak, et al., 1996, IN VISSER, J. & VORAGEN, A. G. J. (Eds.) *Pectin and Pectinases*. Amsterdam, Elsevier). The optimum $CaCl_2$ concentration was 0.5 mM, but PelB still retained more than 75% of its activity within a range of 1.0-2.0 mM, including 96% of its activity at 1.5 mM (FIG. 8C).

Since PelB did not show high amino acid identity to any other known enzymes, its ability to be active on PGA and methylated pectin was studied by running assays with a range of pectic substrates: PGA, 8.5%, 20-34%, 55-70%, and 90% methylesterified citrus pectin. PelB showed highest activity on 20-34% methylated pectin, but retained 67%, 51%, 25%, and 1% of its maximum activity on polygalacturonic acid, 8.5%, 55-70%, and 90% methylated pectin, respectively, providing evidence that PelB is active on PGA as well as highly methylated pectin (FIG. 9).

*Thermotoga maritime* PelA showed highest activity on PGA, with only 41% and 2% activity on 30% and 74% methylated pectin, which differs from the activity observed by *P. amylolyticus* C27 PelB. In addition, *T. maritime* PelA optima were pH 9.0, 90° C., and calcium was required for activity, making it the most themoactive pectate lyase known to date (Kluskens, et al., 2003, *Biochem. J.*, 370, 651-659).

Although the percentage of maximum activity for C27 PelB on 90% methlyated pectin is lower than that observed for C27 PelA, the specific activities for PelA and PelB on the 90% methlyated pectin were similar. In addition, the specific activity for PelB on 8.5% methlyated pectin is almost twice the specific activity observed for PelA. PelB shows more enzymatic activity per protein concentration than PelA.

*P. amylolyticus* C27 PelA and PelB are not only the first pectate lyases described in *P. amylolyticus*, but also show an unusual combination of pectate lyase and pectin lyase activity by degrading both highly methylated pectin and polygalacturonic acid, respectively. Since both enzymes require $Ca^{2+}$ for activity, they are considered pecate lyases instead of pectin lyases. Pectin lyases do not require $Ca^{2+}$ for activity. This unusually activity has only been seen in two other enzymes which are in the pectate lyase family III group: *P. barcinonensis* PelA and *B. subtilis* PelC.

In addition, *P. amylolyticus* C27 PelA is part of a subgroup of five homologous enzymes that are the only pectate lyases in family III produced from nonpathogenic microorgaisms: *P. barcinonensis* pectate lyase A, *B. subtilis* pectate lyase C, *Bacillus* sp. P-2850 pectate lyase, *Bacillus* sp. KSM-P15 pectate lyase, and *P. amylolyticus* pectate A. So within this subgroup are three enzymes that show the unusual combination of pectate lyase and pectin lyase activity.

On the other hand, *P. amylolyticus* C27 PelB shows highest amino acid identity of only 28% to *Bacillus* sp. YA-14 PelK, *B. licheniformis* ATCC 14580 Pel, and *B. subtilis* reference strain 168 Pel. *P. amylolyticus* C27 PelB shows unique activity on a broad range of pectic structures. PelB only shows homology to polysaccharide lyase family I, but it is missing some of the conserved regions for PL family I, and one of the three Pel conserved regions (Xiao, et al., 2007, Appl. Environ. Microbiol.: 10: 1-28), (Henrissat, et al., 1995, *Plant Physiol.*, 107, 963-976). If PelB is not part of polysaccharide lyase family I, then it could be part of a novel family of polysaccharide lyases.

Example 3

Degradation of sugar beet pulp and examination of oligogalacturonides. Precultures of *E. coli* carrying plasmid pEDH27 were grown in LB with 50 mg $L^{-1}$ ampicillin overnight with shaking at 37° C. and inoculated into LB with 5% dry wt $L^{-1}$ sugar beet pulp to $OD_{550}$ 0.5. Sugar beet pulp cultures were grown at 37° C. with shaking and samples were removed every 24 h.

To quantify oligogalacturonides with a degree of polymerization (dp) less than 6, fermentation supernatant was diluted 1:3 in water and ethanol was added to a final concentration of 11% (vol/vol). The solution was incubated with agitation for 16 h at 4° C. and then centrifuged at 7500 g for 15 min. This supernatant was diluted and analyzed at 235 nm (Spiro et al., 1993, *Carbohydr. Res.*, 247:9-20) and compared to the absorbance of fermentation supernatant preparation immediately after inoculation.

Construction of *E. coli* JP27. Plasmid pEDH27 was transformed by heat shock into *E. coli* LY40A to construct strain JP27.

Sugar beet fermentations and analysis of ethanol production and reduced sugars. Fermentations were performed essentially as described previously (Doran et al., 2000, *Appl. Biochem. Biotechnol.*, 84-86:141-152). Sugar beet pulp dry weight was calculated using a Denver Instrument IR 35 Moisture Analyzer (Denver, Colo.). In a blender, 10 g dry wt sugar beet pulp, 100 mL of 2× LB liquid media, and water to a final volume of 200 mL were blended at full speed for 10 s and then autoclaved in a 500 mL fleaker; blending was necessary to reduce particle size as very low fungal enzymes loads were used. The fleakers were placed in a water bath at 45° C. and mixed with magnetic stirrers. The pH was adjusted to 4.5 using a Jenco 3671 pH controller (San Diego, Calif.). Spezyme CP (Genencor; Copenhagen, Denmark) and pectinase from *Aspergillus niger* (Novozymes; Franklinton, N.C.) were added to the fleaker at concentrations of 0.5 FPU/g dry wt and 4 PGU/g dry wt, respectively. After 24 h, the pH was increased to 6.8 and the temperature was decreased to 35° C. and maintained throughout the fermentation. Appropriate antibiotics were added to each fleaker, and they were inoculated to an $OD_{550}$ 1.0 with *E. coli* strains LY40A or JP27. Fermentations were run with samples collected every 24 h until completion.

To quantify ethanol production, gas chromatography (GC) was performed; fermentation supernatant samples were filtered with a 0.22 μm filter prior to analysis. Ethanol concentrations were normalized to zero to account for ethanol added from antibiotic stocks. Reducing sugar analysis was performed using the dinitrosalicylic acid assay method (Miller, 1959, *Anal. Chem.*, 31:426-428).

Degradation of sugar beet pulp. To examine potential applications of the C27 PelA for saccharification in lignocellulose fermentations to fuel ethanol, its ability to degrade pectin in sugar beet pulp was examined. *E. coli* DH5α carrying plasmid pEDH27 was grown in LB with 5% dry wt $L^{-1}$ sugar beet pulp and samples were taken to measure short chain oligogalacturonides that would be produced from pectate lyase activity. As shown in FIG. 10, the amount oligogalacturonides with a degree of polymerization <7 dramatically increased over 72 h for the strain expressing PelA, while *E. coli* DH5α pUC19 did not increase. As sugar beet pulp pectin is typically 60% methylated (Sun and Hughes, 1998, *Polymer J.*, 30:671-677), the ability of PelA to act on methylated pectin is desirable; the majority of described pectate lyases cannot significantly degrade pectin without added pectin methylesterase activity.

Sugar beet pulp fermentations with *E. coli* JP27. To better assess the applicability of PelA in fuel ethanol production processes, pEDH27 carrying pelA was added to ethanologen *E. coli* LY40A, a K011 derivative. *E. coli* LY40A and JP27 were grown in sugar beet pulp using very low fungal enzymes during saccharification; low ethanol yields were observed as expected. *E. coli* LY40A achieved a maximum ethanol yield of 1.79 g L$^{-1}$ ethanol by 24 h (FIG. 11). *E. coli* JP27, however, reached a maximum of 3.17 g L$^{-1}$ ethanol by 120 h, after displaying a lag between 24 h and 48 h. Examination of reducing sugars shows that sugars liberated by fungal enzyme saccharification are consumed within 24 h for both strains. *E. coli* LY40A reaches its maximum ethanol production at 24 h because it is incapable of further lignocellulose degradation. *E. coli* JP27 also consumes the sugars released by fungal enzyme degradation by 24 h; however, after a lag (which was also observed with *E. coli* DH5α pEDH27, FIG. 3) a small increase in the reducing sugar concentration with a concomitant increase in ethanol production is seen, demonstrating the degradation of pectin to smaller oligogalacturonides and release of fermentable sugars by PelA.

Example 4

PelB showed homology to family I pectate lyases (PL1), but not to any other class. PelB showed highest identity of only 28% to *Bacillus* sp. YA-14 PelK, *B. licheniformis* ATCC 14580 Pel, and *B. subtilis* reference strain 168 Pel. In addition, PelB showed lower identity to other pectate lyases: 27% to *Thermotoga maritime* PelA, and 26% to *B. subtilis* BS-2 Pel, and *B. amyloliquefaciens* TB-2 Pel.

Other than PelB, all of the enzymes listed above contain all three conserved calcium binding sites, all three conserved catalytic sites, and all six of the sites conserved in all thermostable PL1 pecate lyase. PelB contains the three conserved calcium binding sites, but does not contain any of the conserved catalytlic sites, and only six of the seven sites conserved in all thermostable PL1 pecate lyase.

There are four highly conserved consecutive Asn ladder positions in all Pels that help to stabilize the β bend that is structurally unique to the parallel β helix that is present throughout polysaccharide families 1, 3, 6, 9, and 19. The Asn ladder can be composed of Asn or amino acids that are able to act with similar function, such as, Cys, Gln, Thr, or Ser. PelB only contain half of the conserved Asn ladders: Ser$^{219}$ and Gln$^{303}$. Whereas, all of the other enzymes being compared to PelB in this study contain all four of the conserved Asn ladders. PelB has Pro$^{248}$ and Gly$^{270}$, instead of the Asn found in the other enzymes.

In addition, PelB only has six of the ten invariant amino acids highly conserved in the pectate lyase superfamily. PelB does contain invariant amino acids, Gly$^{47}$, Gly$^{48}$, Asp$^{182}$, Trp$^{193}$, Asp$^{195}$, and H$^{196}$. All of the other enzymes listed above contain all ten of the invariant amino acids except *Thermotoga maritime* PelA, which differs only at Val$^{40}$ (reference to TmaPelA). PelB's Ser$^{256}$, Val$^{258}$, Lys$^{244}$, Tyr$^{36}$ differ from the invariant Arg, Pro, Thr, and Gly, respectively.

There are three pectate lyase conserved sequence patterns: vWIDH, AxDIKGxxxxVTxS, and VxxRxPxxRxGxxHxxxxN. PelB only contains two of the three conserved sequence patterns. PelB and the enzymes mentioned above all contain the vWIDH sequence which is the core structure of the parallel β-helix. Trp, Asp, and His are three of the 10 invariant amino acids found in all pecate lyases, and are Trp$^{193}$, Asp$^{195}$, and H$^{196}$.

The second sequence, AxDIKGxxxxVTxS, is found partially homologous in PelB and the other enzymes being compared to it. Asp$^{206}$ of PelB is an invariant amino acid that is seen in pectate lyases, but not in pectin lyases. It is thought to participate in the calcium coordination. This is not surprising since pectin lyases do not require calcium to be active like pectate lyases do. Thr$^{215}$ and Ser$^{217}$ are also invariant amino acids that are seen in pecate lyases, but not in pectin lyases. They are located on the β strands near the vWIDH region.

The third sequence, VxxRxPxxRxGxxHxxxxN, is not found in PelB, but is present in the other enzymes being compared. The two Arg present in this sequence are positively charged amino acids near the calcium binding site that recognize the negatively charged substrates. The first Arg present in this sequence is also one of the ten invariant amino acids found in the pectate lyase superfamily, but PelB has Ser$^{256}$. The Pro is also one of the ten invariant amino acids found in the pecate lyase superfamily, and is involved in the calcium binding by dictating the orientation of the first Arg in this sequence (PelB has Ser$^{256}$ instead) to bind to water. The second Arg in the sequence is a conserved catalytic site that is present in pectate lyase and absent in pectin lyases. PelB does not conserve this Arg and instead has Ser$^{261}$. The His present in this sequence is also positively charged invariant residue found in the Pel subfamily, but PelB does not conserve it and has Ile$^{266}$.

In addition to the two arginines mentioned in the VxxRxPxxRxGxxHxxxxN sequence, the other catalytic binding site that is not conserved is a positively charged amino acid, Lys$^{189}$ (reference to TmaPelA). PelB has a gap at this conserved location. These three amino acids, two Arg and one Lys, are positively charged amino acids that are located near the calcium binding site and allow for the recognition of negatively charged substrates. The presence of Ser$^{256}$ and Ser$^{261}$ instead of the conserved Arg and a gap instead of the conserved Lys could be the reason the C64 PelB has activity on PGA and highly methylated pectin even though it is a pectate lyase.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for degrading pectin comprising:
contacting a composition comprising pectin with a composition comprising an enriched polypeptide, wherein the enriched polypeptide has pectinase activity under conditions suitable for the degradation of the pectin, wherein the polypeptide comprises an amino acid sequence, wherein the amino acid sequence and the amino acid sequence of SEQ ID NO:4 have at least 80% identity, and wherein the pectin is degraded.

2. The method of claim 1 further comprising contacting the degraded pectin with a polypeptide having oligogalacturonate activity.

3. The method of claim 1 wherein the composition comprises a lignocellulosic material.

4. The method of claim 3 wherein the lignocellulose material is obtained from a fruit or a vegetable.

5. A method for degrading pectin comprising:
contacting a composition comprising pectin with a genetically modified microbe comprising an exogenous polynucleotide encoding a polypeptide having pectinase activity under conditions suitable for expression of the exogenous polypeptide and degradation of the pectin, wherein the polypeptide comprises an amino acid sequence, wherein the amino acid sequence and the amino acid sequence of SEQ ID NO:4 have at least 80% identity, and wherein the pectin is degraded.

6. The method of claim 5 further comprising contacting the degraded pectin with a polypeptide having oligogalacturonate activity.

7. The method of claim 5 wherein the genetically modified microbe expresses an exogenous polypeptide having oligogalacturonate activity.

8. The method of claim 5 wherein the genetically modified microbe produces ethanol.

9. The method of claim 5 wherein the composition comprises a lignocellulosic material.

10. The method of claim 9 wherein the lignocellulose material is obtained from a fruit or a vegetable.

11. The method of claim 5 wherein the genetically modified microbe is a gram-negative microbe or a fungus.

12. The method of claim 5 wherein the genetically modified microbe is *E. coli* or *S. cerevisiae*.

13. The method of claim 5 wherein the polypeptide is enriched.

* * * * *